United States Patent
Yamasaki et al.

(10) Patent No.: US 6,420,409 B1
(45) Date of Patent: Jul. 16, 2002

(54) BENZIMIDAZOLE DERIVATIVES

(75) Inventors: Noritsugu Yamasaki, Hyogo; Takafumi Imoto, Niigata; Teruo Oku, Osaka; Akira Katayama, Ibaraki; Hiroshi Kayakiri, Osaka; Osamu Onomura, Nagasaki; Takahiro Hiramura; Masahiro Nishikawa, both of Niigata; Hitoshi Sawada, Ibaraki, all of (JP)

(73) Assignee: Fujisawa Pharmaceutical Co., Ltd. (JP)

( * ) Notice: Subject to any disclaimer, the term of this patent is extended or adjusted under 35 U.S.C. 154(b) by 0 days.

(21) Appl. No.: 09/446,749
(22) PCT Filed: Jun. 26, 1998
(86) PCT No.: PCT/JP98/02885
§ 371 (c)(1),
(2), (4) Date: Mar. 24, 2000
(87) PCT Pub. No.: WO99/00373
PCT Pub. Date: Jan. 7, 1999

(30) Foreign Application Priority Data

Jun. 27, 1997 (JP) .............................. 9-187696
Mar. 25, 1998 (JP) .............................. 10-76357

(51) Int. Cl.[7] .................... A61K 31/415; C07D 235/04; C07D 235/10
(52) U.S. Cl. ................. 514/394; 548/304.7; 548/309.7
(58) Field of Search ..................... 514/394; 548/304.7, 548/309.7

(56) References Cited

U.S. PATENT DOCUMENTS

| | | |
|---|---|---|
| 3,152,142 A | 10/1964 | Moyle et al. |
| 4,179,505 A | 12/1979 | Raeymaekers et al. |
| 4,243,806 A | 1/1981 | Raeymaekers et al. |
| 4,977,175 A | 12/1990 | Ohta et al. |
| 5,294,631 A | 3/1994 | Franz et al. |
| 5,328,919 A | 7/1994 | Naka et al. |
| 5,401,764 A | 3/1995 | Naka et al. |
| 5,587,393 A * | 12/1996 | Narr |
| 5,591,762 A | 1/1997 | Hauel et al. |
| 5,594,003 A | 1/1997 | Hauel et al. |
| 5,602,127 A | 2/1997 | Hauel et al. |
| 5,614,419 A | 3/1997 | Hauel et al. |
| 5,684,029 A * | 11/1997 | Narr |
| 5,703,110 A | 12/1997 | Naka et al. |
| 5,705,517 A | 1/1998 | Naka et al. |
| 6,166,219 A * | 12/2000 | Yamasaki et al. |

FOREIGN PATENT DOCUMENTS

| | | | |
|---|---|---|---|
| DE | 676 196 | 6/1939 | |
| DE | 42 37 557 A1 | 5/1994 | ......... C07D/235/10 |
| EP | 0 260 744 A2 | 3/1988 | ......... C07D/235/06 |
| EP | 0 468 470 A1 | 1/1992 | ......... C07D/403/14 |
| EP | 0696 583 A1 | 2/1996 | ......... C07D/235/08 |
| EP | 0 882 718 A1 | 9/1998 | |
| EP | 0882718 A1 | 12/1998 | ......... C07D/235/08 |
| FR | 2291749 | 6/1976 | |
| GB | 2 053 215 A | 2/1981 | ......... C07D/235/08 |
| GB | 2 177 393 A | 1/1987 | ......... C07D/235/06 |
| HU | 217 084 B | 9/1992 | |
| JP | 51-133267 | 11/1976 | ......... A61K/031/41 |
| JP | 5-222000 | 8/1993 | |
| WO | WO 96/16644 | 6/1996 | .......... A61K/31/00 |

OTHER PUBLICATIONS

Willitzer et al., "Synthese und Antivirale Wirksamkeit von Substituierten 5–Ureido–und 5–Thioureidobenzimidazolderivaten," Pharmazie 33, H. 1 (1978), pp 30–38.

Tanaka et al., "Studies on Anti–Platelet Agents. II. Synthesis and Platelet–Inhibitory Activity of 5–Methyl–4–(3–pyridyl)–2–(substituted Benzimidazol–5–yl)imidazoles," Chem. Pharm. Bull., vol. 42, No. 3, 1994, pp 560–569.

Gartui et al., "Synthesis and Antimycotic Activity of Some Benzyloxyimino Compounds,"Pharmazie 42:378–381, 1987.

Haque et al., "Ambident Heterocyclic Reactivity: Alkylation of Substituted and 2, 4–Disubstituted Benzimidazoles," Aust. J. Chem. 47:1523–1535, 1994.

Willitzer, CA 89:24221, abstract of Pharmazie, 33(1), pp30–38, 1978.*

Willitzer, CA 87:135328, abstract of DD 123466, 1976.*

Narr, CA 96:118605, 1996, Abstract of US Pat# 5587393.*

Narr, CA 97:101781, 1997, abstract of US Pat# 5684029.*

\* cited by examiner

*Primary Examiner*—D. Margaret Seaman
(74) *Attorney, Agent, or Firm*—Fish & Richardson, P.C.

(57) ABSTRACT

A novel benzimidazole derivative or a salt thereof is provided, which is represented by the formula:

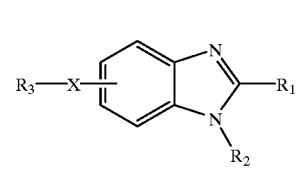

(I)

wherein $R_1$ represents an alkyl group, etc., $R_2$ represents a substituted or unsubstituted aromatic lower alkyl group, $R_3$ represents an alkyl group, etc., and -X- is represented by the following formula (V):

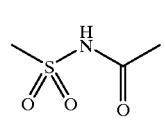

(V)

etc. This derivative or a salt thereof is useful as medicine.

19 Claims, 22 Drawing Sheets

(1 3)

(1 4)

(1 5)

(1 6)

(17)

(18)

(19)

(20)

(21)

(22)

(23)

(24)

(25)

(26)

(27)

(28)

(29)

(30)

(31)

(32)

(33)

(34)

(35)

(36)

(37)

(38)

(39)

(40)

(41)

(42)

(43)

(44)

(45)

(46)

(47)

(48)

(+) form (49)

(−) form (50)

(51)

(52)

(53)

(54)

(55)

(56)

(57)

(58)

(59)

(60)

(61)

(62)

(63)

(64)

(65)

(66)

(67)

(68)

(69)

(70)

(71)

(72)

(73)

(74)

(75)

(76)

(77)

(R)

(78)

(S)

(79)

optically active compound (80)

optically active compound (81)

optically active compound (82)

optically active compound (83)

(84)

(85)

(86)

(87)

(88)

(89)

(90)

(91)

(92)

(93)

(94)

(95)

(96)

BENZIMIDAZOLE DERIVATIVES

This is a 371 of PCT/JP98/02885, filed Jun. 26, 1998.

TECHNICAL FIELD

The present invention relates to novel benzimidazole derivatives, and, more precisely, to novel benzimidazole derivatives and their pharmaceutically acceptable salts having blood sugar level-depressing activity or PDE5-inhibiting activity. The present invention also relates to pharmaceutical compositions comprising, as an active ingredient, such benzimidazole derivatives or their salts.

DISCLOSURE OF THE INVENTION

The subject matter of the present invention is to provide novel benzimidazole derivatives and their pharmaceutically acceptable salts, and also pharmaceutical compositions which comprise, as an active ingredient, such benzimidazole derivatives or their pharmaceutically acceptable salts, and which are useful for preventing and treating impaired glucose tolerance, diabetes (type II diabetes), diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy, etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia (e.g., abnormal saccharometabolism such as feeding disorders, etc.), hypertension, stenocardia, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis aiiostenosis (e.g., after percutaneous arterioplasty), distal angiopathy, cerebral apoplexy, chrci reversible obstructions (e.g., bronchitis, asthma (chronic asthma, allergic asthma), etc.), autoimmune disease, allergic rhinitis, urticaria, glaucoma, diseases characterized by enteromotility disorders (e.g., hypersensitive enteropathy syndrome, etc.), impotence (e.g., organic impotence, psychic impotence, etc.), nephritis, cachexia (e.g., progressive weight loss due to the lipolysis, myolysis, anemia, edema, anorexia, etc. associated with chronic diseases such as cancer, tuberculosis, endocrine disorder, AIDS, etc.), pancreatitis, or restenosis after PTCA.

The present inventors provide a novel benzimidazole derivative represented by the following formula (I) and its pharmaceutically acceptable salt, and a pharmaceutical composition comprising said compound or its pharmaceutically acceptable salt as an effective ingredient, which is usable for preventing and treating impaired glucose tolerance, diabetes (type II diabetes), diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy, etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia(e.g., abnormal saccharometabolism such as feeding disorders, etc.), hypertension, stenocardia, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), autoimmune disease, allergic rhinitis, urticaria, glaucoma, diseases characterized by enteromotility disorders (e.g., hypersensitive enteropathy syndrome, etc.), impotence (e.g., organic impotence, psychic impotence, etc.), and nephritis, cachexia (e.g., progressive weight loss due to the lipolysis, myolysis, anemia, edema, anorexia, etc. associated with chronic diseases such as cancer, tuberculosis, endocrine disorder, AIDS, etc.), pancreatitis, or restenosis after PTCA.

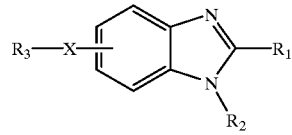

(I)

wherein $R_1$ represents a hydrogen atom, a lower alkyl group, a lower alkoxy group, or a lower alkylthio group;

$R_2$ represents an aromatic lower alkyl group, which may be substituted with one or more groups selected from a halogen atom, an alkyl group, a halo-lower alkyl group, a nitro group, a lower alkoxycarbonyl group, an aromatic group, an aromatic lower alkyloxy group, a lower cycloalkyloxy-lower alkyl group, an aromatic lower alkyl group, an aromatic lower alkenyl group, an aromatic lower alkynyl group, an aromatic oxy lower alkyl group, a lower cycloalkyl-lower alkyloxy group, an alkenyl group, a lower alkoxy group, a lower alkylthio group, a lower alkanesulfinyl group, a lower alkanesulfonyl group, and a lower alkanesulfonylcarbamoyl group;

$R_3$ represents an alkyl group, a hydroxy lower alkyl group, an alkenyl group, an aromatic group, a halogenated aromatic group, a lower alkyl aromatic group, a lower alkenyl aromatic group, an aromatic lower alkyl group, or an aromatic lower alkenyl group; and —X— is a cross-linking group represented by any one of the following formulas (II) to (VI):

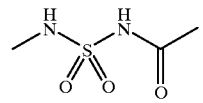

(II)

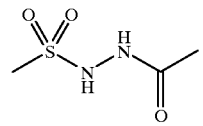

(III)

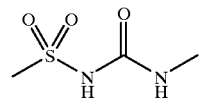

(IV)

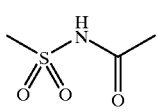
(V)
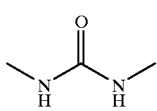
(VI)
In the above formula (I), $R_1$ is preferably a lower alkyl group, and X is a cross-linking group represented by the above formula (V).
The benzimidazole derivatives provided by the present invention can be prepared according to the following reaction formulae (a) to (m).
(a)
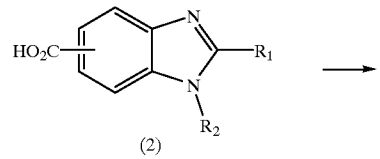
(1)
→
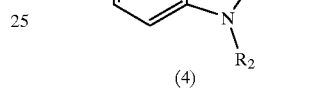
(2)
(b)
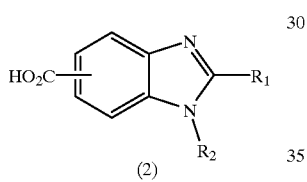
(2)
→
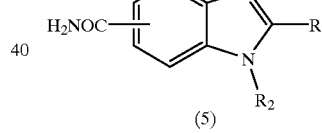
(3)
(c)
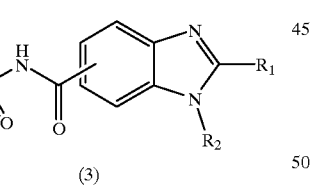
(2)
→
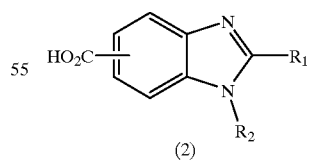
(4)
(d)
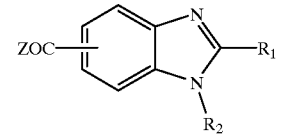
(4)
→
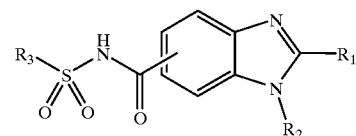
(3)
(e)
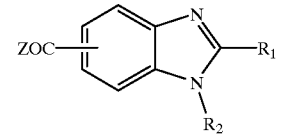
(4)
→
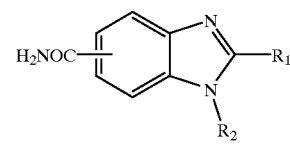
(5)
(f)
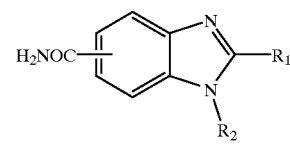
(5)
→
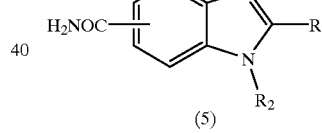
(3)
(g)
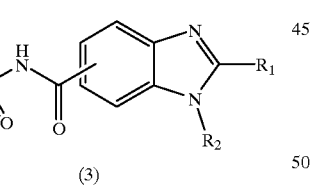
(2)
→
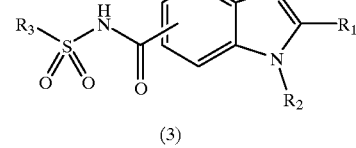
(6)

(h)

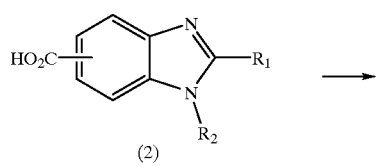

(2)

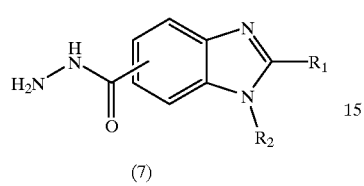

(7)

(i)

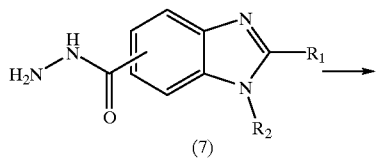

(7)

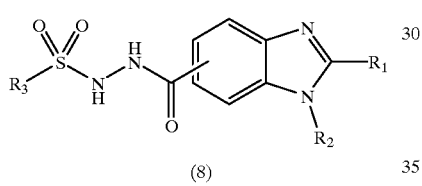

(8)

(j)

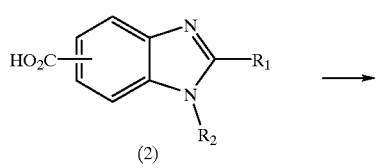

(2)

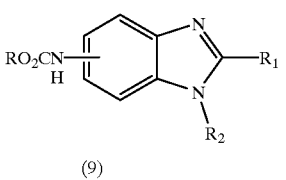

(9)

(k)

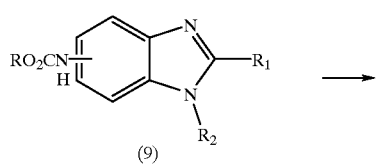

(9)

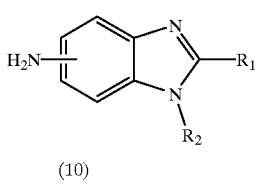

(10)

(l)

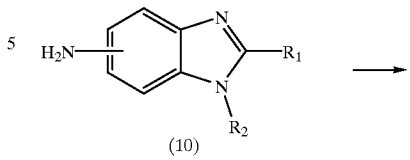

(10)

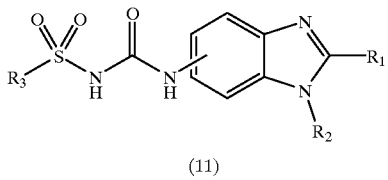

(11)

(m)

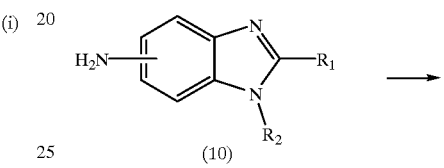

(10)

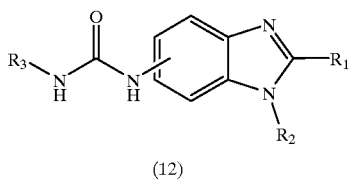

(12)

wherein $R_1$, $R_2$, and $R_3$ have the same meanings as described above, R is a protecting group for a carboxyl group, and Z is a halogen atom.

Compound (1) can be converted to Compound (2) by hydrolyzing it with a base such as lithium hydroxide, sodium hydroxide, potassium hydroxide, etc. (Reaction formula (a)). Compound (3) can be obtained by treating Compound (2) with a carboxylic acid activator represented by N,N'-carbonyldiimidazole, 1-(3-dimethylaminopropyl)-3-ethylcarbodiimide or a salt thereof, dicyclohexylcarbodiimide, isobutyloxycarbonyl chloride, isobutyloyl chloride, pivaloyl chloride, isobutyl chloroformate, diphenylphosphoryl azide, or diethyl cyanophosphate followed by reacting with the corresponding sulfonamide in the presence of a base represented by diazabicycloundecene, triethylamine, 4-dimethylaminopyridine, N,N-dimethylaniline, pyridine, N-methylmorpholine, N-ethylpiperidine, potassium hydroxide, sodium hydroxide, potassium phosphate, potassium hydrogencarbonate, potassium carbonate, sodium carbonate, sodium hydride, potassium t-butoxide, sodium methoxide, or sodium ethoxide (Reaction formula (b)) The compound obtained by the reaction between Compound (2) and the carboxylic acid activator may or may not be isolated.

Compound (6) can be obtained by reacting Compound (2) with an aminosulfonamide in the presence of carbonyldiimidazole, etc. (Reaction formula (g)).

Compound (7) can be obtained by reacting Compound (2) with hydrazine with one of the amino groups thereof protected in the presence of carbonyldiimidazole, etc. and treating the resulting product under the acidic conditions (Reaction formula (h)). Compound (7) can be converted to Compound (8) by reacting it with sulfonyl chloride or the like in the presence of a base such as triethylamine, etc. (Reaction formula (i)).

Compound (2) can be converted to Compound (9) by reacting it with diphenylphosphoryl azide and an alcohol in the presence of a base such as triethylamine, etc. (Reaction formula (j)). Compound (9) can be converted to Compound (10) by treating it under acidic conditions (Reaction formula (k)). Compound (10) can be converted to Compound (11) by reacting it with sulfonyl isocyanate (Reaction formula (1)), and to Compound (12) with isocyanate (Reaction formula (m)), respectively.

The terms "sulfonamides," "aminosulfonamides," "sulfonyl chlorides," "sulfonyl isocyanates," and "isocyanates" used herein mean those groups having the above-described substituent $R_3$, where a functional group, if present on the carbon atom thereof, may or may not be protected. Compound (3) having the protected functional group can be converted to the desired compound by deprotection.

Compound (2) can be converted to the corresponding acid halide represented by Compound (4) by reacting it with thionyl chloride, thionyl bromide, phosphorus trichloride, phosphorus pentachloride, phosphorus oxychloride, oxalyl chloride, or phosphorus tribromide, etc. (Reaction formula (c)). Compound (3) can be synthesized from Compound (4) and sulfonamide in the presence or absence of a base (Reaction formula (d)).

Compound (5) can be synthesized by reacting Compound (4) with ammonia or ammonia water (Reaction formula (e)). Compound (5) can also be synthesized from Compound (1) and ammonia or ammonia water. Alternatively, Compound (5) can be obtained by reacting an intermediate that is produced from Compound (2) and the carboxylic acid activator in the Reaction formula (b) with ammonia or ammonia water. Compound (3) can also be synthesized from Compound (5) and sulfonyl chloride in the presence or absence of a base (Reaction formula (f)).

When $R_1$, $R_2$, or $R_3$ has a reactive substituent in any of the compounds of Compound (1) to Compound (12), the substituent can be replaced to the other during the steps of (a) to (m) or in the final step.

If desired, the intermediates formed in the above-mentioned steps may optionally be purified, prior to being subjected to the next step, through any conventional purification including, for example, recrystallization, column chromatography, thin-layer chromatography, high-performance liquid chromatography and the like. If also desired, the final products of the compounds of the present invention may optionally be purified through any conventional purification which is employed in the art of purifying organic compounds and which includes, for example, recrystallization, column chromatography, thin-layer chromatography, high-performance liquid chromatography and the like. To identify these compounds, employable is any of NMR spectrography, mass spectrography, IR spectrography, elementary analysis, measurement of melting point and others.

Preferred Examples and their details of various definitions as referred to herein to be within the scope of the present invention are described below.

The alkyl group used herein means a linear or branched alkyl group having 1 to 20 carbon atoms, including a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a 2,2-dimethylpentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 2,2-dimethyl-butyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methyl-hexyl group, a 1-ethylpentyl group, a 2-ethylpentyl group, a 1,1-dimethylpentyl group, a 2,2-dimethylpentyl group, a 3,3-dimethylpentyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 1,1-dimethylhexyl group, a 2,2-dimethylhexyl group, a 3,3-dimethylhexyl group, a n-nonyl group, a 1-methyloctyl group, a 2-methyloctyl group, a 3-methyloctyl group, a 4-methyloctyl group, a 5-methyloctyl group, a 6-methyloctyl group, a 7-methyloctyl group, a 1-ethyl-heptyl group, a 2-ethyl heptyl group, a 1,1-dimethylheptyl group, a 2,2-dimethylheptyl group, a 3,3-dimethylheptyl group, an n-decyl group, a 1-methylnonyl group, a 2-methylnonyl group, a 3-methylnonyl group, a 4-methylnonyl group, a 1-ethyloctyl group, a 2-ethyloctyl group, an n-undecyl group, an n-dodecyl group, an n-tridecyl group, an n-tetradecyl group, an n-pentadecyl group, an n-hexadecyl group, an n-octadecyl group, etc. Preferably, those having 2 to 8 carbon atoms are used.

The term "lower" means the number of carbon atoms from 1 to 6. Preferable examples of the lower alkyl group include a straight chain or branched chain alkyl group such as methyl, ethyl, n-propyl, i-propyl, n-butyl, i-butyl, sec-butyl, t-butyl, n-pentyl, i-pentyl, sec-pentyl, t-pentyl, 2-methylbutyl, n-hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 1-ethyl-1-methylpropyl, or the like. Those having carbon atoms of 1 to 3 are more preferred.

The term "hydroxy lower alkyl group" means the above-described lower alkyl group to which a hydroxyl group is bonded, including 1-hydroxyethyl, 2-hydroxyethyl, 1-hydroxypropyl. 2-hydroxypropyl, 3-hydroxypropyl, 1-hydroxybutyl, 2-hydroxybutyl, 3-hydroxybutyl, 4-hydroxybutyl, 1-hydroxypentyl, 2-hydroxypentyl, 3-hydroxypentyl, 4-hydroxypentyl, 5-hydroxypentyl, 1-hydroxyhexyl, 2-hydroxyhexyl, 3-hydroxyhexyl, 4-hydroxyhexyl, 5-hydroxyhexyl, 6-hydroxylhexyl, 3,4-dihydroxybutyl, 2,4-dihydroxypentyl, 1,3,5-trihydroxyhexyl, (2-hydroxy-1-methyl)ethyl, (1-hydroxy-2-methyl)propyl, (2-hydroxy-2-mnethyl)propyl, (2-hydroxymethyl)propyl, (3-hydroxy-1-methyl)propyl, (4-hydroxy-1-methyl)butyl, (1-hydroxy-3-methyl)-butyl, (2-hydroxy-3-methyl)butyl, (3-hydroxy-3-methyl)butyl, (3-hydroxymethyl)butyl, (1-hydroxy methyl)pentyl, (2-hydroxy-4-methyl)pentyl, (3-hydroxy-4-methyl)pentyl, (4-hydroxy-4-methyl)-pentyl, (4-hydroxymethyl)pentyl, (1,1-dimethyl-2-hydroxy)ethyl, (1,1-dimethyl-2-hydroxy)propyl, (1,1-dimethyl-3-hydroxy)propyl, (1,1-dimethyl-2-hydroxy)butyl, (1,1-dimethyl-3-hydroxy)butyl, (1,1-dimethyl-4-hydroxy)butyl, (1-hydroxy-1-methyl)butyl, (2,2-dimethyl-1-hydroxy)butyl, (2,2-dimethyl-3-hydroxy) butyl, (2,2-dimethyl-4-hydroxy)butyl, (2-hydroxymethyl-2-methyl)butyl, (3,3-dimethyl-1-hydroxy)butyl, (3,3-dimethyl-2-hydroxy)butyl, (3,3-dimethyl-4-hydroxy)butyl, (3-hydroxymethyl-3-methyl)butyl, etc.

The alkenyl group used herein means a linear or branched alkenyl group having 2 to 20 carbon atoms, including a vinyl group, a 1-propenyl group, a 2-propenyl group, a 1-butenyl group, a 2-butenyl group, a 3-butenyl group, a 1-methyl-1-propenyl group, a 2-methyl-1-propenyl group, a 1-methyl-2-propenyl group, a 2-methyl-2-propenyl group, a 1-pentenyl group, a 2-pentenyl group, a 3-pentenyl group, a 4-pentenyl group, a 1-methyl-1-butenyl group, a 2-methyl-1-butenyl group, a 3-methyl-1-butenyl group, a 2-methyl-2-butenyl group, a 3-methyl-2-butenyl group, a 2-methyl-3-butenyl group, a 1,3-butadienyl group, a 3-methyl-3-butenyl group, a 1-hexenyl group, a 2-hexenyl group, a 3-hexenyl group, a 4-hexenyl group, a 5-hexenyl group, a 2-methyl-1-pentenyl group, a 3-methyl-1-pentenyl group, a 4-methyl-1-pentenyl group, a 1-heptenyl group, a 1-octenyl group, a 1-nonenyl group, a -decenyl group, a 1-undecenyl group, a 1-dodecenyl group, a 1-tridecenyl group, a 1-tetradecenyl group, a 1-pentadecenyl group, a 1-hexadecenyl group, a 1-octadecenyl group, etc. Preferably, those having 2 to 8 carbon atoms are used.

The lower alkenyl group preferably includes a straight chain or branched chain lower alkenyl group such as ethenyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl. 4-hexenyl, 5-hexenyl, 1,4-methylpentenyl, etc.

The halogen atom includes fluorine, chlorine, bromine, and iodine atoms and its preferable examples are fluorine, chlorine, and bromine atoms.

The halo-lower alkyl group means the above-described lower alkyl group substituted with the above-described halogen atom, including fluoromethyl, difluoromethyl, trifluoromethyl, chloromethyl, dichloromethyl, trichloromethyl, bromomethyl, dibromomethyl, tribromomethyl, iodomethyl, 1-fluoroethyl, 1-chloroethyl, 1-bromoethyl, 2-fluoroethyl, 2-chloroethyl, 2-bromoethyl, 1,1-difluoroethyl, 1,1-dichloroethyl, 1,1-dibromoethyl, 2,2-difluoroethyl, 2,2-dichloroethyl, 2,2-dibromoethyl, 1,2-difluoroethyl, 1,2-dichloroethyl, 1,2-dibromoethyl, 2,2,2-trifluoroethyl, heptafluoroethyl, 1-fluoropropyl, 1-chloropropyl, 1-bromopropyl, 2-fluoropropyl, 2-chloropropyl, 2-bromopropyl, 3-fluoropropyl, 3-chloropropyl, 3-bromopropyl, 1,1-difluoropropyl, 1,1-dichloropropyl, 1,1-dibromopropyl, 1,2-difluoropropyl, 1,2-dichloropropyl, 1,2-dibromopropyl, 2,3-difluoropropyl, 2,3-dichloropropyl, 2,3-dibromopropyl, 3,3,3-trifluoropropyl, 2,2,3,3,3-pentafluoropropyl, 2-fluorobutyl, 2-chlorobutyl, 2-bromobutyl, 4-fluorobutyl, 4-chlorobutyl, 4-bromobutyl, 4-iodobutyl, 3,4-dichlorobutyl, 2,4dibromopentyl, 3,3,4,4,4-pentafluorobutyl, 2,2,3,3,4,4,4-heptafluorobutyl, perfluorobutyl, 2-fluoropentyl, 2-chloropentyl, 2-bromopentyl, 5-fluoropentyl, 5-chloropentyl, 3-iodopentyl, omopentyl, 2-fluorohexyl, 2-chlorohexyl, 2-bromohexyl, 6-fluorohexyl, 6-chlorohexyl, 6-bromohexyl, 1,3,5-trifluorohexyl, perfluorohexyl, etc.

The lower alkoxy group means a straight chain or branched chain alkoxyl group having up to 6 carbon atoms, including methoxy, ethoxy, n-propyloxy, i-propyloxy, n-butyloxy, i-butyloxy, sec-butyloxy, t-butyloxy, n-pentyloxy, i-pentyloxy, sec-pentyloxy, 2,2-dimethylpropyloxy, 2-methylbutoxy, n-hexyloxy, i-hexyloxy, t-hexyloxy, sec-hexyloxy, 2-methylpentyloxy, 3-methylpentyloxy, 1-ethyl-butyloxy, 2-ethylbutyloxy, 1,1-dimethylbutyloxy, 2,2-dimethyl-butyloxy, 3,3dimethylbutyloxy, 1-ethyl-1-methylpropyloxy, etc.

The lower alkoxycarbonyl group means a carbonyl group to which the above-described lower alkoxyl group is bonded, including methoxycarbonyl, ethoxycarbonyl, n-propyloxycarbonyl, i-propyloxycarbonyl, n-butyloxycarbonyl, i-butyloxycarbonyl, sec-butyloxycarbonyl, t-butyloxycarbonyl, n-pentyloxycarbonyl, i-pentyloxycarbonyl, sec-pentyloxycarbonyl, t-pentyloxycarbonyl, 2,2-dimethylpropyloxycarbonyl, 2-methylbutyloxycarbonyl, n-hexyloxycarbonyl, i-hexyloxycarbonyl, t-hexyloxycarbonyl, sec-hexyloxycarbonyl, 2-methylpentyloxycarbonyl, 3-methylpentyloxy-carbonyl, 1-ethylbutyloxycarbonyl, 2-ethylbutyloxycarbonyl, 2,2-dimethylbutyloxycarbonyl, 3,3-dimethylbutyloxycarbonyl, 1-ethyl-1-methylpropyloxycarbonyl, etc.

The lower cycloalkyloxy-lower alkyl group means the above-described lower alkyl group having bonded thereto a cycloalkyloxy group having 3 to 7 carbon atoms, for example, cyclopropyloxy, cyclobutyloxy, cyclopentyloxy, cyclohexyloxy, cycloheptyloxy, and the like. Examples thereof include (cyclopropyloxy)methyl, 2-(cyclopropyloxy)ethyl, (cyclobutyloxy)methyl, 3-(cyclobutyloxy)propyl, cyclopentyloxymethyl, 2-(cyclopentyloxy)ethyl, 4-(cyclopentyloxy)butyl, (cyclohexyloxy)methyl, 1-(cyclo-hexyloxy)ethyl, 2-(cyclohexyloxy)ethyl, 3-(cyclohexyloxy)propyl, 2-(cyclohexyloxy)propyl, 1-(cyclohexyloxy)propyl, 4-(cyclo-hexyloxy)butyl, 3-(cyclohexyloxy)butyl, 2-(cyclohexyloxy)butyl, 6-(cyclohexyloxy)hexyl, 1-(cyclohexyloxy)butyl, (cyclo-heptyloxy)methyl, etc.

The lower cycloalkyl-lower alkyloxy group means the above-described lower alkoxy group having bonded thereto a cycloalkyl group having 3 to 7 carbon atoms, for example, cyclopropyl, cyclobutyl, cyclopentyl, cyclohexyl, cycloheptyl, and the like. Examples thereof include (cyclopropylmethyl)oxy, (2-cyclopropylethyl)oxy, (cyclobutylmethyl)oxy, (3-cyclobutylpropyl)oxy, (cyclopentyl-methyl)oxy, (2-cyclopentylethyl)oxy, (4-cyclopentylbutyl)oxy, (cyclohexylmethyl)oxy, (1-cyclohexylethyl)oxy, (2-cyclohexyl-ethyl)oxy, (3-cyclohexylpropyl)oxy, (2-cyclohexylpropyl)oxy, (1-cyclohexylpropyl)oxy, (4-cyclohexylbutyl)oxy, (3-cyclohexyl-butyl)oxy, (2-cyclohexylbutyl)oxy, (6-cyclohexylhexyl)oxy, (1-cyclohexylbutyl)oxy, cycloheptylmethyloxy, etc.

The lower alkylthio group means a straight chain or branched chain alkylthio group having up to 6 carbon atoms, including methylthio, ethylthio, n-propylthio, i-propylthio, n-butylthio, i-butylthio, sec-butylthio, t-butylthio, n-pentylthio, i-pentylthio, sec-pentylthio, 2,2-dimethylpropylthio, 2-methylbutylthio, n-hexylthio, i-hexylthio, t-hexylthio, sec-hexylthio, 2-methyl-pentylthio, 3-methylpentylthio, 1-ethylbutylthio, 2-ethylbutylthio, 1,1-dimethylbutylthio, 2,2-dimethylbutylthio, 3,3-dimethyl-butylthio, 1-ethyl-1-methylpropylthio, etc. Preferred are those having carbon atoms 1 to 4 such as methylthio, ethylthio, n-propylthio, i-propylthio, n-butylthio, i-butylthio, sec-butylthio, or t-butylthio.

The lower alkanesulfinyl group means a straight chain or branched chain alkanesulfinyl group with the alkyl moiety thereof containing up to 6 carbon atoms, including methanesulfinyl, ethanesulfinyl, 1-propanesulfinyl, 2-propanesulfinyl, 1-butanesulfinyl, 2-butanesulfinyl, 1,1-dimethylethanesulfinyl, 1-(2-methylpropane)-sulfinyl, 1-pentanesulfinyl, 2-pentanesulfinyl, 3-pentanesulfinyl, 1-(3-methylbutane)sulfinyl, 1,1-dimethylpropanesulfmyl, 1-hexanesulfinyl, 2-hexanesulfinyl, 3-hexanesulfinyl, 1-(2-methyl-pentane)sulfinyl, 1-(3-methylpentane)sulfinyl, 1-(4-methyl-pentane)sulfinyl, 2-ethylbutane-1-sulfmyl, 3-ethylbutane-1-sulfinyl, 1,1-dimethylbutane-1-sulfinyl, 2,2-dimethylbutane-1-sulfinyl, 3,3-dimethylbutane-1-sulfinyl, 1-ethyl-1-methyl-propane-1-sulfinyl, etc.

The lower alkanesulfonyl group means a straight chain or branched chain alkanesulfonyl group with the aikyl moiety thereof containing up to 6 carbon atoms, including methanesulfonyl, ethanesulfonyl, 1-propanesulfonyl, 2-propanesulfonyl, 1-butanesulfonyl, 2-butanesulfinyl, 1,1-dimethylethanesulfonyl, 1-(2-methylpropane)-sulfonyl, 1-pentanesulfonyl, 2-pentanesulfonyl, 3-pentanesulfonyl, 1-(3-methylbutane)sulfonyl, 1,1-dimethylpropanesulfonyl, 1-hexanesulfonyl, 2-hexanesulfonyl, 3-hexanesulfonyl, 1-(2-methyl-pentane)sulfonyl, 1-(3-methylpentane) sulfonyl, 1-(4-methyl-pentane)sulfonyl, 2-ethylbutane-1-sulfonyl, 3-ethylbutane-1-sulfonyl, 1,1-dimethylbutane-1-sulfonyl, 2,2-dimethylbutane-1-sulfonyl, 3,3-dimethylbutane-1-sulfonyl, 1-ethyl-1-methyl-propane-1-sulfonyl, etc.

The aromatic group means an aryl or heterocyclic aromatic group. Throughout this specification, the aryl group means those having 6 to 10 carbon atoms such as phenyl, naphthyl, or the like. When simply referred to as "naphthyl group", it includes 1-naphthyl and 2-naphthyl groups. The heterocyclic aromatic group means an unsaturated monocyclic or polycyclic heterocyclic group containing at least one hetero atom such as oxygen, sulfur, and nitrogen atoms, including pyrrolyl, imidazolyl, furyl, thienyl, thiazolyl, pyridyl, benzimidazolyl, benzofuryl, indolyl, benzothienyl, quinolyl, isoquinolyl, thiophenyl, furanyl, etc. The position of the substituted hetero atom as described above on the aromatic ring is not particularly restricted.

The halo-aromatic group means the above-described aromatic group substituted with the above-described halogen atom, including 2-fluorophenyl, 2-chlorophenyl, 2-bromophenyl, 2-iodophenyl, 3-fluorophenyl, 3-chlorophenyl, 3-bromophenyl, 3-iodophenyl, 4-fluorophenyl. 4-chlorophenyl, 4-bromophenyl, 4-iodophenyl, 2,3-dichlorophenyl, 2,4-dichlorophenyl, 2,5-dichlorophenyl, 2,6-dichlorophenyl, 4-bromo-2-chlorophenyl, 4-iodo-2-chlorophenyl, 1-bromonaphthalen-2-yl, 2-chloronaphthalen-1-yl, 5-chloro-naphthalen-1-yl, 6-chloro-naphthalen-1-yl, 4-chloroisoquinolin-8-yl, 2-chloroquinolin-4-yl, 4-bromoisoquinolin-1-yl, 5-chloro-thiophen-2-yl, 5-bromothiophen-2-yl and 5-chlorothiophen-3-yl, etc.

The aromatic lower alkyl group means a lower alkyl group to which the above-described aromatic group is bonded, including benzyl, 1-phenylethyl, 2-phenylethyl, phenylpropyl, phenylbutyl, phenyl-pentyl, phenylhexyl, naphthylmethyl, naphthylethyl, naphthylpropyl, naphthylbutyl, naphthylpentyl, naphthylhexyl, pyridylmethyl, pyridylethyl, quinolylmethyl, isoquinolylmethyl, etc. The aromatic group may be substituted with a halogen atom or a group such as lower alkyl, halo-lower alkyl, nitro, lower alkoxycarbonyl, aromatic, aromatic lower alkyloxy, lower cycloalkyloxy-lower alkyl, aromatic lower alkyl, aromatic lower alkenyl, aromatic lower alkynyl, aromatic oxy-lower alkyl, lower cycloalkyl-lower alkyloxy, lower alkenyl, lower alkoxy, lower alkylthio, lower alkanesulfinyl, lower alkanesulfonyl, or lower alkanesulfonylcarbamoyl.

The lower alkyl aromatic group means the above-described aromatic group to which the above-described lower alkyl group is bonded, including 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-diethylphenyl, 3,5-dimethylphenyl, 2,3,5,6-tetramethylphenyl, pentamethylphenyl, 2-ethylphenyl, 3-ethylphenyl, 4-ethylphenyl, 2-n-propylphenyl, 2-i-propylphenyl, 3-n-propylphenyl, 3-i-propylphenyl, 4-n-propylphenyl, 4-i-propylphenyl, 2,4,6-tri-i-isopropylphenyl, 2-n-butylphenyl, 2-i-butylphenyl, 2-t-butylphenyl, 3-n-butylphenyl, 3-i-butylphenyl, 3-t-butylphenyl, 4-n-butylphenyl, 4-i-butylphenyl, 4-t-butylphenyl, 4-n-pentylphenyl, 4-i-pentylphenyl, 4-t-pentylphenyl, 4-n-hexylphenyl, 2-methylnaphthalen-1-yl, 3-methylnaphthalen-1-yl, 4-methyl-naphthalen-1-yl, 5-methylnaphthalen-1-yl, 6-methylnaphthalen-1-yl, 7-methylnaphthalen-1-yl, 8-methylnaphthalen-1-yl, 1-methyl-naphthalen-2-yl, 3-methylnaphthalen-2-yl, 4-methyinaphthalen-2-yl, 5-methyinaphthalen-2-yl, 6-methylnaphthalen-2-yl, 7-methyl-naphthalen-2-yl, 8-methylnaphthalen-2-yl, 5,8-dimethyl-naphthalen-1-yl, 5,8-dimethylnaphthalen-2-yl, etc.

The aromatic oxy lower alkyl group means the above-described aromatic group to which the above-described lower alkyl group is bonded via an oxygen atom, including (phenyloxy)methyl, (1-naphthyloxy)methyl, (2-naphthyloxy)methyl, 1-(phenyloxy)ethyl, 2-(phenyloxy) ethyl, 1-(1-naphthyloxy)ethyl, 1-(2-naphthyloxy)-ethyl, 2-(1-naphthyloxy)ethyl, 2-(2-naphthyloxy)ethyl, 1-(phenyloxy)propyl, 2-(phenyloxy)propyl, 3-(phenyloxy) propyl, 1-(1-naphthyloxy)propyl, 1-(2-naphthyloxy)propyl, 2-(1-naphthyl-oxy)propyl, 2-(2-naphthyloxy)propyl, 3-(1-naphthyloxy)propyl, 3-(2-naphthyloxy)propyl, 4-(phenyloxy)butyl, 5-(phenyloxy)pentyl, 6-(phenyloxy) hexyl, etc.

The aromatic lower alkyloxy group means the above-described aromatic group to which the above-described lower alkoxyl group is bonded, including benzyloxy, 1-naphthylmethyloxy, 2-naphthyl-methyloxy, (1-phenylethyl)oxy, (2-phenylethyl)oxy, (1-naphthyl-ethan-1-yl)oxy, (2-naphthylethan-1-yl)oxy, (1-naphthylethan-2-yl) oxy, (2-naphthylethan-2-yl)oxy, (1-phenylpropyl)oxy, (2-phenylpropyl)oxy, (3-phenylpropyl)oxy, (1-naphthylpropan-1-yl)oxy, (2-naphthylpropan-1-yl)oxy, (1-naphthylpropan-2-yl)oxy, (2-naphthylpropan-2-yl)oxy, (1-naphthylpropan-3-yl)oxy, (2-naphthylpropan-3-yl)oxy, (4-phenylbutyl)oxy, (2-naphthylbutan-4-yl)oxy, (5-phenylpentyl)oxy, (2-naphthylpentan-5-yl)oxy, (6-phenythexyl)oxy, (1-naphthylhexan-6-yl)oxy, etc.

The aromatic lower alkenyl group means the above-described lower alkenyl group to which the above-described aromatic group is bonded, including 1-phenylethenyl, 2-phenylethenyl, 1-phenyl-1-propenyl, 2-phenyl-1-propenyl, 3-phenyl-1-propenyl, 1-phenyl-2-propenyl, 2-phenyl-2-propenyl, 3-phenyl-2-propenyl, 1-phenyl-1-butenyl, 2-phenyl-1-butenyl, 4-phenyl-2-butenyl, 3-phenyl-2-propenyl, 2-phenyl-1-pentenyl, 2-phenyl-3-pentenyl, 2-phenyl-1-pentenyl, 2-phenyl-1-hexenyl, etc.

The lower alkenyl aromatic group means the above-described aromatic group to which an alkenyl group having 2 to 6 carbon atoms, including 2-vinylphenyl, 3-vinylphenyl, 4-vinylphenyl, 3-iso-propenylphenyl, 4-isopropenylphenyl, 4-allyphenyl, 4-(1-butenyl)phenyl, 4-(2-butenyl)phenyl, 4-(1,3-butanedienyl)phenyl, 4-(3-butenyl)phenyl, 4-(1-pentenyl)phenyl, 5-(1-hexenyl)phenyl, etc.

The aromatic lower alkynyl group means an alkynyl group having 2 to 6 carbon atoms to which the above-described aromatic group is bonded, including phenylethynyl, 3-phenyl-1-propynyl, 3-phenyl-1-butynyl, 4-phenyl-1-butynyl, 4-phenyl-2-butynyl, 1-phenyl-2-pentynyl, 1-phenyl-4-pentynyl, 6-phenyl-1-hexynyl, etc.

Preferred salts of the benzimidazole derivatives of the present invention are non-toxic, ordinary pharmaceutically acceptable salts thereof. For example, mentioned are salts of the derivatives with bases as well as acid-addition salts of the derivatives, which include, for example, salts thereof with inorganic bases, such as salts with alkali metals (e.g., sodium, potassium); salts with alkaline earth metals (e.g., calcium, magnesium); ammonium salts; salts with organic amines (e.g., triethylamine, pyridine, picoline, ethanolamine, triethanolamine, dicyclohexylamine, N,N'-dibenzylethylene-diamine); salts with inorganic acids (e.g., hydrochloric acid, hydrobromic acid, sulfuric acid, phosphoric acid); salts with organic carboxylic acids (e.g., formic acid, acetic acid, trifluoroacetic acid, maleic acid, tartaric acid); salts with sulfonic acids (e.g., methanesulfonic acid, benzenesulfonic acid, p-toluenesulfonic acid); salts with basic or acidic amino acids (e.g., arginine, aspartic acid, glutamic acid), etc.

The compounds of the invention could contain one or more chiral centers, therefore they could be enantiomers or diastereomers. Few of the compounds containing alkenyl group could also be cis- or trans- isomers. In both cases, each of such isomers as well as the mixture thereof are within the scope of this invention.

The compounds of the invention can also exist as tautomers, and individual of such tautmers and the mixture thereof are within the scope of this invention.

The compounds of the invention and their salts can be solvate, which are also within the invention. The solvent for the solvate is preferably hydrate or ethanol.

Specific examples of the compounds of the present invention include 1-(isoquinolin-3-ylmethyl)-2-methyl-6-(1-pentane-sulfonylcarbamoyl)benzimidazole, 1-((4-chloroisoquinolin-3-yl)-methyl)-2-methyl(1-pentanesulfonylcarbamoyl)benzimidazole, 1-((1-bromonaphthalen-2-yl)methyl)-2-methyl-6-(1-pentanesulfonyl-carbamoyl)benzimidazole, 1-(2,4-dichlorobenzyl)-6-((2-hydroxy-1-pentane)sulfonylcarbamoyl)-2-methylbenzimidazole, 1-(2,4-dichlorobenzyl)-6-((4-hydroxy-1-pentane)sulfonylcarbamoyl)-2-methylbenzimidazole, 1-(2,4-dichlorobenzyl)-6-((3-hydroxy-1-pentane)sulfonylcarbamoyl)-2-methylbenzimidazole, 1-(2,4-dichlorobenzyl)-2-methyl-6-(((E)-1-pent-1-en)sulfonylcarbamoyl)-benzimidazole, 6-(benzenesulfonylcarbamoyl)-1-(2,4-dichloro-benzyl)-2-methylbenzimidazole, 6-(N'-butanesulfonylhydrazinocarbonyl)-1-(2,4-dichlorobenzyl)-2-methylbenzimidazole, 6-((n-butylaminosulfonyl)carbamoyi)-1-(2,4-dichlorobenzyl)-2-methyl-benzimidazole, 1-(2,4-dichlorobenzyl)-2-methyl-6-[N'-(4-methyl-phenylsulfonyl)ureido]benzimidazole, 1-(2,4-dichlorobenzyl)-2-methyl-6-(N'-phenylureido)benzimidazole, 1-(2-chloro-4-(trifluoromethyl)benzyl)-2-methyl-6-(1-pentanesulfonyl-carbamoyl)benzimidazole, 1-(2-chloro-4-(trifluoromethyl)benzyl)-2-methyl-6-(((E)-1-pent-1-en)sulfonylcarbamoyl)benzimidazole, 1-(2,4-dichlorobenzyl)-2-methyl-6-((E)-2-phenylethenylsulfonyl-carbamoyl)benzimidazole, 1-(2-chloro-4-phenylbenzyl)-2-methyl-6-(1-pentanesulfonylcarbamoyl)benzimidazole, 1-(2-chloro-4-phenyl-benzyl)-2-methyl-6-(((E)-1-pent-1-en)sulfonylcarbamoyl)-benzimidazole, 1-(2-chloro-4-phenylbenzyl)-2-methyl-6-((4-methylbenzene)sulfonylcarbamoyl)benzimidazole, 1-(2-chloro-4-phenylbenzyl)-2 -methyl-6-((E)-2-phenylethenylsulfonylcarbarmoyl)-benzimidazole, 1-(2-chloro-4-phenylbenzyl)-6-((5-chlorothiophen-2-yl)sulfonylcarbamoyl)-2-methylbenzimidazole, 1-(4-bromo-2-chlorobenzyl)-2-methyl-6-(((E)-1-pent-1-en)sulfonylcarbamoyl)-benzinidazole, 1-(4-bromo-2-chlorobenzyl)-2-methyl-6-((4-methyl-benzene)sulfonylcarbamoyl)benzimidazole, 1-(4-bromo-2-chlorobenzyl)-2-methyl-6-((E)-2-phenylethenylsulfonylcarbamoyl)-benzimidazole, 1-(4-bromo-2-chlorobenzyl)-6-((5-chlorothiophen-2-yl)sulfonylcarbamoyl)-2-methylbenzimidazole, 1-(4-benzyloxy-2-chlorobenzyl)-2-methyl-6-(1-pentanesulfonylcarbamoyl)-benzimidazole, 1-(4-benzyloxy-2-chlorobenzyl)2-methyl-6-((4-methylbenzene)sulfonylcarbamoyl)benzimidazole, 6-((5-bromothio-phen-2-yl)sulfonylcarbamoyl)-1-(2,4-dichlorobenzyl)-2-methyl-benzimidazole, 6-((5-bromothiophen-2-yl)sulfonylcarbamoyl)-1-(2-chloro-4-phenylbenzyl)-2-methylbenzimidazole, 1-(2-chloro-4-(cyclohexylmethyloxy)benzyl)-2-methyl-6-(1-pentanesulfonyl-carbamoyl)benzimidazole, 1-(2-chloro-4-(cyclohexylmethyloxy)-benzyl)-2-methyl-6-((4-methylbenzene)sulfonylcarbamoyl)-benzimidazole, 6-((5-chlorothiophen-2-yl)sulfonylcarbamoyl)-1-(2,4-dichlorobenzyl)-2-methylbenzimidazole, 1-(4-bromo-2-chloro-benzyl)-6-((5-bromothiophen-1-yl)sulfonylcarbamoyl)-2-methyl-benzimidazole, 1-(2,4-dichlorobenzyl)-2-methyl-6-((4-vinyl-benzene)sulfonylcarbamoyl)benzimidazole, 1-(2-chloro-4-bromo-benzyl)-2-methyl-6-((4-vinylbenzene)sulfonylcarbamoyl)-benzimidazole, 1-(2-chloro-4-phenylbenzyl)-2-methyl-6-((4-vinyl-benzene)sulfonylcarbamoyl)benzimidole. 1-(2,4-dichlorobenzyl)-2-methyl-6-((4-methylbenzene)sulfonylcarbamoyl)benzimidazole, (+)-1-(1-(2,4-dichlorophenyl)ethyl)-2-methyl-6-(1-pentane-sulfonylcarbamoyl)benzimidazole, (−)-1-(1-(2,4-dichlorophenyl)-ethyl)-2-methyl-6-(1-pentanesulfonylcarbamoyl)benzimidazole, 1-(4-bromo-2-chlorobenzyl)-2-methyl-6-((1-pent-4-en)sulfonyl-carbarnoyl)benzimidazole, 1-(2-chloro-4-phenylbenzyl)-2-methyl-6-(((E)-1-pent-4-en)sulfonylcarbamoyl)benzimidazole, 1-(2-chloro-4-nitrobenzyl)-2-methyl-6-(1-pentanesulfonylcarbamoyl)-benzimidazole, 1-(2-chloro-4-phenylethynylbenzyl)-2-methyl-6-(1-pentanesulfonylcarbamoyl)benzimidazole, 1-(2-chloro-4-((E)-2-phenylethenyl)benzyl)-2-methyl-6-(1-pentanesulfonylcarbamoyl)-benzimidazole, 1-(2-chloro-4-((E)-2-phenylethenyl)benzyl)-2-methyl-6-((4-methylbenzene)sulfonylcarbamoyl)benzimidazole, 1-(2-chloro-4-(1-hexen-1-yl)benzyl)-2-methyl-6-(1-pentanesulfonyl-carbamoyl)benzimidazole, 1-(2-chloro-(1-hexen-1-yl)benzyl)-2-methyl-6-((4-methylbenzene)sulfonylcarbamoyl)benzimidazole, 1-(2-chloro-4-(2-phenylethyl)benzyl)-2-methyl-6-(1-pentane-sulfonylcarbamoyl)benzimidazole, 1-(4-t-butylthio-2-chloro-benzyl)-2-methyl-6-(1-pentanesulfonylcarbamoyl)benzimidazole, 1-(4-t-butylthio-2-chlorobenzyl)-2-methyl-6-((4-methylbenzene)-sulfonylcarbamoyl)benzimidazole, 1-(2-chloro-4-(phenoxymethyl)-benzyl)-2-methyl-6-(1-pentanesulfonylcarbamoyl)benzimidazole, 1-(2-chloro-4-(phenoxymethyl)benzyl)-2-methyl-6-((4-methyl-benzene)sulfonylcarbamoyl)benzimidazole, 1-(2-chloro-4-(cyclohexyloxymethyl)benzyl)-2-methyl-6-(1-pentanesulfonylcarbamoyl)-benzimidazole, 1-(2-chloro-4-(cyclohexyloxymethyl)benzyl)-2-methyl-6-((4-methylbenzene)sulfonylcarbamoyl) benzimidazole, 1-(2-chlorphenylbenzyl)-2-methyl-6-((n-pentylaminosulfonyl)-carbamoyl)benzimidazole, 1-(2,4-chlorobenzyl)-2-methyl(((4-methylphenyl)aminosulfonyl)carbamoyl)benzimidazole, 1-(2-chloro-4-phenylbenzyl)-2-methyl-6-(((4-methylphenyl)amino-sulfonyl)carbamoyl)benzimidazole, 1-(2-chloro-4-iodobenzyl)-2-methyl-6-(1- pentanesulfonylcarbamoyl)benzimidazole, 1-(2-chloro-4-iodobnzyl)-2-methyl-6-((4-methylbenzene) sulfonylcarbamoyl)-benzimidazole, 1-(2-chloro-4-ethoxybenzyl)-2-methyl-6-(1-pentanesulfonylcarbamoyl) benzimidazole, 1-(2-chloro-4-ethoxy-benzyl)-2-methyl-6-((4-methylbenzene)sulfonylcarbamoyl)-benzimidazole, 1-(2-chloro-4-(1-pentanesulfonylcarbamoyl)-benzyl)-2-methyl-6-(1-pentanesulfonylcarbamoyl)benzimidazole, 1-(4-bromo-2-chlorobenzyl)-2-methyl-6-(1-pentanesulfonyl-carbamoyl)benzimidazole, 1-(2-chloro-4-(trifluoromethyl)-benzyl)-2-methyl-6-(4-methylbenzene) sulfonylcarbamoyl)-benzimindazole, 1-(2-chloro-4-(trifluoromethyl)benzyl)-2-methyl-6-((4-vinylbenzene) sulfonylcarbamoyl)benzimidazole, (R)-1-(2,4-dichlorobenzyl)-6-((4-hydroxy-1-pentane) sulfonylcarbamoyl)-2-methylbenzimidazole, (S)-1-(2,4-dichlorobenzyl)-6-((4-hydroxy-1-pentane) sulfonylcarbamoyl)-2-methylbenzimidazole, optically active 1-(2,4-dichlorobenzyl)-6-((2-hydroxy-1-pentane) sulfonyl-carbamoyl)-2-methylbenzimidazole (showing longer retention time by liquid chromatography), optically active 1-(2,4-dichlorobenzyl)-6-((2-hydroxy-1-pentane) sulfonylcarbamoyl)-2-methylbenzimidazole (showing shorter retention time by liquid chromatography), optically active 1-(2,4-dichlorobenzyl)-6-((3-hydroxy-1-pentane) sulfonyl-carbamoyl)-2-methylbenzimidazole (showing longer retention time by liquid chromatography), optically active 1-(2,4-dichlorobenzyl)-6-((3-hydroxy-1-pentane) sulfonylcarbamoyl)-2-methyl-benzimidazole (showing shorter retention time by liquid chromatography), 1-(2-chloro-4-(1-hexyl)benzyl)-2-methyl-((4-methylbenzene) sulfonylcarbamoyl)benzimidazole, 1-(2-chloro-4-(1-hexyl) benzyl)-2-methyl-6(pentanesulfonylcarbamoyl)-benzimidazole, 1-(2-chloro-4-(thiophen-2-yl)benzyl)-2-methyl-6-((4-methylbenzene)sulfonylcarbamoyl) benzimidazole, 1-(2-chloro-4-(thiophen-2-yl)benzyl)-2-methyl-6-(1-pentanesulfonyl-carbamoyl)benzimidazole, 1-(2-chloro-4-(furan-2-yl)benzyl)-2-methyl-6-(1-pentanesulfonylcarbamoyl)benzimidazole, 1-(2-chloro-4-(furan-2-yl)benzyl)-2-methyl-6-((4-methylbenzene) sulfonyl-carbamoyl)benzimidazole, 1-(2-chloro-4-(phenylethynyl)benzyl)-2-methyl-6-((4-methylbenzene) sulfonylcarbamoyl)benzimidazole, 1-(2-chloro-4-(2-phenylethynyl)benzyl)-2-methyl-6-((E)-1-pentene-1-sulfonylcarbamoyl)benzimidazole, 1-(2-chloro-4-(phenylethynyl)benzyl)-2-methyl-6-((4-vinylbenzene) sulfonylcarbamoyl)-benzimidazole, 1-(2-chloro-4-phenylethynyl)benzyl)-2-methyl-6-((E)-2-phenylethenylsulfonylcarbamoyl)benzimidazole, 1-(2-chloro-4-((E)-2-phenylethenyl)benzyl)-6-((4-vinylbenzene)-sulfonylcarbamoyl)-2-methylbenzimidazole, 1-(2-chloro-4-((E)-2-phenylethenyl)benzyl)-6-((E)-1-pentene-1-sulfonylcarbamoyl)-2-methylbenzimidazole, 1-(2-chloro-4-((E)-2-phenylethenyl)benzyl)-2-methyl-6-((E)-2-phenylethenylsulfonylcarbamoyl) benzimidazole, 1-(4-butyloxy-2-chlorobenzyl)-6-(1-pentanesulfonylcarbamoyl)-2-methylbenzimidazole, 1-(2-chloro-4-(3-methylbutoxy)benzyl)-2-methyl-6-(1-pentanesulfonylcarbamoyl)benzimidazole, 1-(2-chloro-4-(3-methylbutoxy)benzyl)-2-methyl-6-((4-methylbenzene) sulfonyl-carbamoyl)benzimidazole, etc.

The benzimidazole derivatives and their pharmaceutically acceptable salts of the present invention that are mentioned hereinabove are effective for preventing and treating various disorders, for example, impaired glucose tolerance, diabetes (type II diabetes), diabetic complications (e.g., diabetic gangrene, diabetic arthropathy, diabetic osteopenia, diabetic glomerulosclerosis, diabetic nephropathy, diabetic dernatopathy, diabetic neuropathy, diabetic cataract, diabetic retinopathy, etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia (e.g., abnormal saccharometabolism such as feeding disorders, etc.), and hypertension based on their blood sugar level-depressing activity, as well as stenocardia, hypertension, pulmonary hypertension, congestive heart failure, glomerulopathy (e.g., diabetic glomerulosclerosis etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), autoimmune diseases, allergic rhinitis, urticaria, glaucoma, diseases characterized by enteromotility disorders (e.g., hypersensitive enteropathy syndrome, etc.), impotence (e.g., organic impotence, psychic impotence, etc.), and diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy, etc.), nephritis, cachexia (e.g., progressive weight loss dLe to the lipolysis, myolysis, anemia, edema, anorexia, etc. associated with chronic diseases such as cancer, tuberculosis, endocrine disorder, AIDS, etc.), pancreatitis, and restenosis after PTCA based on their cGMP-PDE (especially PDE-V)-inhibiting activity, smooth muscle relaxing activity, bronchodilating activity, vasodilating activity, smooth muscle cell suppressing activity, and antiallergic activity.

To use the benzimidazole derivatives of the present invention for treating diseases or disorders such as those mentioned hereinabove, they may be formulated into pharmaceutical compositions of ordinary forms, which comprise, as an active ingredient, any of the derivatives along with pharmaceutically acceptable carriers, such as organic or inorganic solid or liquid vehicles, and which are suitable for oral administration, parenteral administration or external application. The pharmaceutical compositions may be of any solid form of tablets, granules, powders, capsules, etc., or may be of any liquid form of solutions, suspensions, syrups, emulsions, lemonades, etc.

If desired, the pharmaceutical compositions may further contain a pharmaceutical aid, a stabilizer, a wetting agent, and also any ordinary additive of, for example, lactose, citric acid, tartaric acid, stearic acid, magnesium stearate, terra alba, sucrose, corn starch, talc, gelatin, agar, pectin, peanut oil, olive oil, cacao butter, ethylene glycol, etc.

The amount of the above-mentioned derivative of the present invention to be used shall vary, depending on the age and the condition of patients, the type and the condition of diseases or disorders, and the type of the derivative to be used. In general, for oral administration, the dose of the derivative may be from 1 to 100 mg/kg; and for intramuscular injection or intravenous injection, it may be from 0.1 to 10 mg/kg. Such a unit dose may be applied to a patient once to four times a day.

BRIEF DESCRIPTION OF THE DRAWINGS

FIG. 10 shows chemical formulae of compound (53) to compound (56).

BEST MODE FOR CARRYING OUT THE INVENTION

Figure 1:
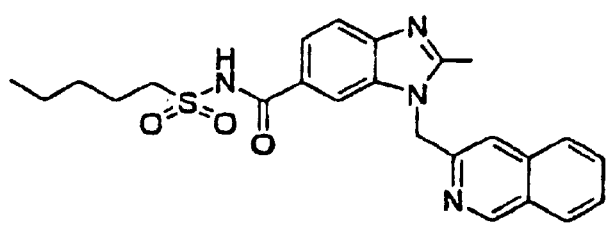
FIG. 1 shows chemical formulae of compound (13) to compound (16).
Figure 1:
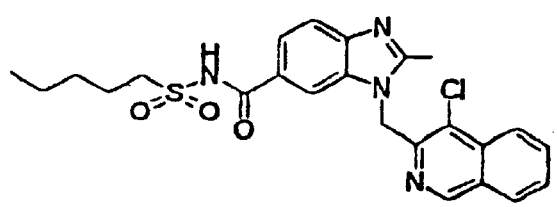
Figure 1:
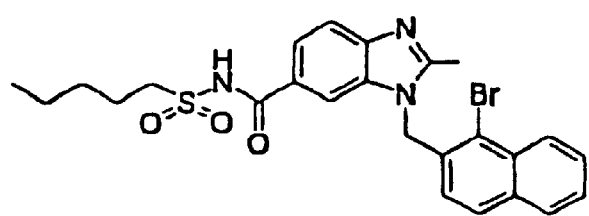
Figure 1:
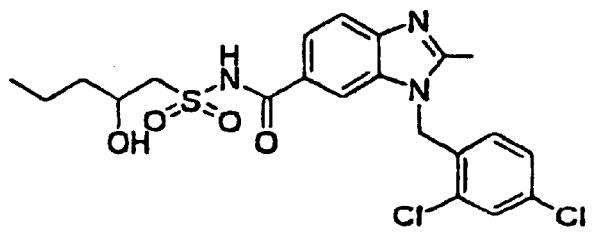
Figure 2:
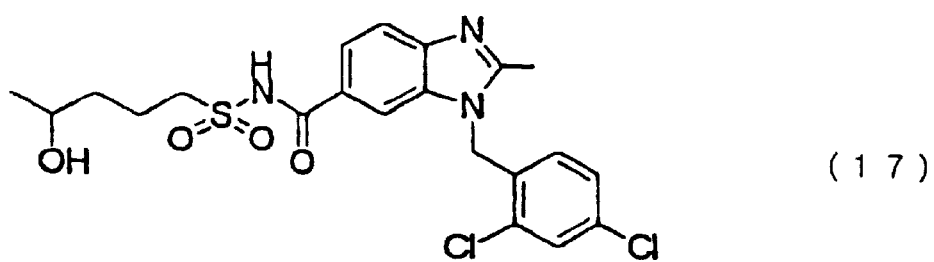
FIG. 2 shows chemical formulae of compound (17) to compound (20).
Figure 2:
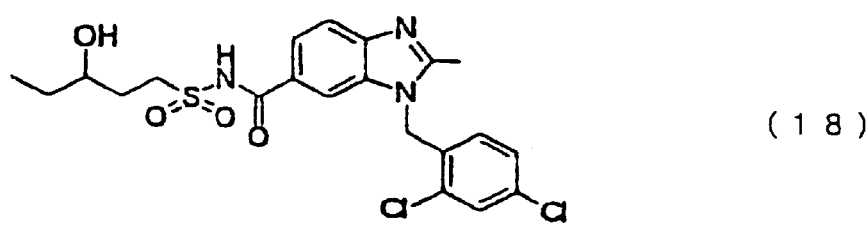
Figure 2:
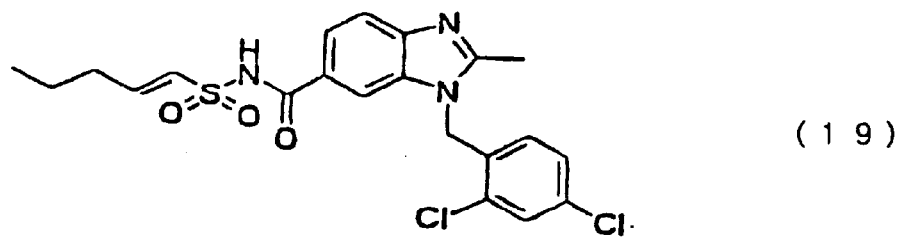
Figure 2:
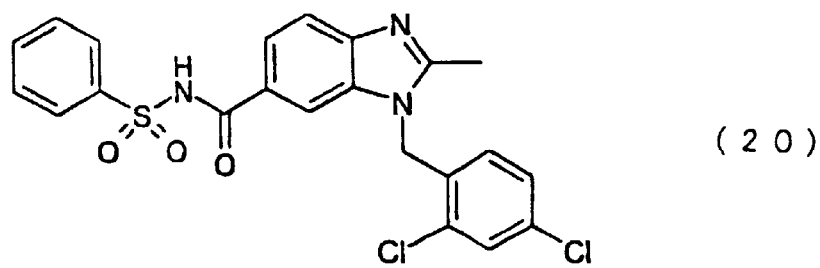
Figure 3:
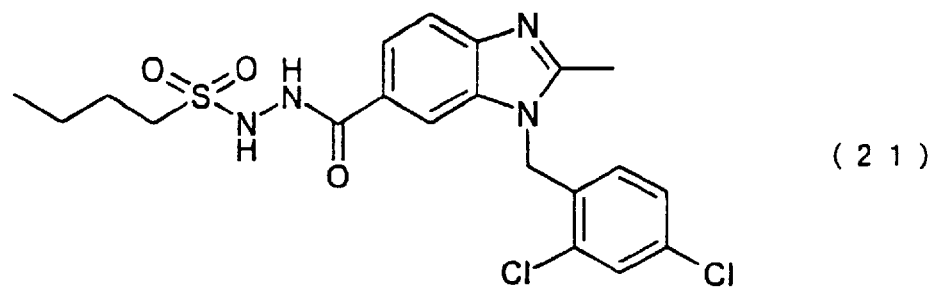
FIG. 3 shows chemical formulae of compound (21) to compound (24).
Figure 3:
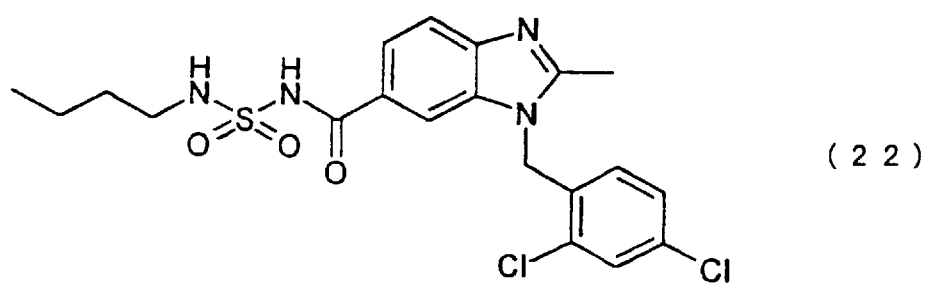
Figure 3:
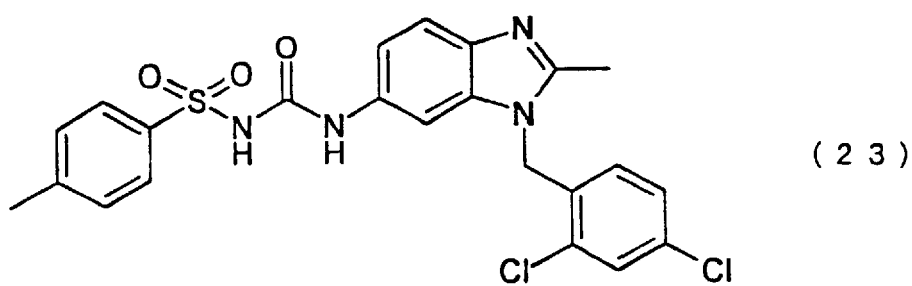
Figure 3:
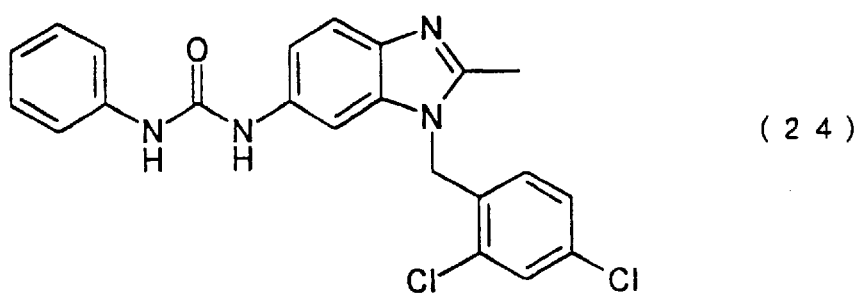
Figure 4:
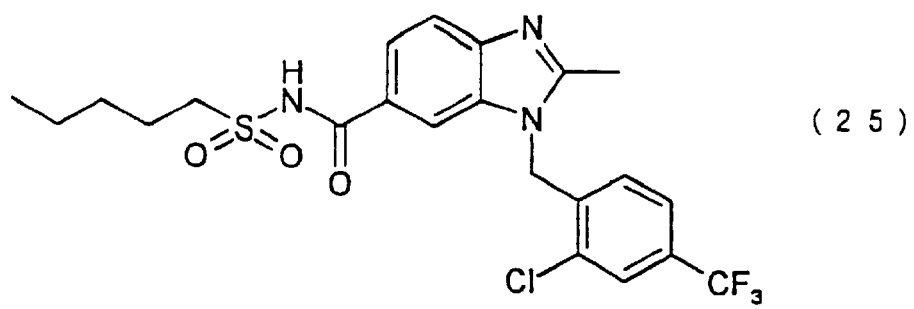
FIG. 4 shows chemical formulae of compound (25) to compound (28).
Figure 4:
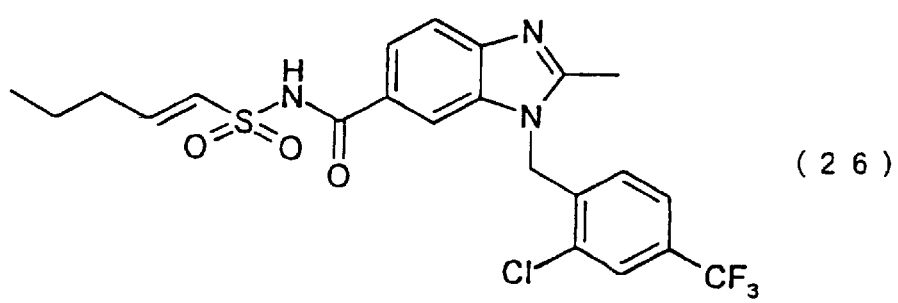
Figure 4:
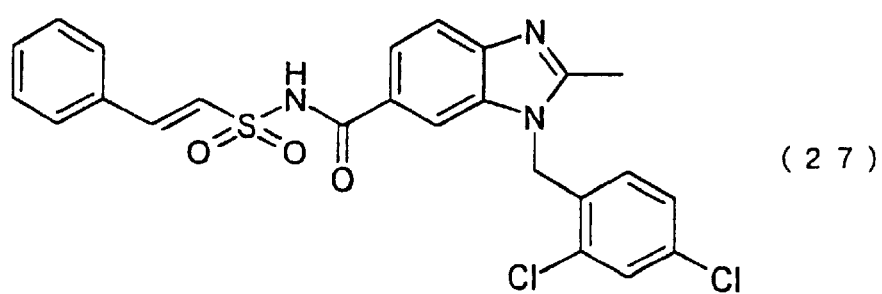
Figure 4:
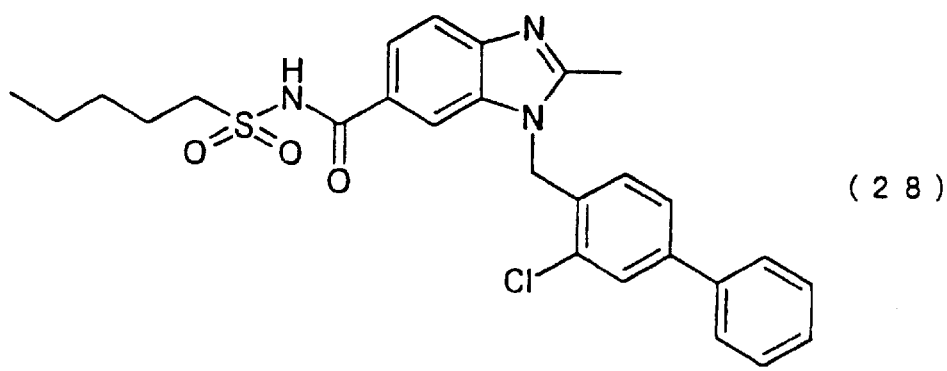
Figure 5:
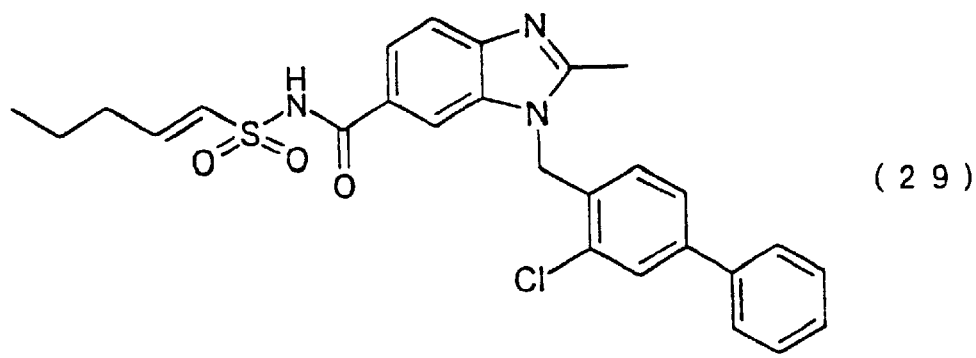
FIG. 5 shows chemical formulae of compound (29) to compound (32).
Figure 5:
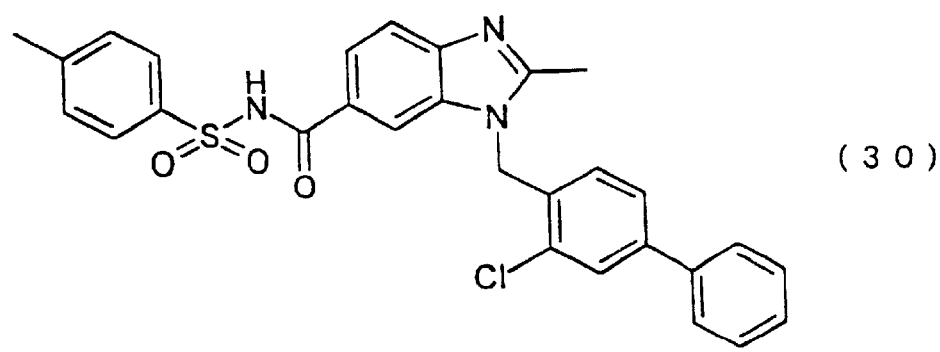
Figure 5:
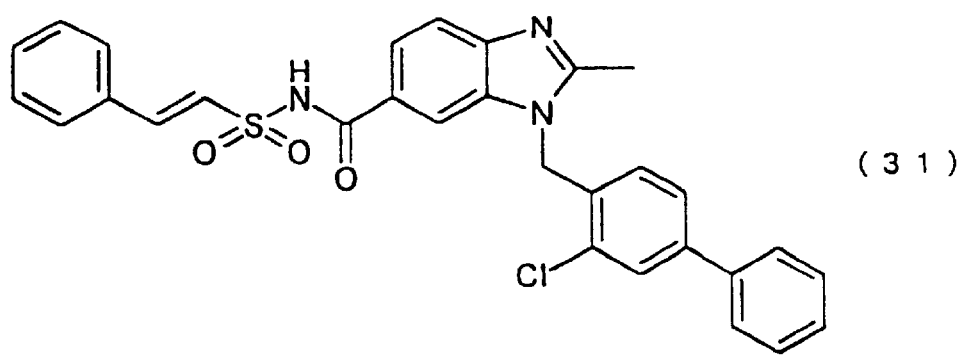
Figure 5:
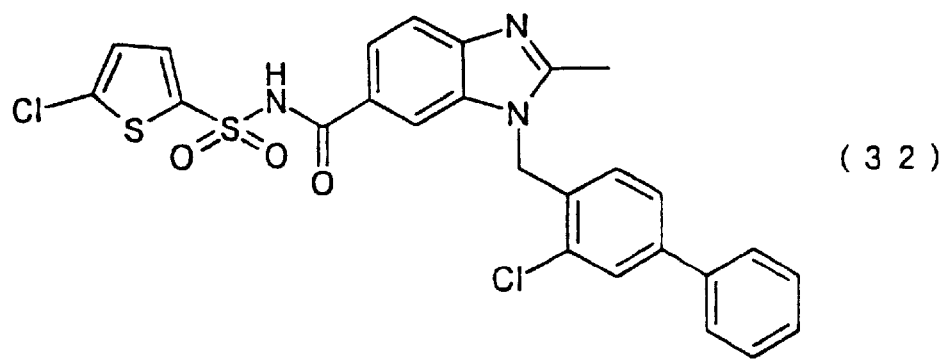
Figure 6:
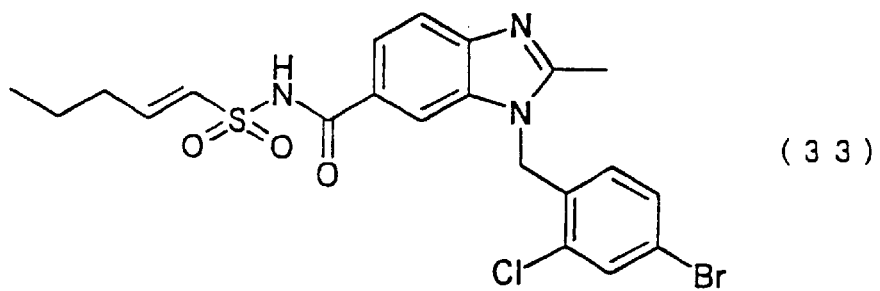
FIG. 6 shows chemical formulae of compound (33) to compound (36).
Figure 6:
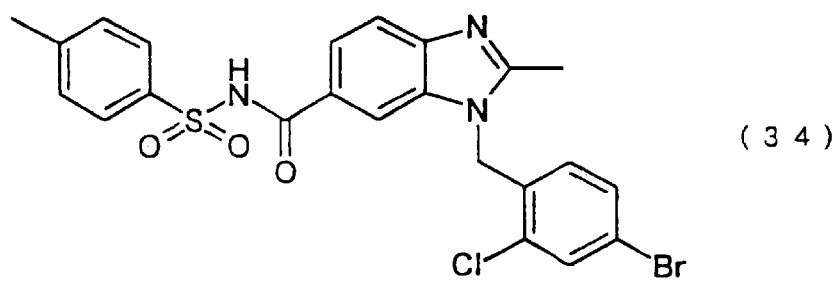
Figure 6:
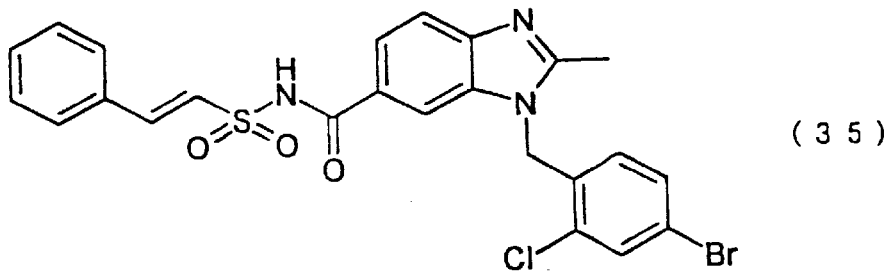
Figure 6:
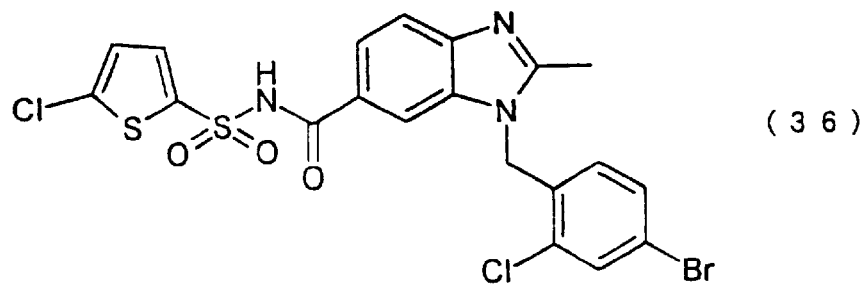
Figure 7:
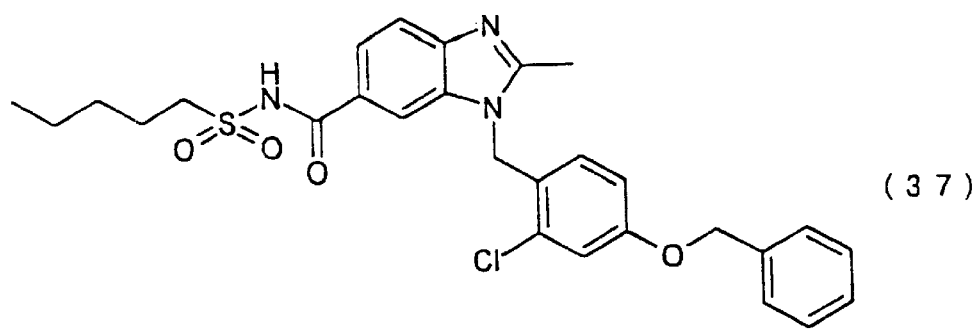
FIG. 7 shows chemical formulae of compound (37) to compound (40).
Figure 7:
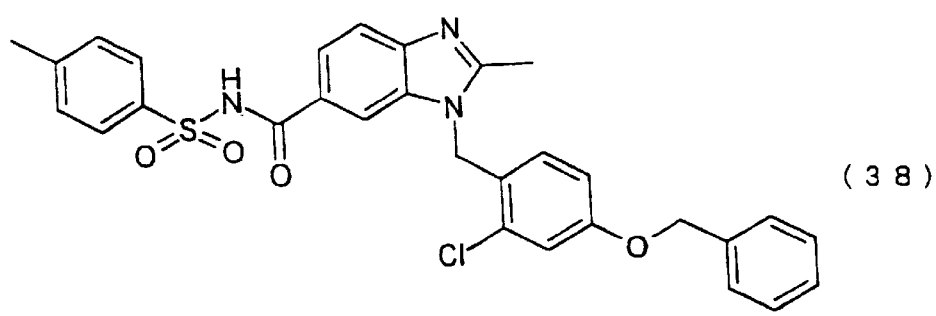
Figure 7:
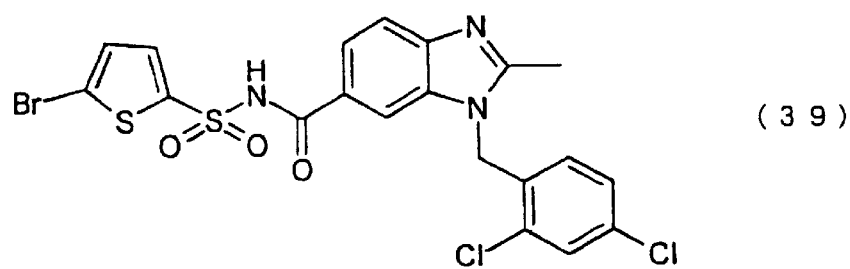
Figure 7:
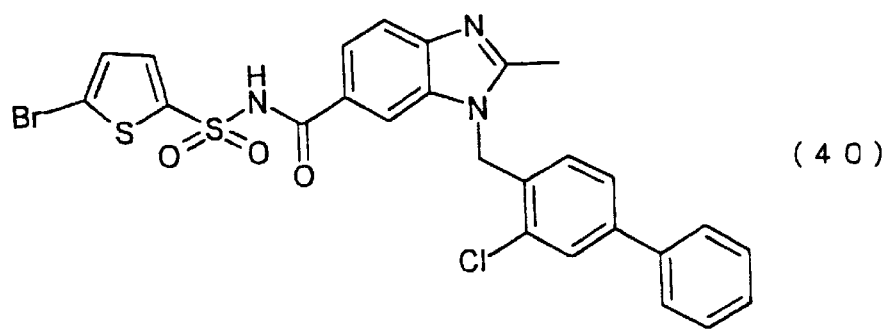
Figure 8:
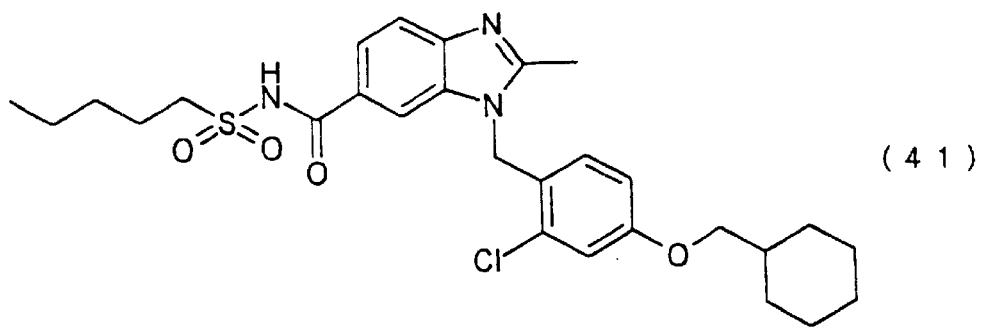
FIG. 8 shows chemical formulae of compound (41) to compound (44).
Figure 8:
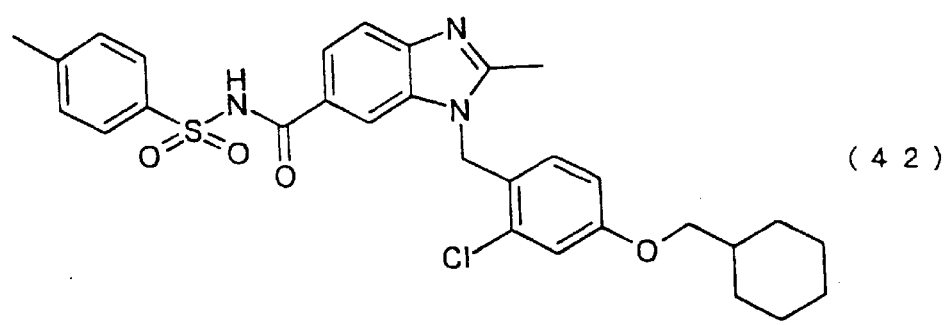
Figure 8:
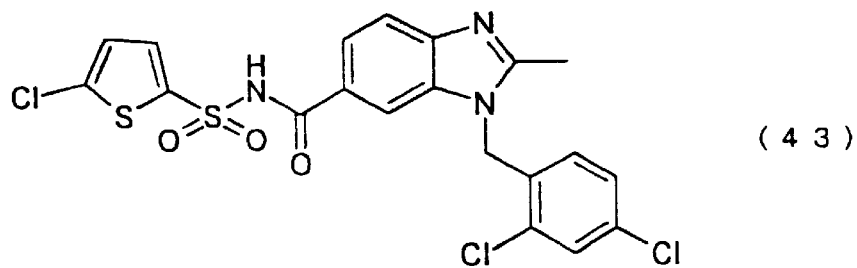
Figure 8:
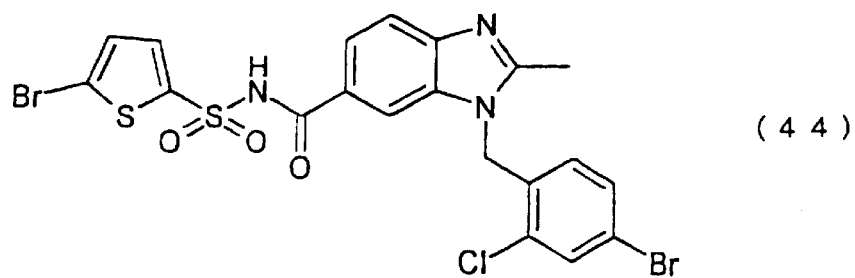
Figure 9:
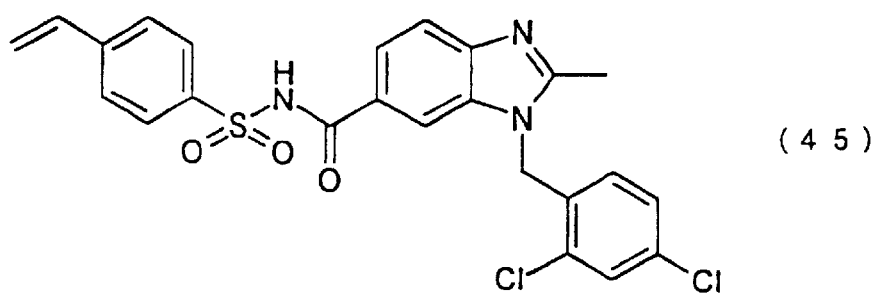
FIG. 9 shows chemical formulae of compound (45) to compound (48).
Figure 9:
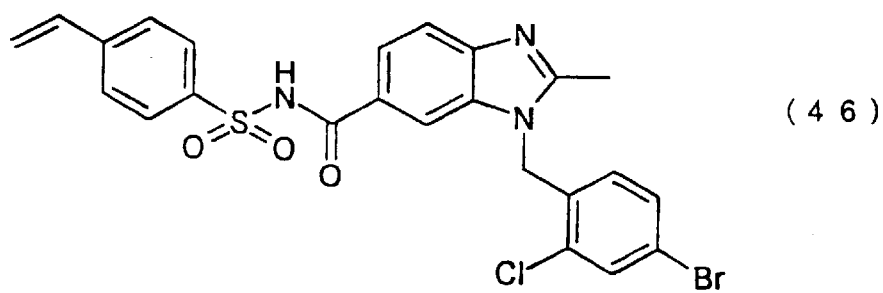
Figure 9:
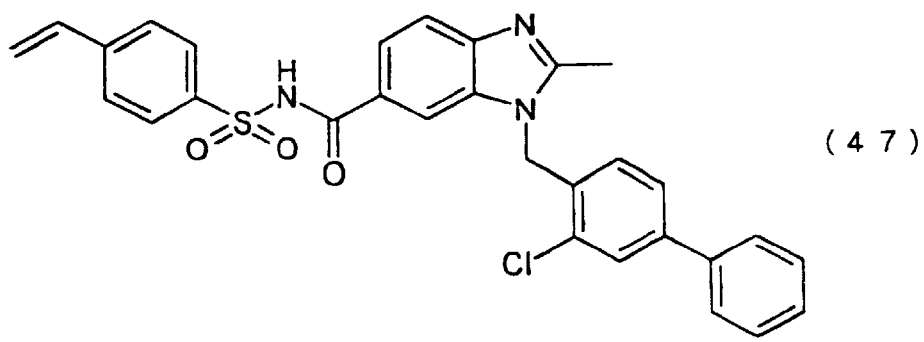
Figure 9:
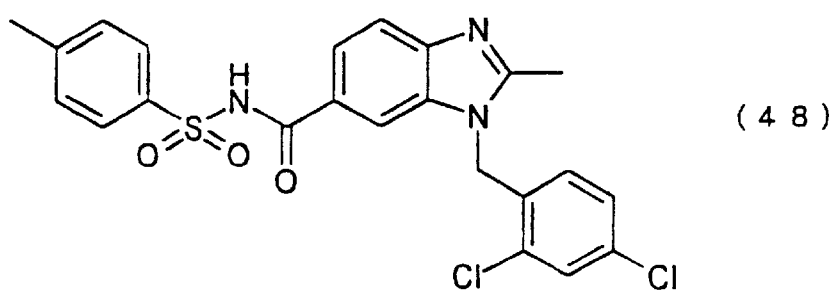
Figure 10:
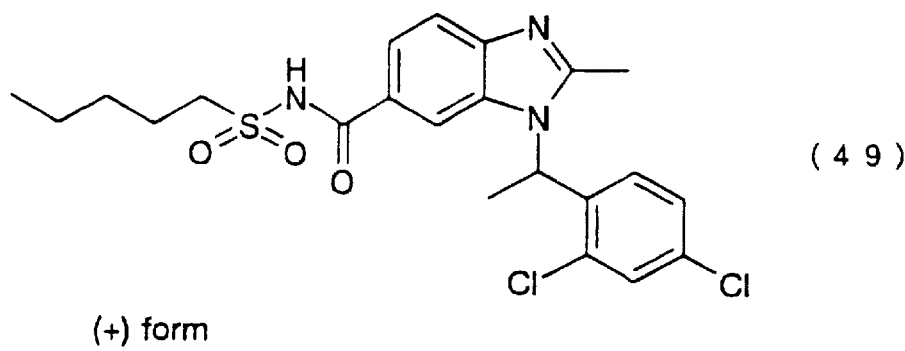
FIG. 10 shows chemical formulae of compound (49) to compound (52).
Figure 10:
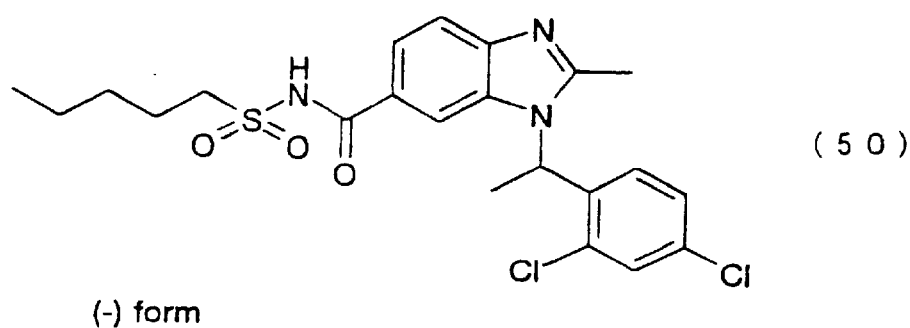
Figure 10:
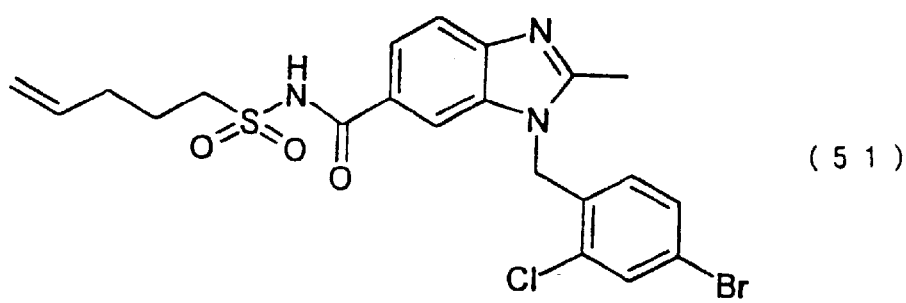
Figure 10:
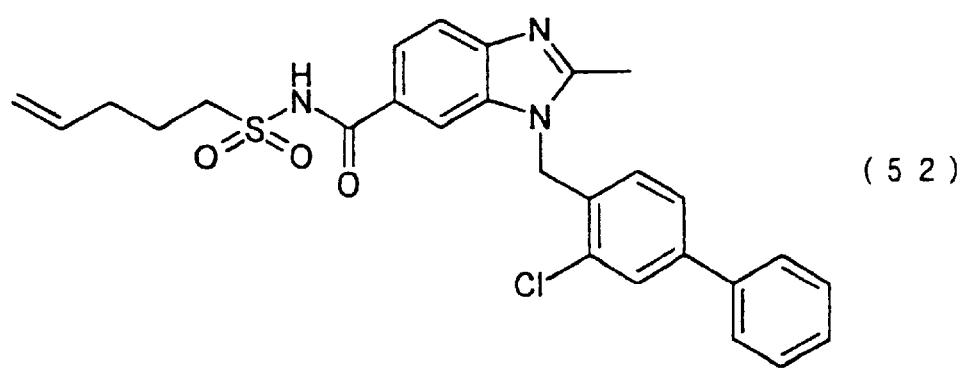
Figure 11:
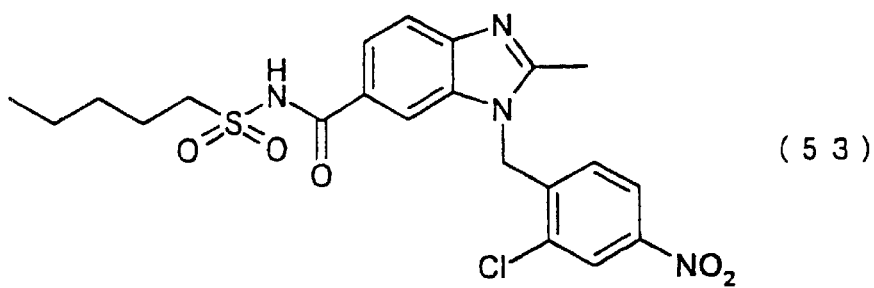
Figure 11:
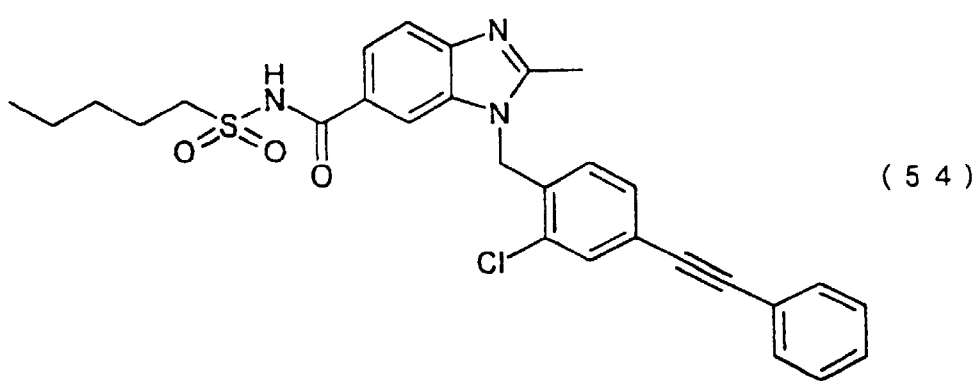
Figure 11:
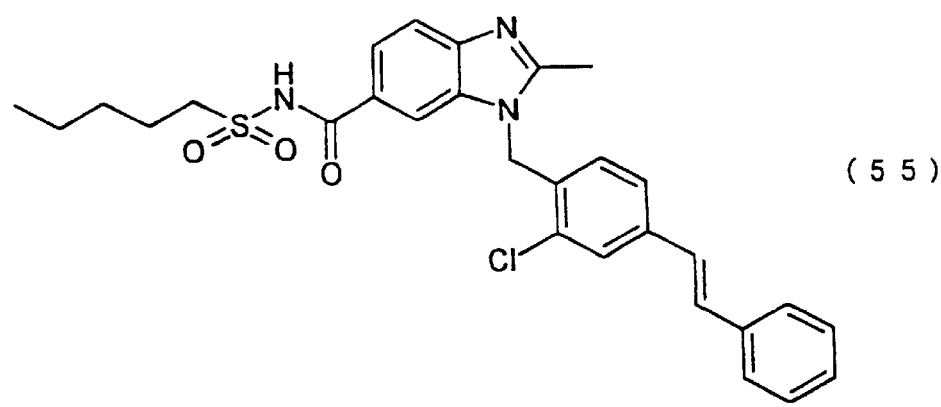
Figure 11:
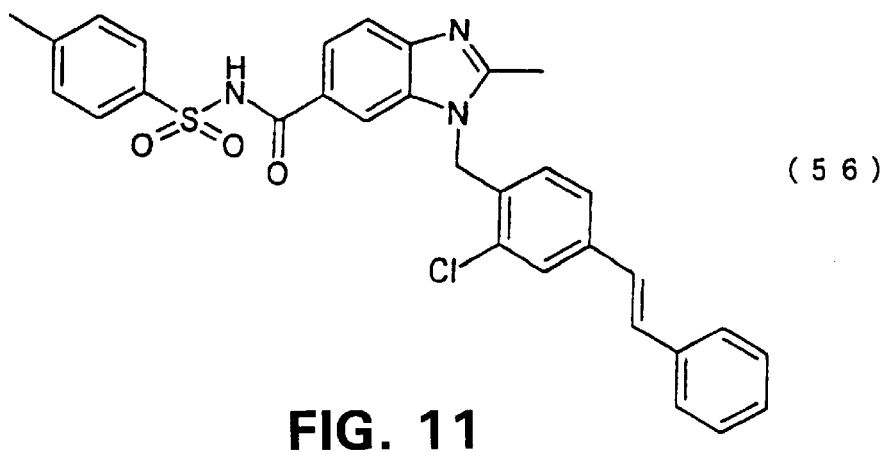
Figure 12:
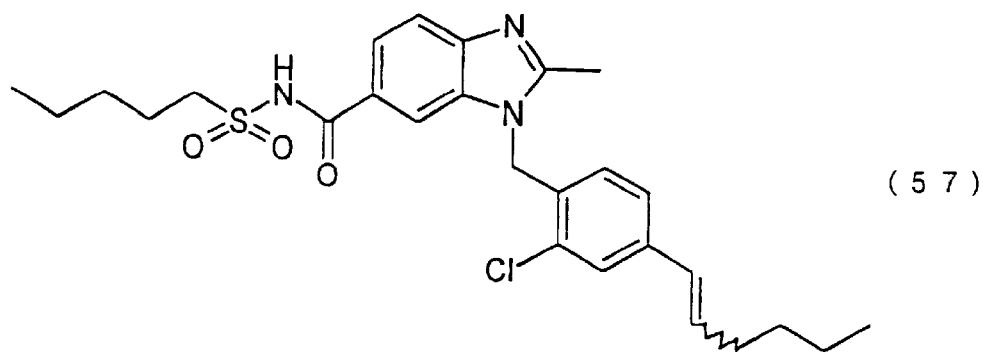
FIG. 12 shows chemical formulae of compound (57) to compound (60).
Figure 12:
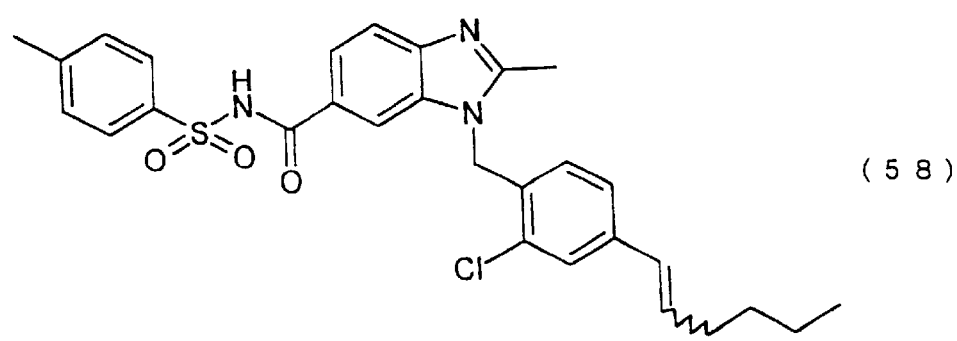
Figure 12:
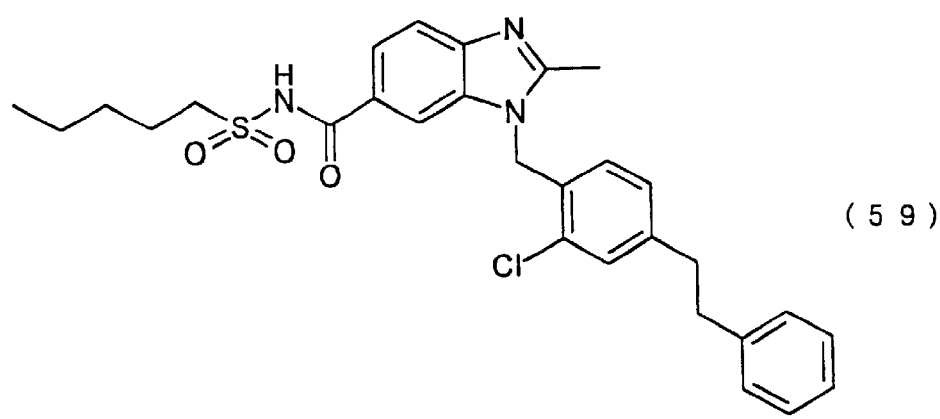
Figure 12:
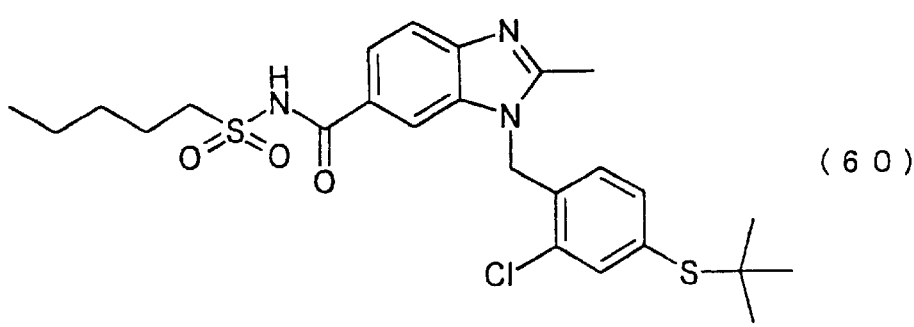
Figure 13:
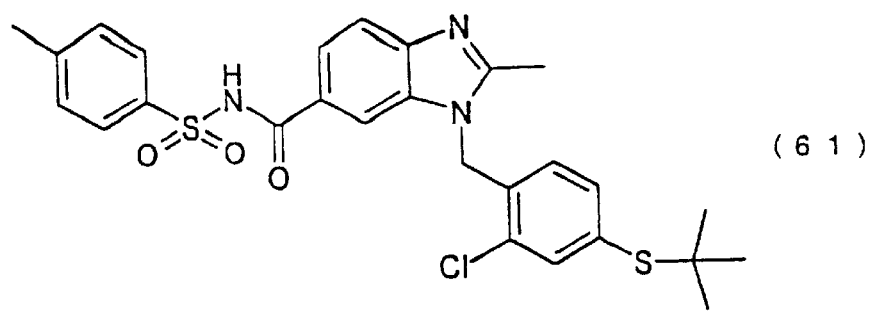
FIG. 13 shows chemical formulae of compound (61) to compound (64).
Figure 13:
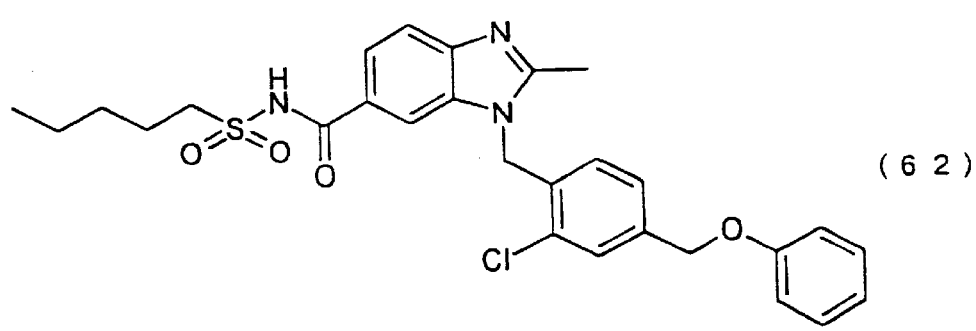
Figure 13:
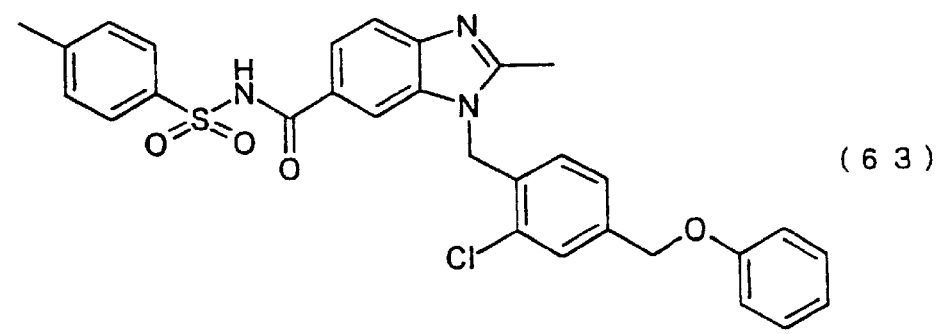
Figure 13:
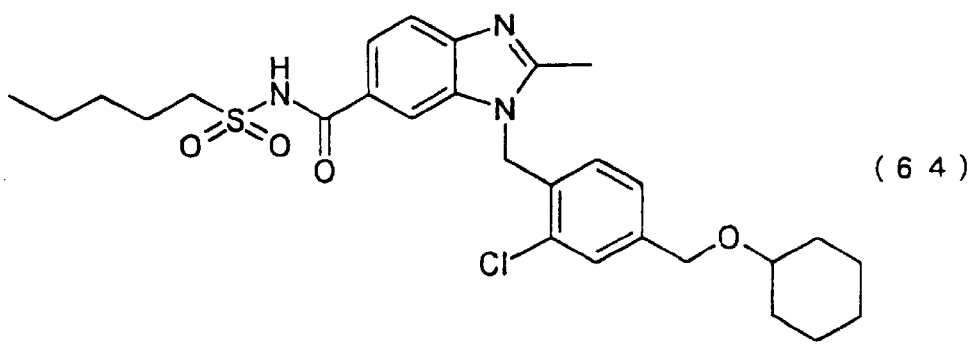
Figure 14:
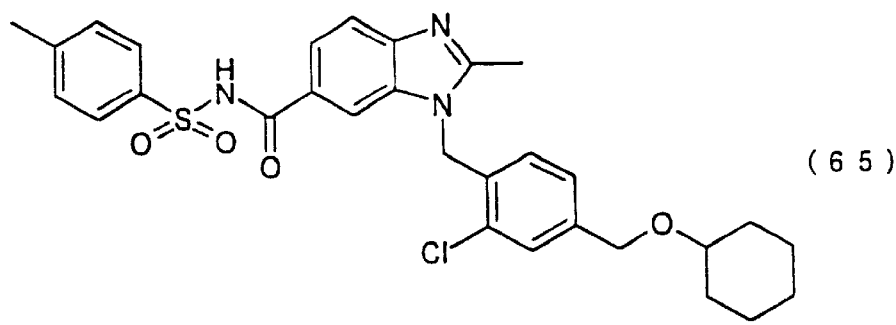
FIG. 14 shows chemical formulae of compound (65) to compound (68).
Figure 14:
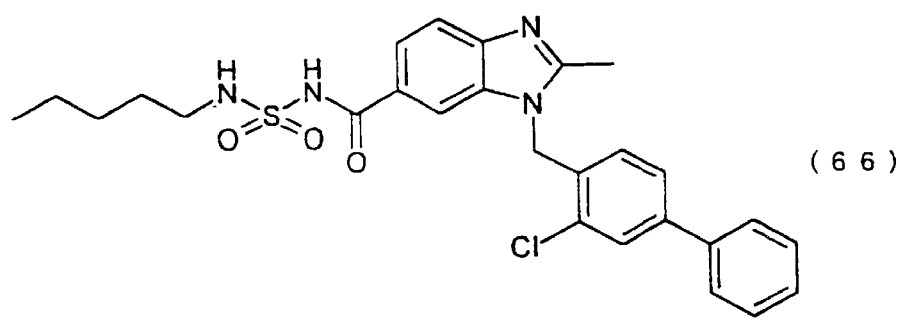
Figure 14:
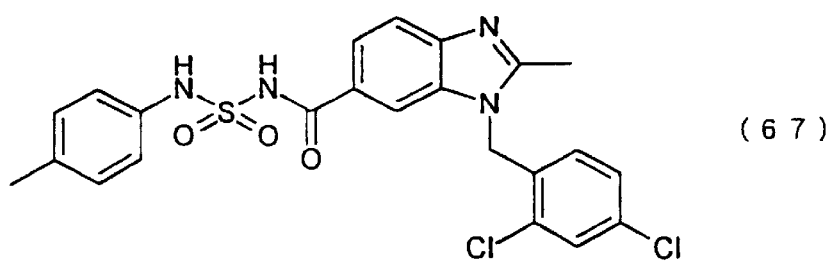
Figure 14:
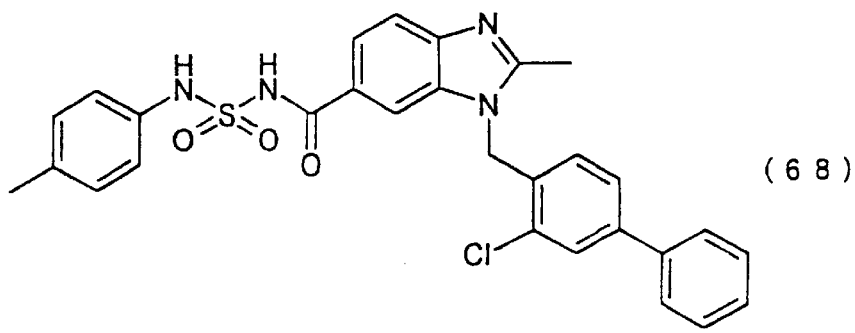
Figure 15:
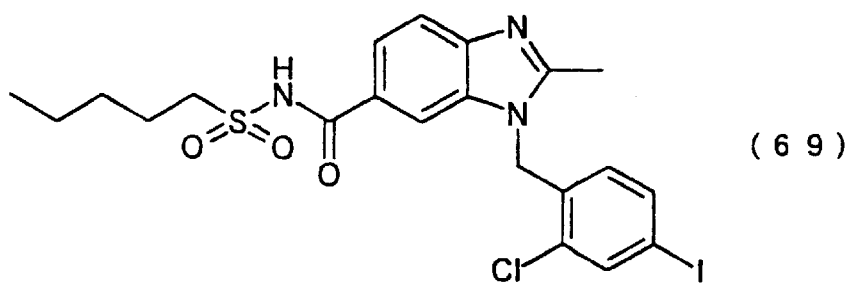
FIG. 15 shows chemical formulae of compound (69) to compound (72).
Figure 15:
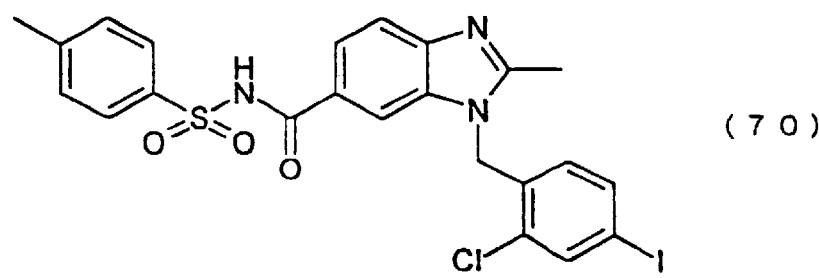
Figure 15:
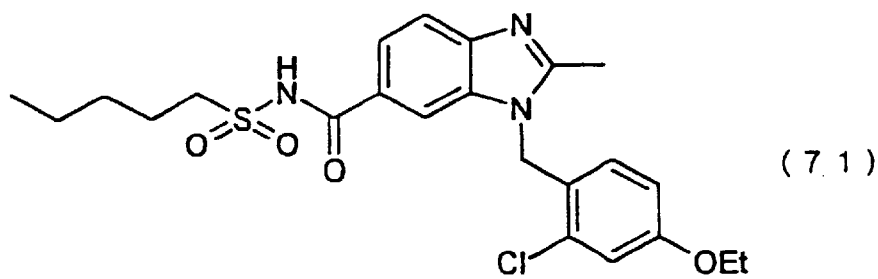
Figure 15:
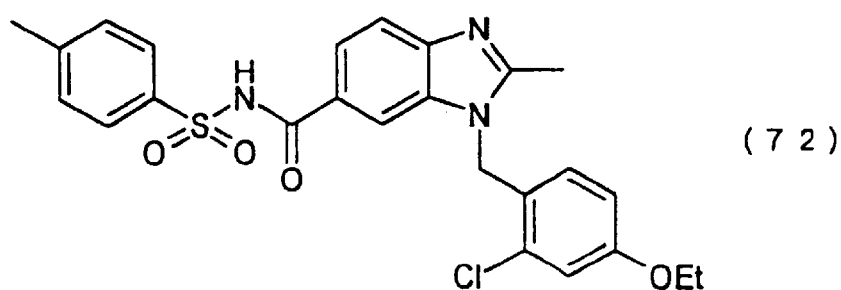
Figure 16:
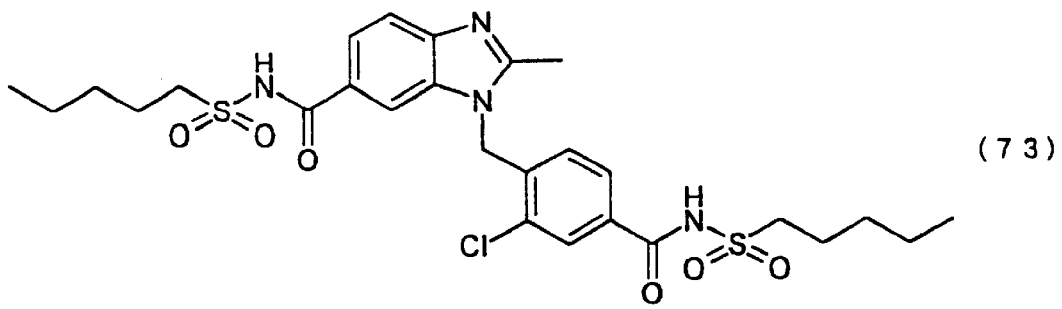
FIG. 16 shows chemical formulae of compound (73) to compound (76).
Figure 16:
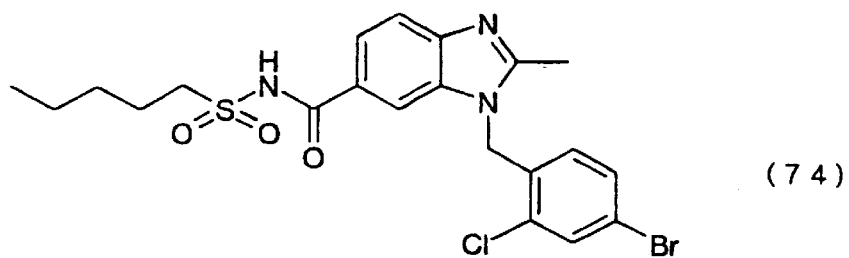
Figure 16:
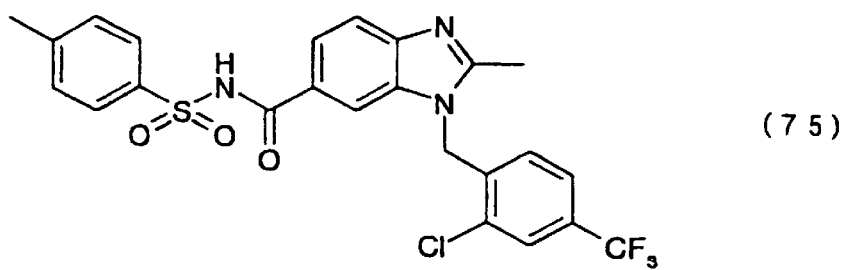
Figure 16:
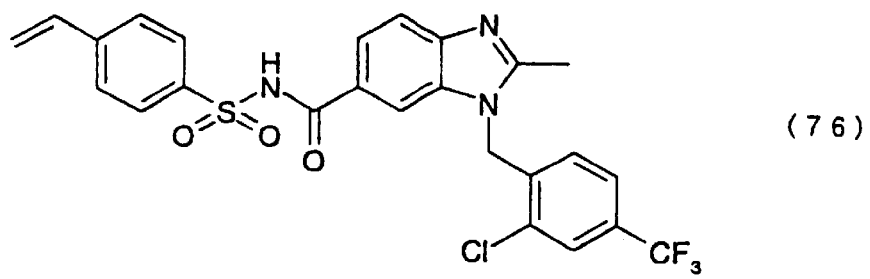
Figure 17:
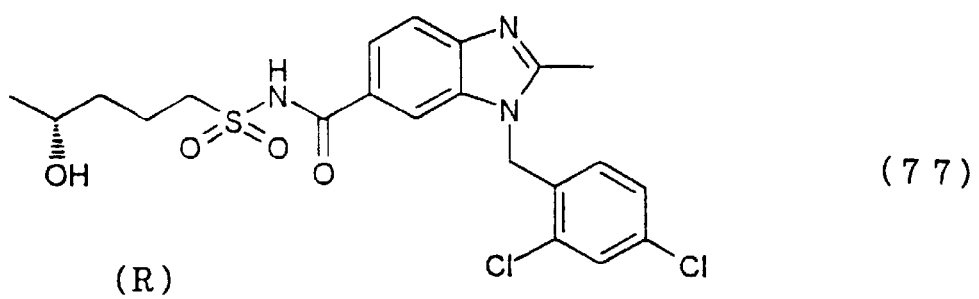
FIG. 17 shows chemical formulae of compound (77) to compound (80).
Figure 17:
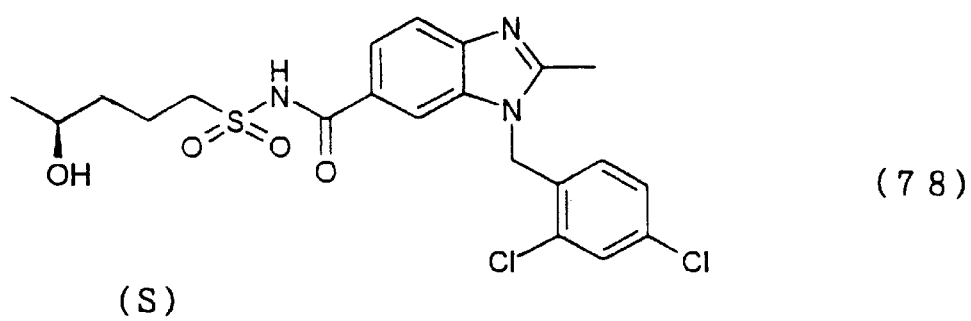
Figure 17:
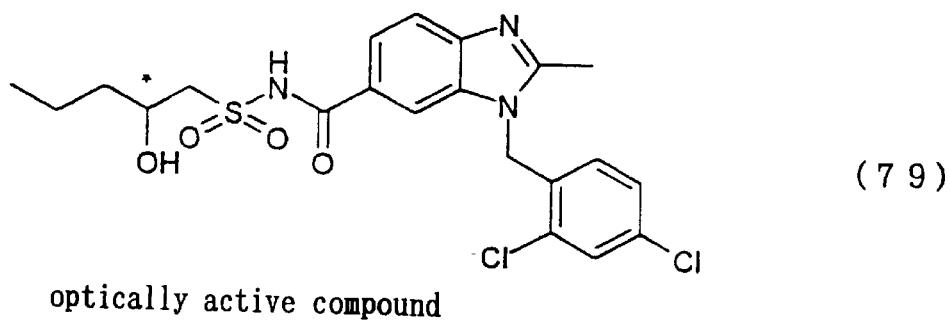
Figure 17:
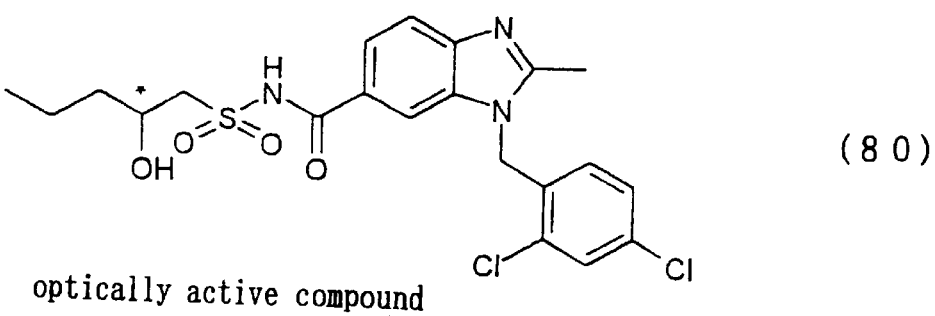
Figure 18:
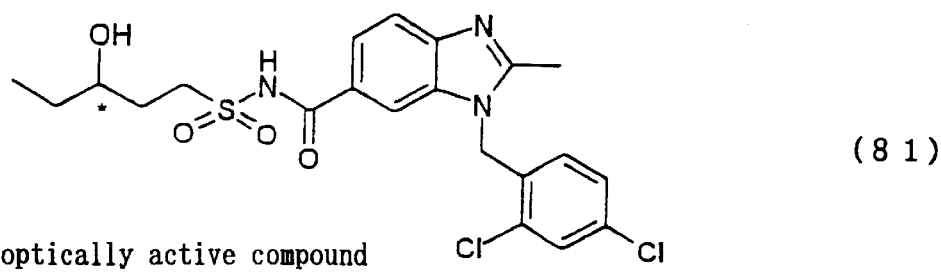
FIG. 18 shows chemical formulae of compound (81) to compound (84).
Figure 18:
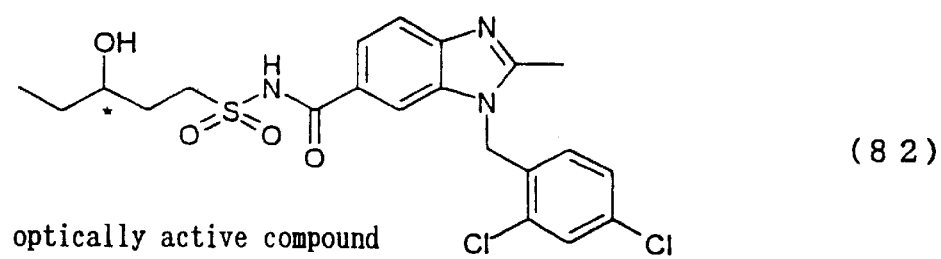
Figure 18:
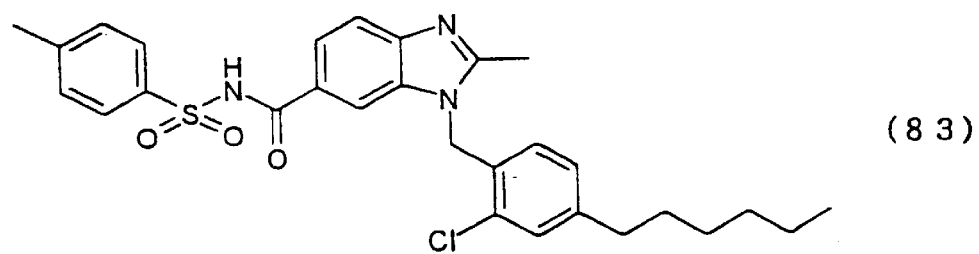
Figure 18:
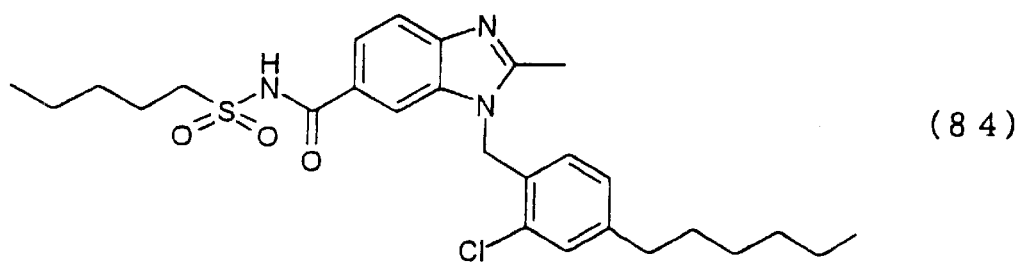
Figure 19:
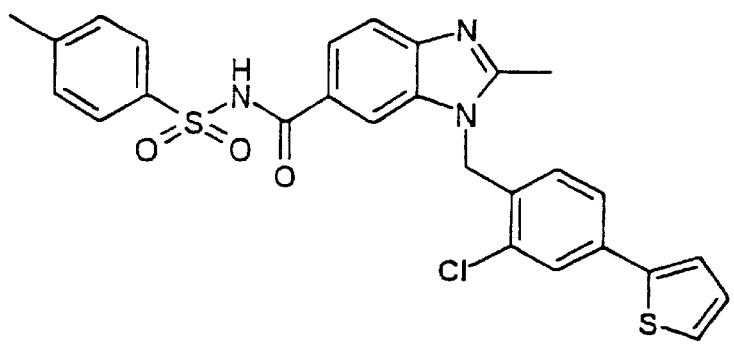
FIG. 19 shows chemical formulae of compound (85) to compound (88).
Figure 19:
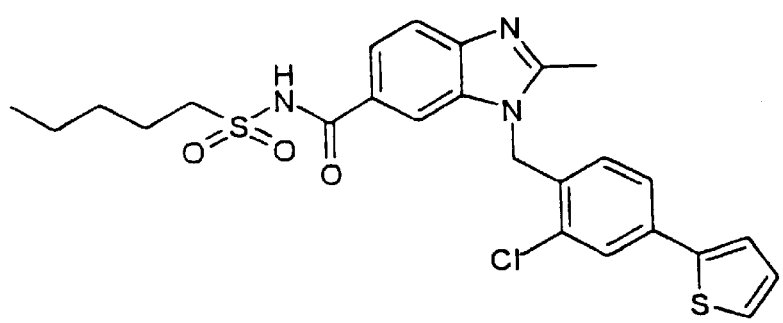
Figure 19:
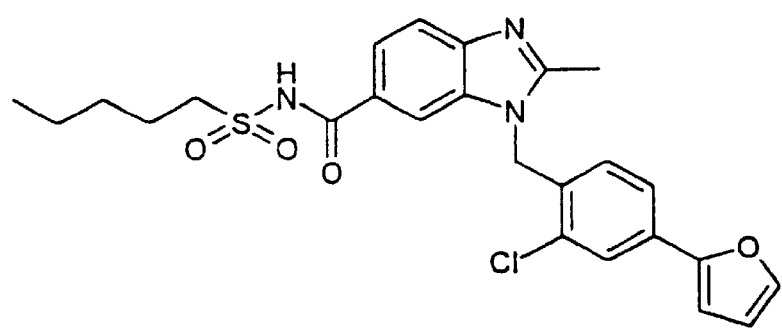
Figure 19:
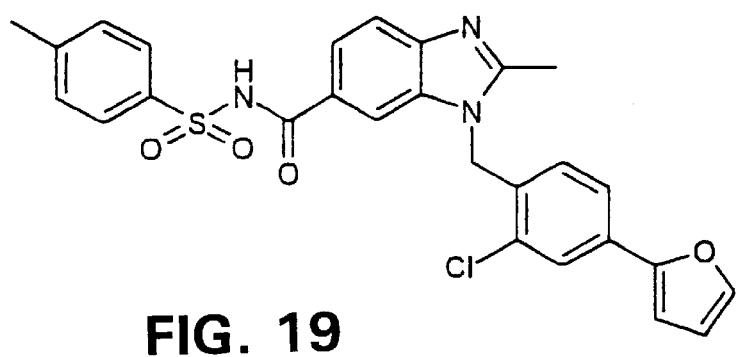
Figure 20:
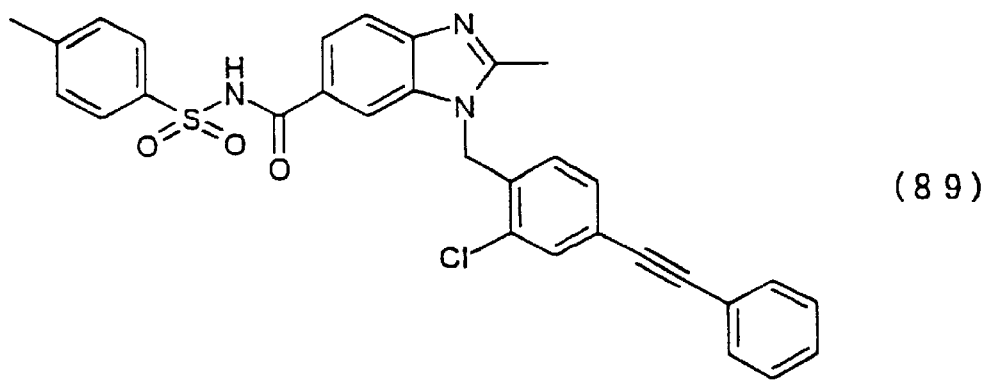
FIG. 20 shows chemical formulae of compound (89) to compound (92).
Figure 20:
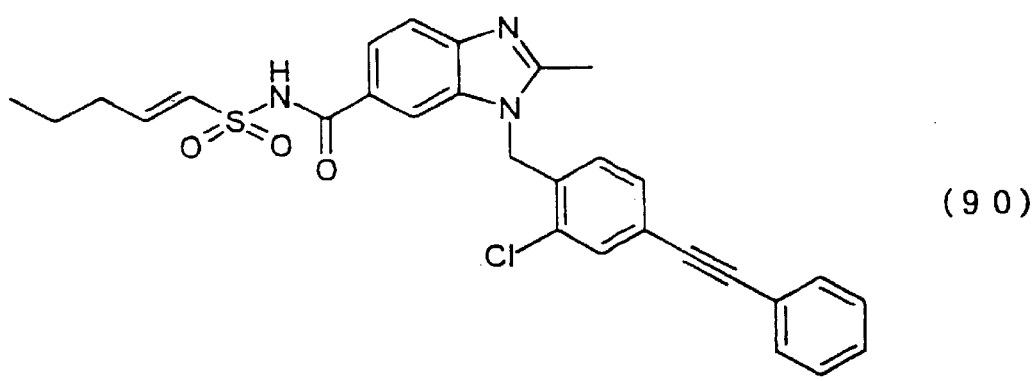
Figure 20:
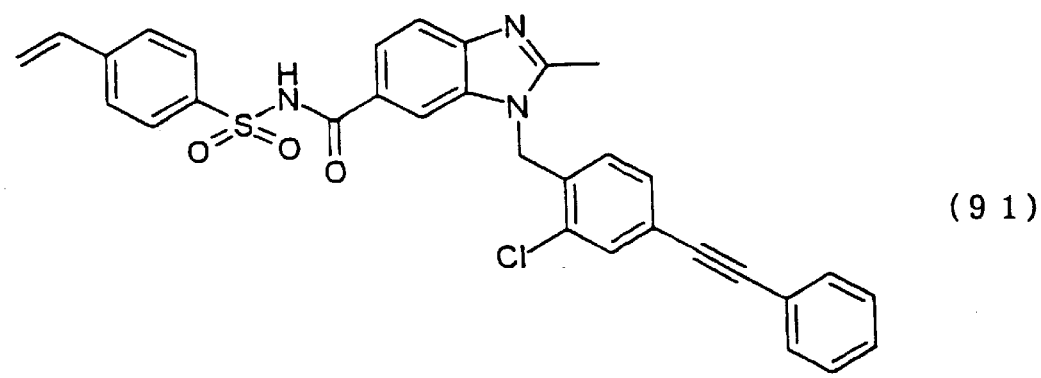
Figure 20:
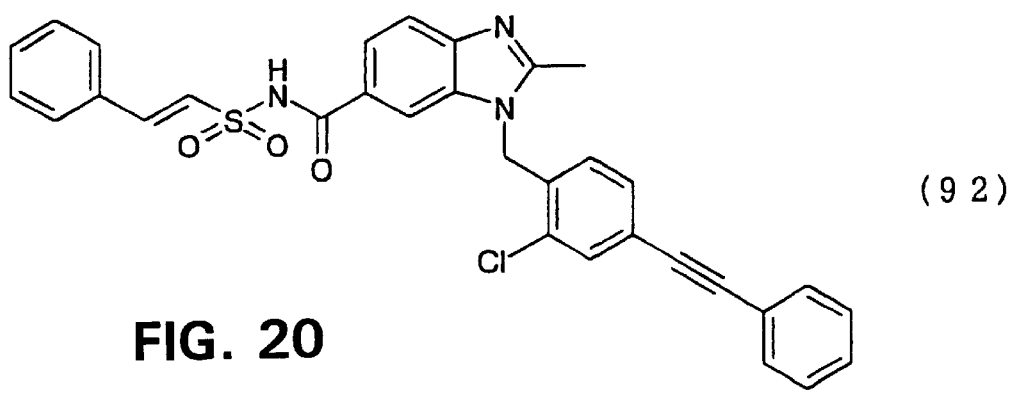
Figure 21:
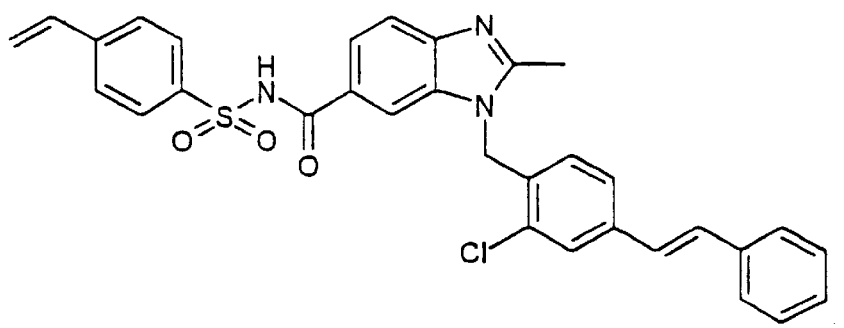
FIG. 21 shows chemical formulae of compound (93) to compound (96).
Figure 21:
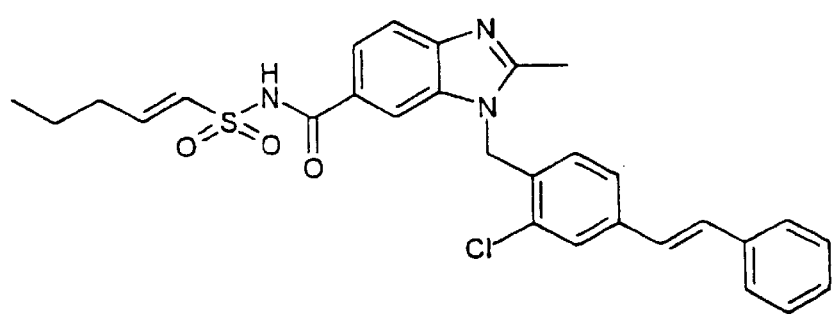
Figure 21:
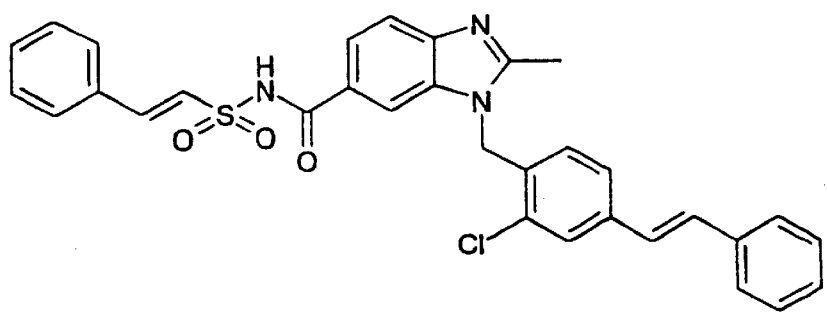
Figure 21:
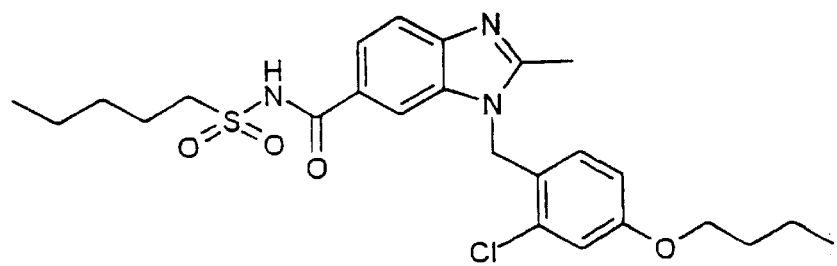
Figure 22:
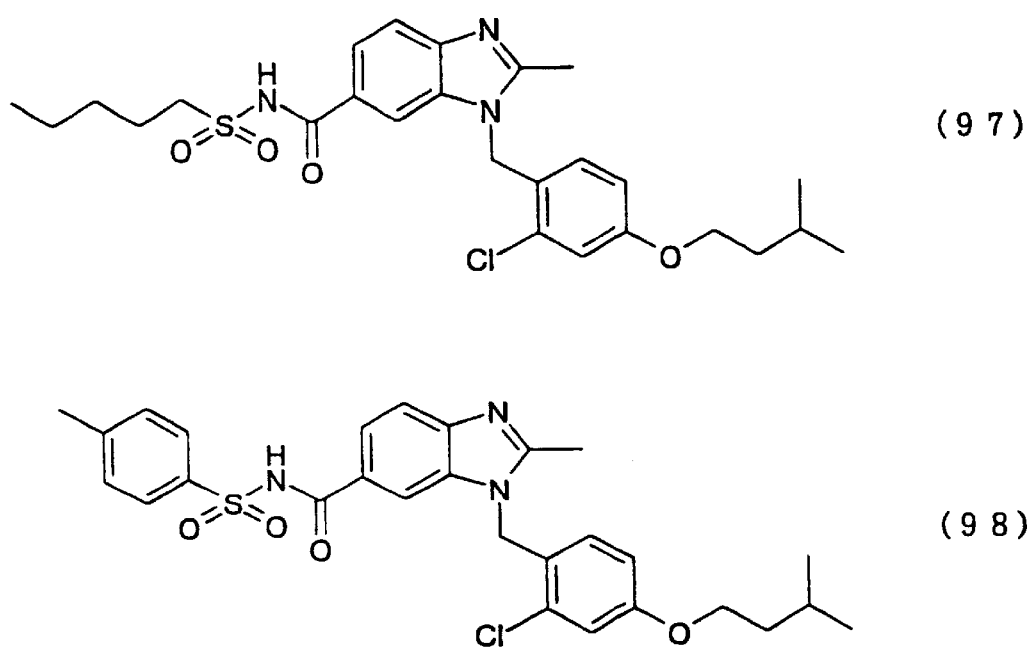
FIG. 22 shows chemical formulae of compound (97) and compound (98).

The present invention is illustrated more specifically by referring to the following Examples. However, the present invention is not limited thereto.

PRODUCTION EXAMPLE 1

Production of ethyl 4(acetylamino)-3-((isoquinolin-3-ylmethyl)-amino)benzoate

A mixture of ethyl 4acetylamino)-3-aminobenzoate (1.11 g), 3-(bromomethyl)isoqinoline (1.37 g), sodium carbonate (0.74 g), sodium iodide (0.15 g), ethyl acetate (10 ml), and water (2.5 ml) was stirred at 70° C. for 20 hours. Water was added to the reaction mixture, which was extracted with ethyl acetate. After the organic layer was dried and concentrated, the residue was purified by silica gel column chromatography (eluate: methanol/ethyl acetate=1/9) to obtain the desired compound, ethyl 4-(acetylamino)-3-((isoquinolin-3-ylmethyl)amino)benzoate (0.91 g).
[Physicochemical Property of the Compound]
$^1$H-NMR (CDCl$_3$, δ ppm): 1.37(3H, t, J=7.1 Hz), 2.69 (3H, s), 4.36(2H, q, J=7.1 Hz), 5.65(2H, s), 7.04(1H, s), 7.60–7.66(3H, m), 7.76(1H, d, J=8.5 Hz), 7.99(2H, m), 8.06(1H, d, J=1.1 Hz), 9.25(1H, s).

PRODUCTION EXAMPLE 2

Production of Ethyl 4-(acetylamino)-3-(((4-chloroisoquinolin-3-yl)methyl)amino)benzoate According to the method of Production Example 1, the desired compound, ethyl 4-(acetylamino)-3-(((4-chloroisoquinolin-3-yl)methyl)amino)benzoate (0.536 g) was obtained using ethyl 4-(acetylamino)-3-aminobenzoate (0.524 g), 4-chloro-3-(chloromethyl)isoquinoline (0.50 g), sodium carbonate (0.300 g), and sodium iodide (0.071 g).
[Physicochemical Property of the Compound]
$^1$H-NMR (CDCl$_3$, δ ppm): 1.38(3H, t, J=7.0 Hz), 2.30 (3H, s), 4.35(2H, q, J=7.1 Hz), 4.72(2H, s), 4.91(1H, brs), 7.58(1H, d, J=7.8 Hz), 7.68(2H, m), 7.85(2H, m), 8.01(2H, m), 8.26(1H, d, J=6.4 Hz), 9.16(1H, s).

PRODUCTION EXAMPLE 3

Production of 6-(Ethoxycarbonyl)-1-(isoquinolin-3-ylmethyl)-2-methylbenzimidazole A mixture of ethyl 4-(acetylamino)-3-((isoquinolin-3-ylmethyl)amino)benzoate (0.90 g) as obtained in Production Example 1, conc. HCl (1 ml), and ethanol (10 ml) was refluxed under heating for 2 hours. The reaction mixture was neutralized with a saturated sodium hydrogencarbonate solution and extracted with ethyl acetate. The resulting extract was concentrated to give the desired compound, 6-(ethoxycarbonyl)-1-(isoquinolin-3-ylmethyl)-2-methyl-benzimidazole (0.92 g).
[Physicochemical Property of the Compound]
$^1$H-NMR (CDCl$_3$, δ ppm): 1.41(3H, t, J=7.1 Hz), 2.70 (3H, s), 4.36(2H, q, J=7.1 Hz), 5.65(2H, s), 7.04(1H, s), 7.60–7.66(3H, m), 7.77(1H, d, J=8.5 Hz), 7.99(2H, m), 8.07(1H, d, J=1.3 Hz), 9.25(1H, s).

PRODUCTION EXAMPLE 4

Production of 1-((4-Chloroisoquinolin-3-yl)methyl)-6-(ethoxy carbonyl)-2-methylbenzimidazole According to the method described in Production Example 3, this compound was synthesized from ethyl 4-(acetylamino)-3-(((4-chloroisoquinolin-3-yl)methyl) amino)benzoate.
[Physicochemical Property of the Compound]
$^1$H-NMR (CDCl$_3$, δ ppm): 1.38(3H, t, J=7.1 Hz), 2.76 (3H, s), 4.34(2H, q, J=7.1 Hz), 5.77(2H, s), 7.69(2H, m), 7.86(2H, m), 7.94(2H, m), 8.13(1H, d, J=1.3 Hz), 8.28(1H, d, J=8.4 Hz), 8.98(1H, s).

PRODUCTION EXAMPLE 5

Preparation of 6-Carboxy-1-(isoquinolin-3-ylmethyl)-2-methyl-benzimidazole

A mixture of 6-(ethoxycarbonyl)-1-(isoquinolin-3-ylmethyl)-2-methylbenzimidazole (0.91 g) as obtained in Production Example 3, aqueous 10% sodium hydroxide (10 ml), and ethanol (10 ml) was refluxed under heating for 1 hour. The reaction mixture was once acidified by adding conc. HCl (2 ml), and then neutralized with aqueous saturated sodium hydrogencarbonate. Precipitated crystals were collected and dried to obtain the desired compound, 6-carboxy-1-(isoquinolin-3-ylmethyl)-2-methyl-benzimidazole (0.79 g).

[Physicochemical Property of the Compound]
¹H-NMR (DMSO-d6, δ ppm): 2.66(3H, s), 5.75(2H, s), 7.58(1H, d, J=8.4 Hz), 7.65(1H, t, J=7.1 Hz), 7.72(1H, s), 7.76(2H, m), 7.93(1H, d, J=8.3 Hz), 8.09(2H, m), 9.28(1H, s).

PRODUCTION EXAMPLE 6

Production of 6-Carboxy-1-((4-chloroisoquinolin-3-yl)methyl)-2-methylbenzimidazole According to the method described in Production Example 5, this compound was synthesized from 1-((4-chloroisoquinolin-3-yl)methyl)-6-(ethoxycarbonyl)-2-methylbenzimidazole.
[Physicochemical Property of the Compound]
¹H-NMR (DMSO-d6, δ ppm): 2.59(3H, s), 5.90(2H, s), 7.50(1H, d, J=8.4 Hz), 7.44(1H, dd, J=8.4 and 1.3 Hz), 7.79(1H, t, J=7.5 Hz), 7.99(2H, m), 8.15(1H, d, J=8.1 Hz), 8.26(1H, d, J=8.5 Hz), 9.13(1H, s)

PRODUCTION EXAMPLE 7

Production of 1-((1-Bromonaphthalen-2-yl)methyl)-6-carboxy-2-methylbenzimidazole According to the method of Production Example 1, the crude product of the desired compound, ethyl 4-(acetylamino)-3-(((1-bromonaphthalen-2-yl)methyl) amino)benzoate, was obtained using ethyl 4-(acetylamino)-3-aminobenzoate (0.50 g), 1-bromo-2-(bromomethyl) naphthalene (0.81 g), sodium carbonate (0.38 g), and sodium iodide (0.10 g).

This product was immediately converted to 1-((1-bromonaphthalen-2-yl)methyl)-6-carboxy-2-methylbenzimidazole (0.514 g) according to the method of Production Example 3, followed by the method of Production Example 5.
[Physicochemical Property of the Compound]
¹H-NMR (DMSO-d6, δ ppm): 2.56(3H, s), 5.84(2H, s), 6.61(1H, d, J=8.6 Hz), 7.63(1H, t, J=7.8 Hz), 7.66(1H, d, J=8.5 Hz), 7.75(1H, t, J=7.8 Hz), 7.81(1H, d, J=8.6 Hz), 7.86(1H, d, J=8.6 Hz), 7.95(1H, d, J=8.2 Hz), 7.99(1H, s), 8.30(1H, d, J=8.6 Hz), 12.69(1H, s).

PRODUCTION EXAMPLE 8

Production of 1-(2,4-Dichlorobenzyl)-6-(hydrazinocarbonyl)-2-methylbenzimidazole A mixture of 6-carboxy-1-(2,4-dichlorobenzyl)-2-methylbenzimidazole (597 mg) as obtained in Production Example 14, 1, 1'-carbonyldiimidazole (433 mg), and dehydrated N,N-dimethyl-formamide (6.0 ml) was stirred at room temperature for 1 hour. To the reaction solution were added diazabicycloundecene (0.40 ml) and tert-butoxycarbonylhydrazine (353 mg). The mixture was stirred at 100° C. for 4 hours. After cooling, water (30 ml) was added to the mixture, which was adjusted to pH 4 with HCl and extracted with a mixed solvent of chloroform/methanol (4/1). The organic layer was dried over magnesium sulfate and evaporated to dryness under reduced pressure. The resulting residue was washed with ether to obtain 1-(2,4-dichlorobenzyl)-6-(hydrazinocarbonyl)-2-methyl-benzimidazole as light-yellow powder (250 mg).
[Physicochemical Property of the Compound]
¹H-NMR (DMSO-d6): 2.52(3H, s), 5.64(2H, s), 6.51(1H, d, J=8 Hz), 7.34(1H, d, J=8 Hz), 7.65(1H, d, J=8 Hz), 7.72(1H, d, J=8 Hz), 7.90(1H, s).

PRODUCTION EXAMPLE 9

Production of 6-(tert-Butoxycarbonylamino)-1-(2,4-dichloro-benzyl)-2-methylbenzimidazole A mixture of 6-carboxy-1-(2,4-dichlorobenzyl)-2-methylbenzimidazole (200 mg) as obtained in Production Example 14, tert-butyl alcohol (5.7 ml), diphenylphosphoryl azide (1.54 ml), triethylamine (1.0 ml), and 1,4dioxane (20 ml) was refluxed under heating for 12 hours. The reaction solution was allowed to cool, diluted with ethyl acetate, and washed successively with saturated aqueous sodium hydrogencarbonate three times and with water once. The organic layer was evaporated to dryness under reduced pressure, and the residue was purified by silica gel column chromatography (chloroform/methanol=200/1 as eluate) to obtain 6-(tert-butoxycarbonylamino)-1-(2,4-dichlorobenzyl)-2-methyl-benzimidazole as white powder (2.15 g).
[Physicochemical Property of the Compound]
¹H-NMR (DMSO-d6): 1.42(9H, s), 2.42(3H, s), 5.40(2H, s), 6.44(1H, d, J=8 Hz), 7.12(1H, d, j=8 Hz), 7.32(1H, d, J=8 Hz), 7.42(1H, d, J=8 Hz), 7.49(1H, brs), 7.72(1H, s), 9.27 (1H, brs).

PRODUCTION EXAMPLE 10

Production of 6-Amino-1-(2,4-dichlorobenzyl)-2-methyl-benzimidazole 6-(tert-Butoxycarbonylamino)-1-(2,4-dichlorobenzyl)-2-methylbenzimidazole (2.05 g) as obtained in Production Example 9 was dissolved in 4 N HCl/ethyl acetate (20 ml) and stirred at room temperature for 1 hour. The reaction mixture was evaporated to dryness under reduced pressure, and the residue was extracted using chloroform and saturated aqueous sodium hydrogencarbonate. The organic layer was dried over magnesium sulfate, and evaporated to dryness under reduced pressure to obtain 6-amino-1-(2,4-dichlorobenzyl)-2-methylbenzimidazole as white powder (1.52 g).
[Physicochemical Property of the Compound]
¹H-NMR (DMSO-d6): 2.38(3H, s), 5.32(2H, s), 6.32(1H, s), 6.43(1H, d, J=8 Hz), 6.48(1H, d, J=8 Hz), 7.22(1H, d, J=8 Hz), 7.33(1H, dd, J=8, 2 Hz), 7.72(1H, d, J=8 Hz).

PRODUCTION EXAMPLE 11

Production of 2-Chloro-1-((methanesulfonyloxy) methyl)-4-(trifluoromethyl)benzene Methanesulfonyl chloride (1.1 ml) was added dropwise to a solution of 2-chloro-4-(trifluoromethyl)benzyl alcohol (2.64 g) and anhydrous triethylamine (2.3 ml) in anhydrous dichloromethane (30 ml) in a nitrogen stream under ice-cooling and the mixture was stirred for 30 minutes under the same conditions. The reaction mixture was successively washed with water, aqueous sodium hydrogencarbonate, and saturated aqueous sodium chloride, dried over anhydrous magnesium sulfate. The filtrate was concentrated to give 2-chloro-1-((methanesulfonyloxy)methyl)-4-(trifluoromethyl)benzene as white crystals (3.62 g).
[Physicochemical Property of the Compound]
¹H-NMR (CDCl₃): 3.08(3H, s), 5.37(2H, s), 7.58(1H, d, J=8 Hz), 7.65(1H, d, J=8 Hz), 7.70(1H, s).

PRODUCTION EXAMPLE 12

Production of Ethyl 4-(acetylamino)-3-((2-chloro-4-(trifluoro-methyl)benzyl)amino)benzoate Ethyl 4-(acetylamino)-3-((2-chloro-4-(trifluoromethyl)-benzyl)amino)benzoate was obtained as white crystals (915 mg) from ethyl 4-(acetylamino)-3-aminobenzoate (700 mg) and 2-chloro-1-((methanesulfonyloxy)methyl)-4-(trifluoromethyl)benzene (909 mg) in the same manner as in Production Example 1 except for using N,N-dimethyl formamide as the solvent and potassium carbonate as the base.
[Physicochemical Property of the Compound]
$^1$H-NMR(CDCl$_3$): 1.33(3H, t, J=7 Hz), 2.25(2H, s), 4.31 (2H, q, J=8 Hz), 4.53(3H, s), 7.33(1H, s), 7.40(1H, d, J=8 Hz), 7.46–7.55(3H, m), 7.68(1H, s).

PRODUCTION EXAMPLE 13

Production of 6-Carboxy-1-(2-chloro-4-(trifluoromethyl)benzyl)-2-methylbenzimidazole By performing successively the methods of Production Examples 3 and 5, 6-carboxy-1-(2-chloro-4-(trifluoromethyl)benzyl)-2-methylbenzimidazole (777 mg) was obtained as white crystals from 4-(acetylamino)-3-((2-trifluoromethyl)benzyl)amino))benzoate (910 mg) as obtained in Production Example 12.
[Physicochemical Property of the Compound]
$^1$H-NMR(DMSO-d6): 2.51(3H, s), 5.71(2H, s), 6.63(1 H, d, J=8 Hz), 7.63(2H, t, J=8 Hz), 7.82(1H, d, J=8 Hz), 8.01(2H, s).

PRODUCTION EXAMPLE 14

<First Step>

Production of Ethyl 4-(acetylamino)-3-nitrobenzoate

Acetyl chloride (62 ml) was added dropwise to a mixture of ethyl 4-amino-3-nitrobenzoate (142 g), N,N-dimethylaniline (110 ml), and toluene (940 ml) in an ice bath. After stirring the mixture at 50° C. for 3 hours, it was cooled. Water (142 ml) was added thereto to stop the reaction. The toluene layer was separated and the organic layer was washed with dilute hydrochloric acid and successively with water. After the organic layer was concentrated to about 1/3 volume, hexane (284 ml) was added thereto for crystallization. Crystals were collected by filtration and washed with hexane to obtain the desired compound, ethyl 4-(acetylamino)-3-nitrobenzoate (157.7 g).
[Physicochemical Property of the Compound]
$^1$H-NMR (CDCl$_3$, δ ppm): 1.42(3H, t, J=7.1 Hz), 2.33 (3H, s), 4.42(2H, q, J=7.1 Hz), 8.28(1H, dd, J=2.1 and 8.9 Hz), 8.89(1H, d, J=2.1 Hz), 8.91(1H, d, J=8.9 Hz), 10.55 (1H, brs).

<Second Step>

Production of Ethyl 4-(acetylamino)-3-aminobenzoate

A mixture of wet crystals of 4-(acetylamino)-3-nitrobenzoate (45.3 g, purity: 66.2%), ethanol (191.6 g), water (31.9 g), and palladium-on-carbon (palladium content: 5%, water content: 50%, 3.0 g) was stirred at 40° C. for 19 hours at a hydrogen atmosphere. The catalyst was collected by filtration and washed with a mixed solvent of water and ethanol (1/9, 30.0 g). The filtrate was concentrated, and t-butyl methyl ether (33.0 g) was added dropwise thereto at 50° C., and the mixture was cooled to 10° C. to effect crystallization. Crystals were collected and washed with t-butyl methyl ether (30.0 g), and dried at 60° C. under reduced pressure. Thus, ethyl 4-(acetylamino)-3-aminobenzoate (18.2 g) was obtained.
[Physicochemical Property of the Compound]
$^1$H-NMR(DMSO-d6, δ ppm): 1.27(3H, t), 2.05(3H, s), 4.23(2H, q), 5.19(2H, s), 7.13(1H, d, J=8.2 Hz), 7.35(1H, s), 7.47(1H, d, J=8.2 Hz), 9.19(1H, s).

<Third Step>

Production of Ethyl 4-(acetylamino)-3-((2,4-dichlorobenzyl)-amino)benzoate

In the same manner as in Production Example 1, the desired compound (46.8 g) was obtained from ethyl 4-(acetylamino)-3-aminobenzoate (40 g), 2,4-dichlorobenzyl chloride (42.2 g), potassium carbonate (30 g), and sodium iodide (8.1 g).
[Physicochemical property of the compound]
$^1$H-NMR (CDCl$_3$ δ ppm): 1.37(3H, t, J=7.1 Hz), 2.23(3H, s), 4.30(2H, q, J=7.1 Hz), 4.38(1H, d, J=5.3 Hz), 4.41(2H, d, J=5.7 Hz), 7.18(1H, d, J=8.3 Hz), 7.31(1H, d, J=8.3 Hz), 7.39(1H, d, J=7.3 Hz), 7.42(1H, d, J=2.0 Hz), 7.46(1H, d, J=8.2 Hz), 7.51(1H, d, J=8.2 Hz).

<Fourth and Fifth Steps>

Production of 6-Carboxy-1-(2,4-dichlorobenzyl)-2-methyl-benzimidazole

In the same manner as in Production Example 3 and successively in Production Example 5, the desired compound (34.7 g) was obtained from ethyl 4-(acetylamino)-3-((2,4dichlorobenzyl)amino)benzoate (40 g) via 1-(2,4-dichlorobenzyl)-46(ethoxycarbonyl)-2-methyl-benzimidazole.
[Physicochemical Property of the Compound]
$^1$H-NMR (DMSO-d6, δ ppm): 2.52(3H, s), 5.62(2H, s), 6.53(1H, d, J=8.5 Hz), 7.33(1H, dd, J=8.5 and 2.1 Hz), 7.64(1H, d, J=8.4 Hz), 7.74(1H, d, J=2.2 Hz), 7.81(1H, dd, J=8.4 and 1.4 Hz), 7.98(1H, s), 12.74(1H, brs).

PRODUCTION EXAMPLE 15

<First Step>

Production of N-t-butylmethanesulfonamide

Methanesulfonyl chloride (229 g) was added dropwise to a solution (800 ml) of t-butylamine (420 g) in chloroform under cooling in an ice bath for 90 minutes. After stirring for 3 hours at room temperature, the solution was refluxed under heating for 1 hour. The resulting reaction mixture was cooled with ice, made acidic by adding dilute hydrochloric acid, and extracted with chloroform. The organic layer was washed with water and dried over sodium sulfate. The resulting solution was distilled under reduced pressure to obtain N-t-butylmethanesulfonamide (244 g) as white solid. This product was immediately subjected to the next step.

<Second Step>

Production of N-t-butyl-2-hydroxy-1-pentanesulfonamide

A 2.0 M solution of lithium diisopropylamide in heptane/tetrahydrofuran/ethylbenzene (400 ml) was cooled to −45 to −50° C. under nitrogen atmosphere. A solution (100 ml) of N-t-butylmethanesulfonamide (55.0 g) in tetrahydrofuran was added dropwise thereto for 20 minutes. After raising the temperature to 5° C. taking 1 hour, the solution was cooled again to −65° C. To the resulting solution was added dropwise a solution of n-butyl aldehyde (28.8 g) in tetrahydrofuran (100 ml) for 30 minutes. The solution was stirred for 18 hours while raising the temperature gradually to room temperature. The resulting reaction solution was poured into an excess amount of dilute hydrochloric acid under cooling with ice to make it acidic and extracted with ethyl acetate. The organic layer was washed with water, dried over sodium sulfate, and concentrated under reduced pressure to obtain a solid crude product. Hexane (300 ml) was added thereto with stirring. Crystals thus obtained were collected by filtration, washed with hexane, and dried under reduced pressure to obtain N-t-butyl-2-hydroxy-1-pentanesulfonamide (46.2 g) as white crystals.

[Physicochemical Property of the Compound]

$^1$H-NMR (CDCl$_3$, δ ppm): 0.95(3H, t, J=7.0 Hz), 1.39 (9H, s), 1.41–1.49(3H, m), 1.60(1H, m), 3.15(2H, m),3.28 (1H, d, J=2.1 Hz), 4.20(1H, m), 4.48(1H, s).

<Third Step>

Production of N-t-butyl-2-benzoyloxy-1-pentanesulfonamide

Under nitrogen atmosphere, benzoic acid (92.8 g) was added gradually to a mixture of N,N'-carbonyldiimidazole (123.3 g) and tetrahydrofuran (500 ml) taking 10 minutes at room temperature. After stirring for 1 hour at room temperature, a solution of N-t-butyl-2-hydroxy-1-pentanesulfonamide (84.9 g) in tetrahydrofuran (300 ml) was added dropwise thereto taking 15 minutes. Then, a solution of diazabicycloundecene (57.9 g) in tetrahydrofuran (200 ml) was added dropwise thereto taking 35 minutes and the resulting solution was stirred for 17 hours at room temperature. The reaction mixture was decanted to ice-water, made acidic by adding dilute hydrochloric acid, and extracted with chloroform. The organic layer was washed with a saturated aqueous solution of sodium hydrogencarbonate and water, dried over sodium sulfate, and concentrated under reduced pressure to obtain N-t-butyl-2-benzoyloxy-1-pentanesulfonamide (132.8 g) as yellowish brown oil.

[Physicochemical property of the compound]

$^1$H-NMR (CDCl$_3$, δ ppm): 0.96(3H, t, J=7.4 Hz), 1.32 (9H, s), 1.41–1.49(2H, m), 1.75–1.87(2H, m), 3.30(1H, dd, J=14.7 and 3.8 Hz), 3.49(1H, dd, J=14.7 and 7.5 Hz), 4.41(1H, s), 5.63(1H, m), 7.45(2H, t, J=7.7 Hz), 7.57(1H, m),8.05(2H, d, J=8.2 Hz).

<Fourth Step>

Production of 2-Benzoyloxy-1-pentanesulfonamide

Trifluoroacetic acid (200 ml) was added to N-t-butyl-2-benzoyloxy-1-pentanesulfonamide (132.8 g). After stirring for 32 hours at room temperature, the solution was concentrated under reduced pressure. After further adding trifluoroacetic acid (100 ml) and stirring for 16 hours at room temperature, the solution was concentrated under reduced pressure to obtain an oily substance (165 g). This substance was dissolved in ethyl acetate and, after adding a saturated aqueous solution of sodium hydrogencarbonate, the solution was stirred for 15 minutes at room temperature. The organic layer was washed with 5% brine, dried over sodium sulfate, and concentrated under reduced pressure to obtain 2-benzoyloxy-1-pentanesulfonamide (92.8 g).

[Physicochemical Property of the Compound]

$^1$H-NMR (CDCl$_3$, δ ppm): 0.97(3H, t, J=6.9 Hz), 1.39–1.55(2H, m), 1.73–1.81(1H, m), 1.82–1.91(1H, m), 3.39(1H, dd, J=14.8 and 3.5 Hz), 3.52(1H, dd, J=14.8 and 8.2 Hz), 5.00(2H, s), 5.67(1 H, m), 7.46(2H, t, J=7.8 Hz), 7.59(1H, t, J=7.4 Hz), 8.05(2H, dd, J=8.5 and 1.2 Hz).

<Fifth Step>

Production of 6-((2-Benzoyloxy-1-pentane)sulfonylcarbamoyl)-1-(2,4-dichlorobenzyl)-2-methylbenzimidazole 6-Carboxy-1-(2,4-dichlorobenzyl)-2-methylbenzimidazole (50.3 g) as obtained in Production Example 14 and N,N'-carbonyldiimidazole (48.7 g) were added to N,N-dimethylformamide (400 ml) and stirred for 30 minutes at 40° C. and, then, for 30 minutes at room temperature. 2-Benzoyloxy-1-pentanesulfonamide (81.4 g) and diazabicycloundecene (45.7 g) were added dropwise thereto and the solution was stirred for 22 hours at room temperature. The reaction solution was cooled with ice, made acidic by adding hydrochloric acid, and extracted with chloroform. The organic layer was washed with water, dried over sodium sulfate, and concentrated under reduced pressure. To the thus-obtained oily substance (156 g) were added acetonitrile (100 ml) and isopropyl ether (500 ml). The resulting mixture was heated to 60° C. and allowed to be cooled to room temperature. Deposited crystals were collected by filtration, washed with a mixed solution of acetonitrile (50 ml) and isopropyl ether (200 ml), and dried under reduced pressure to obtain 6-((2-benzoyloxy-1-pentane) sulfonylcarbamoyl)-1-(2,4-dichloro-benzyl)-2-methylbenzimidazole (52.2 g).

[Physicochemical Property of the Compound]

$^1$H-NMR (DMSO-d6, δ ppm): 0.85(3H, t, J=7.3 Hz), 1.31(2H, m), 1.74(2H, q, J=6.4 Hz), 2.47(3H, s), 3.93(1H, d, J=15.0 Hz), 4.11(1H, dd, J=15.1 and 8.6 Hz), 5.41–5.58(3H, m), 6.36(1H, d, J=8.4 Hz), 7.24(2H, t, J=7.7 Hz), 7.30(1H, d, J=8.4 Hz), 7.45(1H, t, J=7.4 Hz), 7.59(1H, d, J=8.5 Hz), 7.74(4H, m), 7.97(1H, s), 12.01(1H, brs).

PRODUCTION EXAMPLE 16

<First Step>

Production of Sodium 4-pentene-1-sulfonate

5-Bromo-1-pentene (199.74 g), sodium sulfite (202.67 g), and water (650 ml) were mixed at room temperature. Under reflux, the solution was stirred for 19 hours. After cooling to room temperature, t-butyl methyl ether was added thereto. The aqueous layer separated was concentrated and dehydrated azeotropically with toluene. Thus, sodium 4-pentene-1-sulfonate (1) containing inorganic substances (387.51 g) was obtained as white solid.

[Physicochemical Property of the Compound]

$^1$H-NMR (DMSO-d6, δ ppm: 1.60–1.67(2H, m), 2.05(2H, q, J=7.2 Hz), 2.38–2.42(2H, m), 4.92–5.00(2H, m), 5.72–5.81(1H, m).

<Second Step>

Production of 4-Pentene-1-sulfonyl Chloride

Phosphorus oxychloride (570.02 g) was added to sodium 4-pentene-1-sulfonate (199.18 g) at room temperature. After reflux for 3 hours, the solution was cooled in an ice bath. The reaction solution was added gradually to a large amount of ice water. After extraction with diethyl ether, the organic layer was washed with brine, dried with magnesium sulfate, and concentrated under reduced pressure to obtain 4-pentene-1-sulfonyl chloride (106.31 g) as dark brown oil.

[Physicochemical Property of the Compound]

$^1$H-NMR (CDCl$_3$, δ ppm: 2.13–2.19(2H, m), 2.28(2H, q, J=6.9 Hz), 3.65–3.68(2H, m), 5.10–5.14(2H, m), 5.72–5.81 (1H, m).

<Third Step>

Production of N-t-butyl-4-pentene-1-sulfonamide

A solution (30 ml) of 4-pentene-1-sulfonyl chloride (190.85 g) in chloroform was added dropwise to a solution (300 ml) of t-butylamine (289.70 g) in chloroform in an ice bath taking 1 hour and 20 minutes. After reflux for 3 hours, the solution was cooled, made acidic by adding dilute hydrochloric acid, and extracted with chloroform. The organic layer was concentrated under reduced pressure to give the residue (261.9 g), which was purified by silica gel column chromatography (eluate: ethyl acetate/hexane=1/1). Thus, N-t-butyl-4-pentene-1-sulfonamide (194.73 g) was obtained as orange oil.
[Physicochemical Property of the Compound]
$^1$H-NMR (CDCl$_3$, δ ppm): 1.37(9H, s), 1.89–1.96(2H, m), 2.19(2H, q, J=7.0 Hz), 3.01–3.05(2H, m), 4.11(1H, s), 5.03–5.09(2H, m), 5.72–5.81(1H, m).
<Fourth Step>

Production of N-t-butyl-(3-(2-oxylanyl)-1-propane) sulfonamide m-Chloroperbenzoic acid (214.82 g) was added to a solution (600 ml) of N-t-butyl-4-pentane-1-sulfonamide (1 94.73 g) in methylene chloride in an ice bath taking 2 hours. After stirring for 5 hours in an ice bath, the solution was stirred overnight at room temperature. m-Chloroperbenzoic acid (55.47 g) was added and the solution was stirred overnight. The reaction mixture was filtered under reduced pressure and a 5 % aqueous solution of sodium hydrogensulfite and saturated brine were added to the resulting filtrate. The solution thus obtained was extracted with methylene chloride. The organic layer was washed with an aqueous solution of sodium hydrogencarbonate, dried over magnesium sulfate, and concentrated under reduced pressure to obtain t-butyl-(3-(2-oxylanyl)-1-propane) sulfonamide (166.61 g) as light yellow oil.
[Physicochemical Property of the Compound]
$^1$H-NMR(CDCl$_3$, δ ppm): 1.38(9H, s), 1.50–1.62(1H, m), 1.81–1.91(1H, m), 1.95–2.05(2H, m). 2.49–2.51(1H, m), 2.76–2.80(1H, m), 2.92–2.96(1H, m), 3.03–3.19(2H, m), 4.23(1H, s).
<Fifth Step>

Production of N-t-butyl-4-hydroxy-1-pentanesulfonamide

Under nitrogen atmosphere, a solution (200 ml) of N-t-butyl-(3-(2-oxylanyl)-1-propane)sulfonamide (83.36 g) in tetrahydrofuran was added dropwise to a solution (800 ml) of 1.0 M lithium triethylhydroborate in tetrahydrofuran taking 1 hour and stirred for 1 hour and 30 minutes. The reaction was stopped by adding 5 % hydrochloric acid in an ice bath. Concentrated hydrochloric acid was added thereto to neutralize the reaction solution. The reaction solution was concentrated to about ½ volume and extracted with ethyl acetate. The organic layer was dried over magnesium sulfate and concentrated under reduced pressure. Hexane (400 ml) was added to the resulting residue (92.21 g) and crystallization was initiated by adding seed crystals while stirring. Deposited crystals were separated by filtration, washed with hexane, and dried under reduced pressure to obtain N-t-butyl4-hydroxy-1-pentanesulfonamide (57.07 g) as white solid.
[Physicochemical Property of the Compound]
$^1$H-NMR(CDCl$_3$, δ ppm): 1.22(3H, d, J=6.3 Hz), 1.37 (9H, s), 1.54–1.62(2H, m), 1.66(1H, brs), 1.86–2.00(2H, m), 3.09(2H, t, J=7.8 Hz), 3.81–3.87(1H, m), 4.19(1H, brs).
<Sixth Step>

Production of N-t-butyl-benzoyloxy-1-pentanesulfonamide

Under nitrogen atmosphere, N,N'-carbonyldiimidazole (152.07 g) was added to tetrahydrofuran solution (600 ml) of benzoic acid (114.46 g) in an ice bath and stirred for 1 hour. N-t-butyl-4-hydroxy-1-pentanesulfonamide (99.73 g) and diazabicycloundecene (142.78 g) were added thereto and stirred overnight at room temperature. Under reduced pressure, about ½ volume of tetrahydrofuran was removed. The reaction solution was made acidic with dilute hydrochloric acid in an ice bath and extracted with chloroform. After washing with a saturated aqueous solution of sodium hydrogencarbonate, the organic layer was dried over magnesium sulfate and concentrated under reduced pressure. Hexane (500 ml) and t-butylmethylether (25 ml) were added to the resulting residue (148.18 g) and crystallization was initiated by adding seed crystal.

Deposited crystals were separated by filtration, washed (hexane/t-butyl methyl ether=20/1) and dried under reduced pressure. Thus, N-t-butyl-benzoyloxy-1-pentanesulfonamide (137.89 g) was obtained as light yellow solid.
[Physicochemical Property of the Compound]
$^1$H-NMR(CDCl$_3$, δ ppm): 1.33(9H, s), 1.37(3H, d, J=6.3 Hz), 1.76–1.99(4H, m), 3.03–3.13(2H, m), 4.12(1H, s), 5.17–5.23(1H, m), 7.42–7.46(2H, m), 7.54–7.58(1H, m), 8.02–8.04(2H, m).
<Seventh Step>

Production of 4-Benzoyloxy-1-pentanesulfonamide

A mixture of N-t-butyl-4-benzoyloxy-1-pentanesulfonamide (15.0 g) and trifluoroacetic acid (70 ml) was stirred overnight at room temperature. The reaction solution was concentrated under reduced pressure. Water and chloroform were added to the residue. Then, a saturated aqueous solution of sodium hydrogencarbonate was added thereto while stirring to adjust the pH of the aqueous to neutral. The chloroform layer was dried over sodium sulfate and concentrated. The resulting residue was purified by silica gel column chromatography (eluate: ethyl acetate) to obtain 4-benzoyloxy-1-pentanesulfonamide (11.1 g).
[Physicochemical Property of the Compound]
$^1$H-NMR (CDCl$_3$, δ ppm): 1.38(3H, d, J=6.2 Hz), 1.77–2.05(4H, m), 3.17(2H, m), 4.72(2H, brs), 5.21(1H, m), 7.44(2H, t), 7.57(1H, t), 8.03(2H, m).
<Eighth Step>

Production of 6-((4-Benzoyloxy-1-pentane) sulfonylcarbamoyl)-1-(2,4-dichlorobenzyl)-2-methylbenzimidazole N,N'-carbonyldiimidazole (6.60 g) was added to an N,N-dimethylformamide solution (90 ml) of 6-carboxy-1-(2,4-dichlorobenzyl)-2-methylbenzimidazole (10.2 g) as obtained in Production Example 14 and stirred for 1 hour at room temperature. 4-Benzoyloxy-1-pentanesulfonamide (11.1 g) and diazabicycloundecene (6.20 g) was added thereto and the solution was stirred overnight at 80° C. The solvent was removed under reduced pressure. Ethanol (100 ml) and water (50 ml) were added to the residue to make the solution homogeneous and the pH was adjusted to about 5 by adding dilute hydrochloric acid. Deposited crystals were separated by filtration, washed with a mixed solution of ethanol and water (2/1) and dried under reduced pressure to obtain 6-((4-benzoyloxy-1-pentane)sulfonylcarbamoyl)-1-(2,4dichlorobenzyl)-2-methyl-benzimidazole (15.54 g). This product was immediately subjected to the next step.

PRODUCTION EXAMPLE 17
<First Step>

Production of N-t-butyl-3-hydroxy-1-pentanesulfonamide

Under nitrogen atmosphere, a solution (520 ml) of 1.6 M n-butyl lithium in hexane was added slowly to a solution (480 ml) of diisopropylamine (120 ml) in tetrahydrofuran at −60 to −50° C. and the solution was stirred for 1 hour in an ice bath. The solution was cooled to −50° C. and a solution (100 ml) of N-t-butylmethane-sulfonamide (60.0 g) in tetrahydrofuran was added dropwise thereto taking 45 minutes. The temperature of the solution was raised to 0° C. taking 1 hour and the solution was stirred for 45 minutes in an ice bath. It was cooled to −40° C. and a solution (50 ml) of butylene oxide (42.9 g)in tetrahydrofuran was added thereto at −40 to −30° C. The temperature of the solution was raised slowly to room temperature and the solution was stirred overnight. The reaction was stopped by adding water in an ice bath. The solution was made acidic with dilute hydrochloric acid and the tetrahydrofuran layer was separated. The aqueous layer was extracted with chloroform. The tetrahydrofuran and aqueous layers were independently washed with saturated brine. The organic layers were combined, dried over sodium sulfate, and concentrated under reduced pressure. To the residue thus obtained was added t-butyl methyl ether (89 g). Crystallization was initiated by further adding hexane (200 ml). The crystals were collected by filtration, washed with a small amount of a mixed solution of t-butyl methyl ether and hexane (½), and dried under reduced pressure. Thus, N-t-butyl-3-hydroxy-1-pentanesulfonamide (60.6 g) was obtained.

[Physicochemical Property of Compound]

$^1$H-NMR (CDCl$_3$, δ ppm): 0.97(3H, t, J=7.4 Hz), 1.38 (9H, s), 1.46–1.57(2H, m), 1.80(1H, d, J=5.1 Hz), 1.81–1.89 (1H, m), 2.00–2.07(1H, m), 3.14–3.30(2H, m), 3.68(1H, m), 4.20(1H, s).

<Second Step>

Production of N-t-butyl-3-benzoyloxy-1-pentanesulfonamide

Under nitrogen atmosphere, N,N'-carbonyldiimidazole (90.0 g) was added to a solution of benzoic acid (67.7 g) in tetrahydrofuran (400 ml) in an ice bath and the solution was stirred for 1 hour at room temperature. N-t-butyl-3-hydroxy-1-pentanesulfonamide (59.0 g) was added thereto at room temperature. Subsequently, diazabicycloundecene (84.5 g) was added thereto in an ice bath. The mixture was stirred overnight at room temperature. About ½ volume of tetrahydrofuran was removed under reduced pressure. The reaction solution was made acidic with dilute hydrochloric acid in an ice bath and extracted with chloroform. The organic layer was washed with saturated aqueous solution of sodium hydrogencarbonate. Deposited solid was separated by filtration. After washing the organic layer with saturated brine and drying it over sodium sulfate, the solvent was removed under reduced pressure to obtain N-t-butyl-3-benzoyloxy-1-pentanesulfonamide (90.42 g) as oil.

[Physicochemical Property of the Compound]

$^1$H-NMR (CDCl$_3$, δ ppm): 0.97(3H, t, J=7.5 Hz), 1.33 (9H, s), 1.67–1.81(2H, m), 2.13–2.26(2H, m), 3.12(2H, m), 4.66(1H, s), 5.15(1H, m), 7.44(2H, m), 7.56(1H, m), 8.01–8.04(2H, m).

<Third Step>

Production of 3-Benzoyloxy-1-pentanesulfonamide

A mixture of N-t-butyl-3-benzoyloxy-1-pentanesulfonamide (90.4 g) and trifluoroacetic acid (200 ml) was stirred overnight at room temperature. Trifluoroacetic acid was removed under reduced pressure and water and chloroform were added to the residue. A saturated aqueous solution of sodium hydrogencarbonate was added thereto with vigorously stirring until the aqueous layer became neutral. After extraction with chloroform, the organic layer was washed with saturated brine, dried over sodium sulfate, and concentrated under reduced pressure. The residue was purified by silica gel column chromatography (eluate: hexane/ethyl acetate=2/1 to 1/1) to obtain 3-benzoyloxy-1-pentanesulfonamide (60.6 g) as oil.

[Physicochemical Property of the Compound]

$^1$H-NMR(CDCl$_3$, δ ppm): 0.99(3H, t, J=7.5 Hz), 1.77(2H, m), 2.26(2H, m), 3.22(2H, t, J=8.0 Hz), 4.77(2H, s), 5.19 (1H, m), 7.46(2H, t), 7.59(1H, t), 8.04(2H, dd, J=1.3 and 8.3 Hz).

<Fourth Step>

Production of Sodium Salt of 6-((3-Benzoyloxy-1-pentane)-sulfonylcarbamoyl)-1-(2,4-dichlorobenzyl)-2-methylbenzimidazole N,N'-carbonyldiimidazole (10.48 g) was added to an N,N-dimethylformamide solution (150 ml) of 6-carboxy-1-(2,4-dichlorobenzyl)-2-methylbenzimidazole (19.65 g) as obtained in Production Example 14 and the solution was stirred for 1 hour at room temperature. 3-Benzoyloxy-1-pentanesulfonamide (21.0 g) and diazabicycloundecene (9.40 g) were added and the solution was stirred overnight at 80° C. The solvent was removed under reduced pressure. Water was added to the residue to make the solution homogeneous and the pH was adjusted to about 6 by adding hydrochloric acid. Water was added and the solution was extracted with ethyl acetate. The organic layer was concentrated under reduced pressure. Ethyl acetate and a saturated aqueous solution of sodium hydrogencarbonate were added to the resulting residue and the solution was stirred for 4 hours. The solid deposited was separated by filtration, washed with water and ethyl acetate, and dried under reduced pressure to obtain sodium salt of 6-((3-benzoyloxy-1-pentane)sulfonylcarbamoyl)-1-(2,4-dichloro-benzyl)-2-methylbenzimidazole (18.90 g).

[Physicochemical Properties of the Compound]

$^1$H-NMR (DMSO-d6, δ ppm): 0.83(3H, t, J=7.1 Hz), 1.64(2H, m), 1.99(2H, m), 2.47(3H, m), 3.09(2H, m), 5.03 (1H, m), 5.51(2H, s), 6.40(1H, d, J=8.3 Hz), 7.28(1H, d, J=8.1 Hz), 7.49(3H, m), 7.63(1H, t), 7.70(1H, s), 7.85(2H, m), 7.94(2H, d, J=7.5 Hz).

EXAMPLE 1

Synthesis of 1-(Isoquinolin-3-ylmethyl)-2-methyl-6-(1-pentane-sulfonylcarbamoyl)benzimidazole (13)

N,N'-carbonyldiimidazole (0.324 g) was added to a solution of 6-carboxy-1-(isoquinolin-3-ylmethyl)-2-methylbenzimidazole (0.413 g) as obtained in Production Example 5 in N,N-dimethylformamide (10 ml) all at once and the mixture was stirred at room temperature for 1.5 hour. Then, 1-pentanesulfonamide (0.302 g) and diazabicycloundecene (0.304 g) were added thereto, and the resulting mixture was stirred at 100° C. for 6.5 hour. The reaction solution was concentrated, brine was added to the concentrate, and the mixture was extracted with chloroform. The organic layer was concentrated and the residue was purified by silica gel column chromatography (eluate: methanol/chloroform=1/19) followed by recrystallization from hexane/ethyl acetate (2/3) to yield the desired compound, 1-(isoquinolin-3-ylmethyl)-2-methyl-6-(1-pentanesulfonyl-carbamoyl)benzimidazole (13) (0.142 g).

[Physicochemical Properties of Compound (13)]

$^1$H-NMR (DMSO-d6, δ ppm) : 0.76(3H, t, J=7.3 Hz), 1.22(2H, m), 1.33(2H, m), 1.65(2H, m), 2.65(3H, s), 3.47 (2H, t, J=7.7 Hz), 5.74(2H, s), 7.64(2H, m), 7.76(2H, m), 7.92(1H, d, J=8.2 Hz), 8.09(1H, d, J=8.2 Hz), 8.23(1H, d, J=1.2 Hz), 9.27(1H, s), 11.86(1H, brs). IR(Nujol): 1674 cm$^{-1}$. mp: 209–212° C.

EXAMPLE 2

Synthesis of 1-((4-Chloroisoquinolin-3-ylmethyl)-2-methyl-6-(1-pentanesulfonylcarbamoyl) benzimidazole (14)

In the same manner as in Example 1, the desired benzimidazole (14) was obtained using the carboxylic acid as obtained in Production Example 6 and 1-pentanesulfonamide.

[Physicochemical Properties of Compound (14)]
$^1$H-NMR (DMSO-d6, δ ppm): 0.76(3H, t, J=7.3 Hz), 1.22(2H, m), 1.31(2H, m), 1.64(2H, m), 2.56(3H, s), 3.45 (2H, t, J=7.9 Hz), 5.92(2H, s), 7.62(1H, d, J=7.5 Hz), 7.75(1H, m), 7.80(1H, t, J=7.7 Hz), 8.00(1H, t, J=7.7 Hz), 8.10(1H, s), 8.16(1H, d, J=8.1 Hz), 8.27(1H, d, J=8.5 Hz), 9.12(1H, s), 11.84(1H, brs). IR(Nujol): 1677 cm$^{-1}$. mp: 209–210° C.

EXAMPLE 3

Synthesis of 1-((1-Bromonaphthalen-2-yl)methyl)-2-methyl-6-(1-pentanesulfonynylcarbamoyl) benzimidazole (15)

In the same manner as in Example 1, the desired benzimidazole (15) was obtained using the carboxylic acid as obtained in Production Example 7 and 1-pentanesulfonamide.

[Physicochemical Properties of Compound (15)]
$^1$H-NMR (DMSO-d6, δ ppm): 0.78(3H, t, J=7.3 Hz), 1.19–1.28(2H, m), 1.28–1.35(2H, m), 1.61–1.68(2H, m), 2.51(3H, s), 3.47(2H, t, J=7.8 Hz), 5.81(2H, s), 6.51(1H, d, J=8.6 Hz), 7.63(1H, t, J=7.7 Hz), 7.71(1H, d, J=8.5 Hz), 7.75(1H, t, J=7.2 Hz), 7.82(1H, d, J=8.4 Hz), 7.86(1H, d, J=8.6 Hz), 7.95(1H, d, J=8.1 Hz), 8.15(1H, s), 8.31(1H, d, J=8.6 Hz), 12.15(1H, s). IR(Nujol): 1688 cm$^{-1}$. mp: 260–263° C.

EXAMPLE 4

Synthesis of 1-(2,4-dichlorobenzyl)-6-((2-hydroxy-1-pentane-sulfonynylcarbamoyl)-2-methylbenzimidazole (16)

In the same manner as in Example 1, the desired benzimidazole (16) was obtained using the carboxylic acid as obtained in Production Example 14 and 2-hydroxy-1-pentanesulfonamide.

[Physicochemical Properties of Compound (16)]
$^1$H-NMR(DMSO-d6, δ ppm): 0.82(3H, t, J=7.3 Hz), 1.22–1.51(4H, m), 2.49(3H, s), 3.51(1H, dd, J=14.5 and 4.1 Hz), 3.61(1H, dd, J=14.5 and 7.3 Hz), 3.95(1H, m), 4.91(1H, m), 5.58(2H, s), 6.43(1H, d, J=8.4 Hz), 7.32(1H, dd, J=8.4 and 2.1 Hz), 7.68(1H, d, J=8.5 Hz), 7.77(1H, m), 7.80(1H, d, J=8.4 Hz), 8.10(1H, s), 11.77(1H, brs). $^1$H-NMR(CD$_2$Cl$_2$, δ ppm): 0.90(3H, t, J=7 Hz), 1.30–1.80(4H, m), 2.56(3H, s), 3.6–3.7(3H, m), 5.43(2H, s), 6.37(1H, d, J=8 Hz), 7.12(1H, dd, J=8 and 2 Hz), 7.52(1H, d, J=2 Hz), 7.69(1H, dd, J=8 and 2 Hz), 7.76–7.79(2H, m). IR(Nujol): 1684, 1670 cm$^{-1}$. Mass: m/e 484(M+1). mp: 228–230° C.

EXAMPLE 4-2

Production of 1-(2,4-Dichlorobenzyl)-6-((2-hydroxy-1-pentane)-sulfonylcarbamoyl)-2-methylbenzimidazole (16)

6-((2-Benzoyloxy-1-pentane)sulfonylcarbamoyl)-1-(2,4-dichlorobenzyl)-2-methylbenzimidazole (10.00 g) as obtained in Production Example 15 was dissolved in methanol (450 ml) by heating the mixture and cooled to room temperature. A 10% aqueous solution of sodium hydroxide (7 ml) was added to this solution and stirred for 1 hour at room temperature. Then, a 10% aqueous solution of sodium hydroxide (13.4 ml) was added and stirred for 80 minutes at 50° C. under heating. While cooling the reaction solution with ice, 1N hydrochloric acid (about 50 ml) was slowly added thereto to adjust to pH 4–5 and methanol (about 300 ml) was removed under reduced pressure. The resulting concentrated reaction solution (about 150 ml) was cooled with ice and deposited crystals were collected by filtration and washed successively with water (50 ml) and chloroform (50 ml). After drying the crystals by heating under reduced pressure, aceton (450 ml) was added thereto and reflux was conducted for 30 minutes. The solution was again cooled to ice temperature. Crystals were collected by filtration and dried by heating under reduced pressure. Thus, 1-(2,4-dichlorobenzyl)-6-((2-hydroxy-1-pentane) sulfonylcarbamoyl)-2-methylbenzimidazole (16) (6.69 g) was obtained.

[Physicochemical Properties of Compound (16)]
$^1$H-NMR(DMSO-d6, δ ppm): 0.82(3H, t, J=7.2 Hz), 1.26–1.46(4H, m), 2.49(3H, s), 3.51(1H, dd, J=14.5 and 4.1 Hz), 3.61(1H, dd, J=14.5 and 7.3 Hz), 3.96(1H, brs), 4.91 (1H, brs), 5.58(2H, s), 6.43(1H, d, J=8.4 Hz), 7.32(1H, dd, J=8.4 and 1.8 Hz), 7.68(1H, d, J=8.4 Hz), 7.75(1H, d, J=1.1 Hz), 7.80(1H, d, J=8.4 Hz), 8.10(1H, s), 11.77(1H, brs). IR(Nujol): 1684 cm$^{-1}$. mp: 224.0–224.4° C.

EXAMPLE 5

Synthesis of 1-(2,4-Dichlorobenzyl)-6-((4-hydroxy-1-pentane)-sulfonynylcarbamoyl)-2-methylbenzimidazole (17)

In the same manner as in Example 1, the desired benzimidazole (17) was obtained using the carboxylic acid as obtained in Production Example 14 and (4-hydroxy-1-pentane)sulfonamide.

[Physicochemical Properties of Compound (17)]
$^1$H-NMR (CD$_2$Cl$_3$, δ ppm): 1.15(3H, t, J=7 Hz), 1.55(2H, m), 1.90(2H, m), 2.58(3H, s), 3.60(2H, m), 3.80(1H, m), 5.44(2H, s), 6.37(1H, d, J=8 Hz), 7.12(1H, dd, J=8 and 2 Hz), 7.52(1H, d, J=2 Hz), 7.70(1H, dd, J=8 and 2 Hz), 7.76–7.79(2H, m), 8.40(1H, brs).$^1$NMR (DMSO-d6, δ ppm): 0.99(3H, d, J=6.2 Hz), 1.37–1.47(2H, m), 1.66–1.80 (2H, m), 2.49(3H, s), 3.50(1H, t, J=7.8 Hz), 3.55(1H, m), 5.58(2H, s), 6.43(1H, d, J=8.3 Hz), 7.32(1H, dd, J=8.4 and 2.1 Hz), 7.67(1H, d, J=8.4 Hz), 7.75(1H, d, J=2.0 Hz), 7.80(1H, d, J=8.4 Hz), 8.10(1H, s), 11.84(1H, brs). IR(Nujol): 1694 cm$^{-1}$. mp: 186.7–187.6° C. Mass: m/e 484(M+1).

EXAMPLE 5-2

Production of 1-(2,4-Dichlorobenzyl)-6-((4-hydroxy-1-pentane)-sulfonylcarbamoyl)-2-methylbenzimidazole (17)

A mixture of 6-((4-benzoyloxy-1-pentane)sulfonyl-carbamoyl)-1-(2,4-dichlorobenzyl)methylbenzimidazole (15.0 g) as obtained in Production Example 16, sodium hydroxide (4.08 g), ethanol (80 ml), and water (120 ml) was stirred for 2 hours at 80° C. After neutralizing the reaction solution with hydrochloric acid, water was added thereto and extraction with ethyl acetate was carried out. The organic layer was washed twice with water, dried, and concentrated. To the residue thus obtained were added acetone (50 ml) and diethyl ether (75 ml). Deposited crystals were collected by filtration, washed with diethyl ether, and dried to obtain white crystals (4.2 g). Following the same method, white crystals (3.0 g) were obtained from 6-((4-benzoyloxy-1-pentane)sulfonyl carbamoyl)-1-(2,4-dichlorobenzyl)methylbenzimidazole (5.0 g). The crystals were combined (7.2 g) and a mixed solvent of acetone and water (acetone/water=9/1, 150 ml) was added thereto and heated to 60° C. to dissolve the crystals. Water (400 ml) was added at 60° C., the solution was stirred for 1 hour and cooled slowly to room temperature. Deposited crystals were collected by filtration and dried to obtain 1-(2,4-dichlorobenzyl)-6-((4-hydroxy-1-pentane)sulfonyl-carbamoyl)-2-methylbenzimidazole (17) (6.2 g).

[Physicochemical Properties of Compound (17)]

$^1$H-NMR (DMSO-d6, δ ppm): 0.99(3H, d, J=6.2 Hz), 1.37–1.47(2H, m), 1.66–1.80(2H, m), 2.49(3H, s), 3.50(1H, t, J=7.8 Hz), 3.55(1H, m), 5.58(2H, s), 6.43(1H, d, J=8.3 Hz), 7.32(1H, dd, J=8.4 and 2.1 Hz), 7.67(1H, d, J=8.4 Hz), 7.75(1H, d, J=2.0 Hz), 7.80(1H, d, J=8.4 Hz), 8.10(1H, s), 11.84(1H, brs). IR(Nujol): 1694 cm$^{-1}$. mp: 186.7–187.60° C.

EXAMPLE 6

Synthesis of 1-(2,4-Dichlorobenzyl)-6-((3-hydroxy-1-pentane)-sulfonynylcarbamoyl)-2-methylbenzimidazole (18)

In the same manner as in Example 1, the desired benzimidazole (18) was obtained using the carboxylic acid as obtained in Production Example 14 and (3-hydroxy-1-pentane)sulfonamide.

[Physicochemical Properties of Compound (18)]

$^1$H-NMR (CD$_2$C$_2$, δ ppm): 0.92(3H, t, J=7 Hz), 1.40–1.90 (4H, m), 2.57(3H, s), 3.6–3.8(3H, m), 5.44(2H, s), 6.36(1H, d, J=8 Hz), 7.11(1H, dd, J=8 and 2 Hz), 7.53(1H, d, J=2 Hz), 7.69(1H, dd, J=8 and 2 Hz), 7.76–7.79(2H, m), 8.40(1H, brs). $^1$NMR (DMSO-d6, δ ppm): 0.80(3H, t, J=7.3 Hz), 1.25–1.40(2H, m), 1.64(1H, m), 1.79(1H, m), 2.49(3H, s), 3.37–3.48(1H, m), 3.58(1H, m), 4.64(1H, m), 5.58(2H, s), 6.43(1H, d, J=8.4 Hz), 7.32(1H, d, J=8.3 Hz), 7.67(1H, d, J=8.3 Hz), 7.75(1H, s), 7.80(1H, d, J=8.3 Hz), 8.09(1H, s), 11.85(1H, brs). IR(Nujol): 1694 cm$^{-1}$. mp: 205.5–206.0° C. Mass: m/e 484(M+1).

EXAMPLE 6-2

Production of 1-(2,4-Dichlorobenzyl)-6-((3-hydroxy-1-pentane)-sulfonylcarbamoyl)-2-methylbenzimidazole (18)

An aqueous solution (65 ml) of sodium hydroxide (2.03 g) and methanol (105 ml) were added to sodium salt of 6-((3-benzoyloxy-1-pentane)-sulfonylcarbamoyl-1-(2,4-dichlorobenzyl)-2-methyl-benzimidazole (15.55 g, 25.47 mmol) as obtained in Production Example 17 and stirred for 6.5 hour at 60° C. The reaction solution was cooled to room temperature, neutralized (pH 5) with hydrochloric acid, and extracted with chloroform. Solid obtained by removing the solvent was dissolved in a mixed solvent of water (50 ml) and methanol (160 ml) under heating. About ½ volume of methanol was removed under reduced pressure and the solution obtained was allowed to stand for one day. Deposited crystals were collected by filtration and dried to obtain 1-(2,4-dichlorobenzyl)-6-((3-hydroxy-1-pentane)-sulfonylcarbamoyl)-2-methylbenzimidazole (18) (9.00 g).

[Physicochemical Properties of Compound (18)]

$^1$H-NMR(DMSO-d6, δ ppm): 0.80(3H, t, J=7.3 Hz), 1.25–1.40(2H, m), 1.64(1H, m), 1.79(1H, m), 2.49(3H, s), 3.37–3.48(1H, m), 3.58(1H, m), 4.64(1H, m), 5.58(2H, s), 6.43(1H, J=8.4 Hz), 7.32(1H, d, J=8.3 Hz), 7.67(1H, d, J=8.3 Hz), 7.75(1H, s), 7.80(1H, d, J=8.3 Hz), 8.09(1H, s), 11.85(1H, brs). IR(Nujol): 1694 cm$^{-1}$. mp: 205.5–206.0° C.

EXAMPLE 7

Synthesis of 1-(2,4-Dichlorobenzyl)-2-methyl-6-(((E)-1-pent-1-en)sulfonynylcarbamoyl) benzinidazole (19)

In the same manner as in Example 1, the desired benzimidazole (19) was obtained using the carboxylic acid as obtained in Production Example 14 and (1-pent-1-en) sulfonamide.

[Physicochemical Properties of Compound (19)]

$^1$H-NMR (CD$_3$OD, δ ppm): 0.85(3H, t, J=7.4 Hz), 1.44 (2H, m), 2.18(2H, m), 2.51(3H, s), 5.52(2H, s), 6.48(1H, d, J=8.4 Hz), 6.59(1H, m), 6.91(1H, m), 7.14(1H, dd, J=8.4 and 2.2 Hz), 7.51(1H, d, J=2.0 Hz), 7.61(1H, d, J=8.5 Hz), 7.73(1H, dd, J=8.5 and 1.6 Hz), 7.87(1H, s). IR(Nujol): 1674 cm$^{-1}$. mp: 243–245° C.

EXAMPLE 8

Synthesis of 6-(Benzenesulfonylcarbamoyl)-1-(2,4-dichloro-benzyl)-2-methylbenzimidazole (20)

In the same manner as in Example 1, the desired benzimidazole (20) was obtained using the carboxylic acid as obtained in Production Example 14 and benzenesulfonamide.

[Physicochemical Property of Compound (20)]

$^1$H-NMR (DMSO-d6): 2.50(3H,s), 5.58(2H,s), 6.41(1H, d,J=8.5 Hz), 7.31(1H,d,J=8.4 Hz), 7.59–7.76(6H,m), 7.98 (2H,d,J=7.9 Hz), 8.06(1H,s), 12.38(1H,brs). IR: 1684 cm$^{-1}$. mp: 230.5–234.0° C.

EXAMPLE 9

Synthesis of 6-(N'-butanesulfonylhydrazinocarbamoyl)-1-(2,4-dichlorobenzyl)-2-methylbenzimidazole (21)

In dehydrated dichloromethane (5.0 ml) were dissolved 1-(2,4-dichlorobenzyl)-6-(hydrozinocarbonyl)-2-methylbenzimidazole (246 mg) as obtained in Production Example 8 and triethylamine (0.196 ml). n-Butanesulfonyl chloride was further added dropwise thereto at room temperature. After stirring for 2 hours, the reaction mixture was extracted using chloroform and water. The organic layer was dried over magnesium sulfate and evaporated to dryness under reduced pressure. The resulting residue was purified by thin-layer chromatography (chloroform/methanol =30/1 as a developing solvent) and further by recrystal on from ethyl acetate to yield 6-(N'-butanesulfonylhydrazinocarbamoyl)-1-(2,4-dichlorobenzyl)-2-methylbenzimidazole (21) (76 mg) as colorless crystals.

[Physicochemical Properties of Compound 21]

mp: 208–210° C.

$^1$H-NMR (DMSO-d6): 0.97(3H, t, J=6 Hz), 1.53(2H, m), 1.92(2H, m), 2.60(3H, s), 3.55(2H, t, J=Hz), 5.42(2H, s), 6.30(1H, d, J=8 Hz), 7.10(1H, d, J=8 Hz), 7.52(1H, s), 7.72(1H, s), 7.84(2H, s).

EXAMPLE 10

Synthesis of 6-((N-butylaminosulfonyl)carbamoyl)-1-(2,4-dichlorobenzyl)-2-methylbenzimidazole (22)

In the same manner as in Production Example 8, 6-((n-butylaminosulfonyl)carbamoyl)-1-(2,4-dichlorobenzyl)-2- methyl-benzimidazole (22) was obtained as colorless crystals (271 mg) from 6-carboxy-1-(2,4-dichlorobenzyl)-2-methylbenzimidazole (200 mg) and N-(n-butyl)sulfamide (182 mg).
[Physicochemical Property of Compound (22)]
$^1$H-NMR (DMSO-d6): 0.78(3H, t, J=6 Hz), 1.24(2H, m), 1.42(2H, m), 2.52(3H, s), 2.90(2H, m), 5.59(2H, s), 6.48 (1H, d, J=8 Hz), 7.33(1H, d, J=8 Hz), 7.64–7.83(4H, m), 8.08(1H, s).

EXAMPLE 11

Synthesis of 1-(2,4-Dichlorobenzyl)-2-methyl-6-[N'-(4-methyl-phenylsulfonyl)ureido]benzimidazole (23)

6-Amino-1-(2,4-dichlorobenzyl)-2-methylbenzimidazole (60 mg) as obtained in Production Example 10 was dissolved in dehydrated 1,4-dioxane (1.0 ml) and (4-methylphenylsulfonyl)isocyanate (46 mg) was further added thereto. After the mixture was stirred at room temperature for 1 hour, crystals precipitated were collected by filtration and washed with 1,4-dioxane to obtain 1-(2,4-dichlorobenzyl)-2-methyl-6-[N'-(4-methylphenylsulfonyl) ureido]-benzimidazole (23) as white powder (95 mg).
[Physicochemical Property of Compound (23)]
$^1$H-NMR (DMSO-d6): 2.37(3H, s), 2.42(3H, s), 5.42(2H, s), 6.46(1H, d, J=8 Hz), 7.00(1H, d, J=8 Hz), 7.29(1H, d, J=8 Hz), 7.35–7.47(4H, m), 7.70(1H, s), 7.80(2H, d, J=8 Hz), 8.76(1H, s).

EXAMPLE 12

Synthesis of 1-(2,4-Dichlorobenzyl)-2-methyl-6-(N'-phenyl-ureido)benzinidazole (24)

In the same manner as in Example 11, 1-(2,4-dichlorobenzyl)-2-methyl-6-(N'-phenylureido) benzimidazole (24) (177 mg) was obtained from 6-amino-1-(2,4-dichlorobenzyl)-2-methylbenzimidazole (157 mg) and phenylisocyanate (0.06 ml).
[Physicochemical Property of Compound (24)]
$^1$H-NMR (DMSO-d6): 2.44(3H, s), 5.44(2H, s), 6.50(1H, d, J=8 Hz), 6.93(1H, t, J=8 Hz), 7.08(1H, d, J=8 Hz), 7.25(2H, t, J=8 Hz), 7.34(1H, d, J=8 Hz), 7.41(2H, d, J=8 Hz), 7.49(1H, d, J=8 Hz), 7.59(1H, s), 7.75(1H, s), 8.58(1H, s), 8.67(1H, s).

EXAMPLE 13

Synthesis of 1-(2-Chloro-4-(trifluoromethyl) benzyl)-2-methyl-6-(1-pentanesulfonylcarbamoyl) benzimidazole (25)

In the same manner as in Example 1, 1-(2-chloro-4-(trifluoromethyl)benzyl)-2-methyl-6-(1-pentanesulfonyl-carbamoyl)benzimidazole (25) was obtained as white crystals (210 mg) from 6-carboxy-1-(2-chloro-4-(trifluoromethyl)benzyl)-2-methyl-benzimidazole (200 mg) as obtained in Production Example 13 and 1-pentanesulfonamide (123 mg).
[Physicochemical Properties of Compound (25)]
$^1$H-NMR (DMSO-d6): 0.90(3H, t, J=8 Hz), 1.20–1.40 (4H, m), 1.62–1.72(2H, m), 2.50(3H, s), 3.49(2H, t, J=8 Hz), 5.70(2H, s), 6.56(1H, d, J=8 Hz), 7.62(1H, d, J=8 Hz), 7.70(1H, d, J=8 Hz), 7.82(1H, d, J=8 Hz), 8.13(1H, s), 8.12(1H, s). Mass(ESI): m/z 500(M-H).

EXAMPLE 14

Synthesis of 1-(2-Chloro-4-(trifluoromethyl) benzyl)-2-methyl-6-(((E)-1-pent-1-en) sulfonylcarbamoyl)benzimidazole (26)

In the same manner as in Example 1, 1-(2-chloro4-(trifluoromethyl)benzyl)-2-methyl-6-(((E)-1-pent-en) sulfonyl-carbamoyl)benzimidazole (26) was obtained as white crystals (192 mg) using 6-carboxy-1-(2-chloro-4-(trifluoromethyl)benzyl)-2-methyl-benzimidazole (200 mg) as obtained in Production Example 13 and (1-penta-1-en) sulfonamide (121 mg).
[Physicochemial Properties of Compound (26)]
$^1$H-NMR(DMd6): 0.84(3H, t, J=8 Hz), 1.36–1.49(2H, m), 2.21(2H, q, J=7 Hz), 2.50(3H, s), 5.67(2H, s), 6.54(1H, d, J=8 Hz), 6.73(1H, d, J=14 Hz), 6.80–6.90(1H, m), 7.60(1H, d, J=8 Hz), 7.68(1H, d, J=8 Hz), 7.78(1H, d, J=8 Hz), 8.00(1H, s), 8.07(1H, s). Mass(ESI): m/z 498(M-H).

EXAMPLE 15

Synthesis of 1-(2,4-Dichlorobenzyl)-2-methyl-6-((E)-2-phenyl-ethenylsulfonylcarbamoyl) benzimidazole (27)

In the same manner as in Example 1, the desired benzimidazole (27) was obtained using the carboxylic acid as obtained in Production Example 14 and (E)-2-phenylethenylsulfonarnide.
[Physicochemical Properties of Compound (27)]
$^1$H-NMR (DMSO-d6, δ ppm): 2.48(3H, s), 5.57(2H, s), 6.42(1H, d, J=8.4 Hz), 7.31(1H, d, J=8.4 Hz), 7.41–7.52(4H, m), 7.61–7.68(2H, m), 7.72–7.82(4H, m), 8.11(1H, s), 12.17 (1H, brs). IR(Nujol): 1674 cm$^{-1}$. mp: 291–293° C.

PRODUCTION EXAMPLE 18

<First Step>

Production of Ethyl 4-(acetylamino)-3-((2-chloro-4-phenyl-benzyl)amino)benzoate

In the same manner as in Production Example 1, the desired compound (3.10 g) was obtained from ethyl 4-(acetylamino)-3-aminobenzoate (2.22 g), 2-chloro-4-phenylbenzyl bromide (3.37 g), and potassium carbonate (1.66 g).
[Physicochemical Property of the Compound]
$^1$H-NMR (CDCl$_3$, δ ppm): 1.36(3H, t, J=7.1 Hz), 1.92 (1H, brs), 2.23(3H, s), 4.2–4.6(5H, m), 7.37(1H, t, J=7.3 Hz), 7.41–7.58(9H, m), 7.64(1 H, s).

<Second and Third Steps>

Production of 6-Carboxy-1-(2-chloro-4-phenylbenzyl)-2-methyl-benzimidazole

Following the methods of Production Example 3 and Production Example 5 successively, the desired compound (2.50 g) was obtained from ethyl 4-(acetylamino)-3-((2-chloro-4-phenylbenzyl)amino)-benzoate (3.00 g) via 1-(2-chloro-4-phenylbenzyl)-6-(ethoxycarbonyl)-2-methylbenzimidazole.
[Physicohemnical Property of the Compound]
$^1$H-NMR (DMSO-d6, δ ppm): 2.68(3H, s), 7.76(2H, s), 6.79(1H, d, J=8.1 Hz), 7.38(1H, t, J=7.2 Hz), 7.45(2H, t), 7.56(1H, dd, J=1.7 and 8.1 Hz), 7.67(2H, d, J=7.4 Hz), 7.76(1H, d, J=8.5 Hz), 7.86(1H, d, J=1.7 Hz), 7.93(1H, d, J=8.5 Hz), 13.0(1H, brs).

EXAMPLE 16

Synthesis of 1-(2-Chloro-4-phenylbenzyl)-2-methyl-6-(1-pentanesulfonylcarbamoyl)benzimidazole (28)

In the same manner as in Example 1, the desired benzimidazole (28) was obtained using the carboxylic acid as obtained in Example 18 and 1-pentanesulfonamide.
[Physicochemical Properties of Compound (28)]

¹H-NMR (DMSO-d6, δ ppm): 0.80(3H, t, J=7.3 Hz), 1.20–1.28(2H, m), 1.31–1.38(2H, m), 1.63–1.71(2H, m), 2.54(3H, s), 3.49(2H, t, J=7.7 Hz), 5.65(2H, s), 6.50(1H, d, J=8.2 Hz), 7.39(1H, t, J=7.1 Hz), 7.46(2H, t, J=7.6 Hz), 7.54(1H, dd, J=8.0 and 1.6 Hz), 7.66(2H, d, J=7.5 Hz), 7.70(1H, d, J=8.6 Hz), 7.81(1H, dd, J=8.5 and 1.3 Hz), 7.87(1H, d, J=1.8 Hz), 8.15(1H, s), 11.89(1H, s). IR(Nujol): 1683 cm$^{-1}$. mp: 210–212.5C.

EXAMPLE 17

Synthesis of 1-(2-Chloro-4-phenylbenzyl)-2-methyl-6-(((E)- 1-pent-1-en)sulfonylcarbamoyl) benzimidazole (29)

In the same manner as in Example 1, the desired benzimidazole (29) was obtained using the carboxylic acid as obtained in Production Example 18 and (1-pent-1-en) sulfonamide.
[Physicochemical Properties of Compound (29)]
¹H-NMR (DMSO-d6, δ ppm): 0.84(3H, t, J=7.3 Hz), 1.38–1.47(2H, m), 2.21(2H, quartet, J=7.0 Hz), 2.52(3H, s), 5.63(2H, s), 6.47(1H, d, J=8.1 Hz), 6.75(1H, d, J=15.2 Hz), 6.82–6.88(1H, m), 7.38(1H, t, J=7.2 Hz), 7.45(2H, t, J=7.6 Hz), 7.52(1H, d, J=8.0 Hz), 7.65(2H, d, J=7.8 Hz), 7.68(1H, d, J=8.6 Hz), 7.78(1H, d, J=8.6 Hz), 7.86(1H, s), 8.12(1H, s), 12.00(1H, brs). IR(Nujol): 1672 cm$^{-1}$. mp: 234–235° C.

EXAMPLE 18

Synthesis of 1-(2-Chloro-4-phenylbenzyl)-2-methyl-6-((4-methyl-benzene)sulfonylcarbamoyl) benzimidazole (30)

In the mn manner as in Example 1, the desired benzimidazole (30) was obtained using the carboxyl add as obtained in Production Example 18 and (4-methylbenzene) sulfonamide.
[Physicochemical Properties of Compound (30)]
¹H-NMR(DMSO-d6, δ ppm): 2.35(3H, s), 2.51(3H, s), 5.63(2H, s), 6.46(1H, d, J=8.1 Hz), 7.37–7.40(3H, m), 7.45(2H, t, J=7.6 Hz), 7.51(1H, dd, J=8.0 and 1.6 Hz), 7.63–7.67(3H, m), 7.72(1H, dd, J=8.5 and 1.4 Hz), 7.83–7.87(3H, m), 8.08(1H, d, J=1.2 Hz), 12.33(1H, brs). IR(Nujol): 1682 cm$^{-1}$. mp: 251.8–252.3° C.

EXAMPLE 19

Synthesis of 1-(2-Chloro-4-phenylbenzyl)-2-methyl-6-((E)-phenylethenylsulfonylcarbamoyl) benzimidazole (31)

In the same manner as in Example 1, the desired benzimidazole (31) was obtained using the carboxylic acid as obtained in Production Example 18 and ((E)-2-phenylethenyl)sulfonamide.
[Physicochemical Properties of Compound (31)]
¹H-NMR (DMSO-d6, δ ppm): 2.52(3H, s), 5.63(2H, s), 6.46(1H, d, J=8.1 Hz), 7.36–7.47(6H, m), 7.50(1H, s), 7.51(1H, d, J=8.7 Hz), 7.60(1H, d, J=15.5 Hz), 7.64(2H, d, J=8.6 Hz), 7.67(1H, d, J=8.6 Hz), 7.73(2H, d, J=6.9 Hz), 7.80(1H, d, J=8.6 Hz), 7.85(1H, s), 8.15(1H, s), 12.15(1H, brs). IR(Nujol): 1677 cm$^{-1}$. mp: 267–268° C.

EXAMPLE 20

Synthesis of 1-(2-Chloro-4-phenylbenzyl)-6-((5-chlorothiophen-2-yl)sulfonylcarbamoyl)-2-methylbenzimidazole (32)

In the same manner as in Example 1, the desired benzimidazole (32) was obtained using the carboxylic acid as obtained in Production Example 18 and (5-chlorothiophen-2-yl)sulfonamide.
[Physicochemical Properties of Compound (32)]
¹H-NMR (DMSO-d6, δ ppm): 2.61(3H, s), 5.71(2H, s), 6.63(1H, d, J=7.8 Hz), 7.16(1H, d, J=4.0 Hz), 7.38(1H, t, J=7.2 Hz), 7.45(2H, t, J=7.6 Hz), 7.53(1H, d, J=8.1 Hz), 7.56(1H, brs), 7.66(2H, d, J=8.6 Hz), 7.70(1H, d, J=8.6 Hz), 7.86(1H, d, J=1.5 Hz), 7.89(1H, d, J=8.4 Hz), 8.13(1H, s). IR(Nujol): 1691 cm$^{-1}$. mp: 292–293° C.

PRODUCTION EXAMPLE 19

<First Step>

Production of Ethyl 4-(acetylamino)-3-((4-bromo-2-chlorobenzyl) amino)benzoate

In the same manner as in Production Example 1, the desired compound (3.00 g) was obtained from ethyl 4-(acetylamino)-3-aminobenzoate (2.22 g), 4-bromo-2-chlorobenzyl bromide (2.60 g), and potassium carbonate (1.66 g).
[Physicochemical Property of the Compound]
¹H-NMR (DMSO-d6, δ ppm): 1.23(3H, d, J=7.1 Hz), 2.10(3H, s), 4.18(2H, q, J=7.1 Hz), 4.39(2H, d, J=5.8 Hz), 6.05(1H, t, J=5.8 Hz), 6.89(1H, d, J=1.7 Hz), 7.19(1H, dd, J~=1.7 and 8.2 Hz), 7.35(1H, d, J=8.3 Hz), 7.40(1H, d, J=8.2 Hz), 7.50(1H, dd, J=1.8 and 8.3 Hz), 7.75(1H, d, J=1.7 Hz), 9.38(1H, s).

<Second and Third Steps>

Production of 1-(4-Bromo-2-chlorobenzyl)-6-carboxy-2-methyl benzimidazole

Following the methods of Production Example 3 and Production Example 5 successively, the desired compound (2.03 g) was obtained from ethyl 4-(acetylamino)-3-((4-bromo-2-chlorobenzyl)amino)-benzoate (3.00 g) via 1-(4-bromo-2-chlorobenzyl)-6-(ethoxycarbonyl)-2-methylbenzimidazole.
[Physicochemical Property of the Compound]
¹H-NMR (DMSO-d6, δ ppm): 2.50(3H, s), 5.58(2H, s), 6.45(1H, d, J=8.4 Hz), 7.45(1H, dd, J=2.0 and 8.4 Hz), 7.63(1H, d, J=8.4 Hz), 7.80(1H, dd, J=1.4 and 8.4 Hz), 7.84(1H, d J=2.0 Hz), 7.97(1H, d, J=1.4 Hz), 12.7(1H, brs).

EXAMPLE 21

Synthesis of 1-(4-Bromo-2-chlorobenzyl)-2-methyl-6-(((E)-1-pent-1-en)sulfonylcarbamoyl) benzimidazole (33)

In the same manner as in Example 1, the desired benzimidazole (33) was obtained using the carboxylic acid as obtained in Production Example 19 and (1-pent-1-en) sulfonamide.
[Physicochemical Properties of Compound (33)]
¹H-NMR (DMSO-d6, δ ppm): 0.85(3H, t, J=7.3 Hz), 1.40–1.47(2H, m), 2.22(2H, quartet, J=7.0 Hz), 2.48(3H, s), 5.55(2H, s), 6.34(1H, d, J=8.4 Hz), 6.75(1H, d, J=15.2 Hz), 6.82–6.88(1H, m), 7.44(1H, d, J=8.4 Hz), 7.66(1H, d, J=8.4 Hz), 7.77(1H, d, J=8.4 Hz), 7.85(1H, s), 8.06(1H, s), 11.95 (1H, brs). IR(Nujol): 1678 cm$^{-1}$. mp: 254–255° C.

EXAMPLE 22

Synthesis of 1-(4-Bromo-2-chlorobenzyl)-2-methyl-6-((4-methyl-benzene)sulfonylcarbamoyl) benzimidazole (34)

In the same manner as in Example 1, the desired benzimidazole (34) was obtained using the carboxylic acid as obtained in Production Example 19 and 4-methylbenzenesulfonamide.
[Physicochemical Properties of Compound (34)]
$^1$H-NMR (DMSO-d6, δ ppm): 2.37(3H, s), 2.47(3H, s), 5.54(2H, s), 6.32(1H, d, J=8.4 Hz), 7.40(2H, d, J=8.2 Hz), 7.43(1H, dd, J=8.5 and 1.8 Hz), 7.63(1H, d, J=8.5 Hz), 7.71(1H, d, J=8.4 Hz), 7.84–7.88(3H, m), 8.04(1H, s), 12.31(1H, brs). mp: 245–246° C.

EXAMPLE 23

Synthesis of 1-(4-Bromo-2-chlorobenzyl)-2-methyl-6-((E)-2-phenylethenylsulfonylcarbamoyl) benzimidazole (35)

In the same manner as in Example 1, the desired benzimidazole (35) was obtained using the carboxylic acid as obtained in Production Example 19 and ((E)-2-phenylethenyl)sulfonamide.
[Physicochemical Properties of Compound (35)]
$^1$H-NMR(DMSO-d6, δ ppm): 2.47(3H, s), 5.54(2H, s), 6.34(1H, d, J=8.4 Hz), 7.41–7.45(4H, m), 7.48(1H, d, J=15.5 Hz), 7.62(1H, d, J=15.4 Hz), 7.65(1H, d, J=8.5 Hz), 7.75 (2H, d, J=7.8 Hz), 7.79(1H, d, J=8.6 Hz), 7.85(1H, d, J=1.8 Hz), 8.10(1H, s), 12.18(1H, brs). IR(Nujol): 1672 cm$^{-1}$. mp: 292.5–293.5° C.

EXAMPLE 24

Synthesis of 1-(4-Bromo-2chlorobenzyl)-6-((5-chlorothiophen-2-yl)sulfonylcarbamoyl)-2-methylbenzimidazole (36)

In the same manner as in Example 1, the desired benzimidazole (36) was obtained using the carboxylic acid as obtained in Production Example 19 and (5-chlorothiophen-2-yl)sulfonamide.
[Physicochemical Properties of Compound (36)]
$^1$H-NMR(DMSO-d6, δ ppm): 2.55(3H, s), 5.62(2H, s), 6.48(1H, d, J=8.5 Hz), 7.18(1H, d. J=4.0 Hz), 7.44(1H, dd, J=8.3 and 1.8 Hz), 7.57(1H, s), 7.68(1H, d, J=8.6 Hz), 7.85–7.88(2H, m), 8.07(1H, s). IR(Nujol): 1692 cm$^{-1}$. mp: 308–309° C.

PRODUCTION EXAMPLE 20
<First, Second and Third Steps>

Production of 1-(4-(Benzyloxybenzyl)-2-chlorobenzyl)-6-carboxy-2-methylbenzimidazole Following the methods of Production Example 1, Production Example 3, and successively Production Example 5, the desired compound (0.50 g) was obtained from ethyl 4-(acetylamino)-3-aminobenzoate (0.74 g), 4-(benzyloxybenzyl)-2-chlorobenzyl chloride (1.07 g), potassium carbonate (0.55 g) and sodium iodide (0.25 g) via ethyl 4-(acetylamino)-3-((4-(benzyloxybenzyl)-2-chlorobenzyl)amino)benzoate and 1-(4-(benzyloxybenzyl)-2-chloro-benzyl)-6-(ethoxycarbonyl)-2-methylbenzimidazole.
[Physicochemical Property of the Compound]
$^1$H-NMR (DMSO-d6, δ ppm): 2.55(3H, s), 5.09(2H, s), 5.55(2H, s), 6.62(1H, d, J=8.8 Hz), 6.92(1H, dd, J=2.2 and 8.8 Hz), 7.22(1H, d, J=2.2 Hz), 7.29–7.42(5H, m), 7.63(1H, d, J=8.8 Hz), 7.80(1H, dd, J=1.3 and 8.8 Hz), 7.97(1H, s), 12.76(1H, brs).

EXAMPLE 25

Synthesis of 1-(4-Benzyloxy-2-chlorobenzyl)-2-methyl-6-(1-pentanesulfonylcarbamoyl) benzimidazole (37)

In the same manner as in Example 1, the desired benzimidazole (37) was obtained using the carboxylic acid as obtained in Production Example 20 and 1-pentanesulfonamide.
[Physicochemical Properties of Compound (37)]
$^1$H-NMR (DMSO-d6, δ ppm): 0.81(3H, t, J=7.2 Hz), 1.22–1.38(4H, m), 1.64–1.72(4H, m), 2.49(3H, s), 3.49(2H, t, J=7.7 Hz), 5.09(2H, s), 5.51(2H, s), 6.46(1H, d, J=8.7 Hz), 6.90(1H, dd, J=8.7 and 2.5 Hz), 7.24(1H, d, J=2.5 Hz), 7.31 (1H, t, J=7.0 Hz), 7.34–7.42(4H, m), 7.66(1H, d, J=8.4 Hz), 7.79(1H, d, J=8.4 Hz), 8.09(1H, s), 11.88(1H, brs). IR(Nujol): 1681 cm$^{-1}$. mp: 190.5–191.5° C.

EXAMPLE 26

Synthesis of 1-(4-Benzyloxy-2-chlorobenzy)-2-methyl-6-((4-methylbenzene)sulfonylcarbamoyl) benzimidazole (38)

In the same manner as in Example 1, the desired benzimidazole (38) was obtained using the carboxylic acid as obtained in Production Example 20 and (4-methylbenzene) sulfonamide.
[Physicochemical Properties of Compound (38)]
$^1$H-NMR (DMSO-d6, δ ppm): 2.37(3H, s), 2.47(3H, s), 5.08(2H, s), 5.49(2H, s), 6.43(1H, d, J=8.7 Hz), 6.88(1H, dd, J=8.7 and 2.5 Hz), 7.23(1H, d, J=2.6 Hz), 7.30–7.42(7H, m), 7.61(1H, d, J=8.5 Hz), 7.70(1H, dd, J=8.5 and 1.6 Hz), 7.85(2H, d, J=8.3 Hz), 8.02(1H, s), 12.35(1H, brs). IR(Nujol): 1710 cm$^{-1}$. mp: 235.5–236.5° C.

EXAMPLE 27

Synthesis of 6-((5-Bromothiophen-2-yl) sulfonylcarbamoyl)-1-(2,4-dichlorobenzyl)-2-methylbenzimidazole (39)

In the same manner as in Example 1, the desired benzimidazole (39) was obtained using the carboxylic acid as obtained in Production Example 14 and (5-bromothiophen-2-yl)sulfonamide.
[Physicochemical Properties of Compound (39)]
$^1$H-NMR (DMSO-d6, δ ppm): 2.56(3H, s), 5.64(2H, s), 6.56(1H, d, J=8.0 Hz), 7.28(1H, d, J=4.0 Hz), 7.32(1H, dd, J=8.4 and 2.1 Hz), 7.54(1H, d, J=1.6 Hz), 7.69(1H, d, J=8.5 Hz), 7.75(1H, d, J=2.2 Hz), 7.86(1H, d, J=7.7 Hz), 8.08(1H, s). IR(Nujol): 1699, 1683 cm$^{-1}$. mp: 302–303° C.

EXAMPLE 28

Synthesis of 6-((5-Bromothiophen-2-yl) sulfonylcarbamoyl)-1-(2-chloro-4-phenylbenzyl)-2-methylbenzimidazole (40)

In the same manner as in Example 1, the desired benzimidazole (40) was obtained using the carboxylic acid as obtained in Production Example 18 and (5-bromothiophen-2-yl)sulfonamide.
[Physicochemical Properties of Compound (40)]
$^1$H-NMR (DMSO-d6, δ ppm): 2.61(3H, s), 5.71(2H, s), 6.63(1H, d, J=8.0 Hz), 7.26(1H, d, J=4.0 Hz), 7.38(1H, t, J=7.3 Hz), 7.45(2H, t, J=7.6 Hz), 7.51–7.54(2H, m), 7.66 (2H, d, J=7.5 Hz), 7.71(1H, d, J=8.6 Hz), 7.86(1H, d, J=1.7 Hz), 7.89(1H, d, J=8.7 Hz), 8.14(1H, s). IR(Nujol): 1700, 1684 cm$^{-1}$. mp: 280–281° C.

PRODUCTION EXAMPLE 21
<First, Second and Third Steps>

Production of 6-Carboxy-1-(2-chloro-4-(cyclohexylmethyloxy) benzyl)-2-methylbenzimidazole Following the methods of Production Example 1, Production Example 3, and Production Example 5, the desired compound (0.52 g) was obtained from ethyl 4-(acetylamino)-3-aminobenzoate (0.333 g), 2-chloro-4-(cyclohexylmethyloxy)benzyl chloride (0.49 g), potassium carbonate (0.25 g), and sodium iodide (0.15 g) via ethyl 4-(acetylamino)-3-((2-chloro-4-(cyclohexylmethyloxy) benzyl)amino)-benzoate and 1-(2-chloro-4-(cyclohexylmethyloxy)benzyl)-6-(ethoxycarbonyl)-2-methylbenzimidazole.

[Physicochemical Property of the compound]

$^1$H-NMR (DMSO-d6, δ ppm): 1.00(2H, m), 1.21(3H, m), 1.61–1.83(6H, m), 2.52(3H, s), 3.75(2H, d, J=6.4 Hz), 5.51(2H, s), 6.55(1H, d, J=8.7 Hz), 6.81(1H, dd, J=2.4 and 8.6 Hz), 7.10(1H, d, J=2.4 Hz), 7.61(1H, d, J=8.4 Hz), 7.78(1H, dd, J=1.4 and 8.4 Hz), 7.94(1H, s), 12.70(1H, brs).

EXAMPLE 29

Synthesis of 1-(2-Chloro-4-(cyclohexylmethyloxy) benzyl)-2-methyl-6-(1-pentanesulfonylcarbamoyl) benzimidazole (41)

In the same manner as in Example 1, the desired benzimidazole (41) was obtained using the carboxylic acid as obtained in Production Example 21 and 1-pentanesulfonamide.

[Physiochanical Properties of Compound (41)]

$^1$H-NMR (DMSO-d6, δ ppm): 0.81(3H, t, J=7.3 Hz), 0.95–1.03(2H, m), 1.11–1.39(5H, m), 1.60–1.78(8H, m), 2.49(3H, s), 3.49(2H, t, J=7.7 Hz), 3.75(2H, d, J=6.4 Hz), 5.50(2H, s), 6.44(1H, d, J=8.7 Hz), 6.80(1H, dd, J=8.7 and 2.6 Hz), 7.12(1H, d, J=2.6 Hz), 7.66(1H, d, J=8.5 Hz), 7.78(1H, dd, J=8.5 and 1.7 Hz), 8.09(1H, d, J=1.3 Hz), 11.86(1H, brs). IR(Nujol): 1700, 1666 cm$^{-1}$. mp: 184–185° C.

EXAMPLE 30

Synthesis of 1-(2-Chloro-4-cyclohexylmethyloxy) benzyl)-2-methyl-6-((4-methylbenzene) sulfonylcarbamoyl) benzimidazole (42)

In the same manner as in Example 1, the desired benzimidazole (42) was obtained using the carboxylic acid as obtained in Production Example 21 and (4-methylbenzene)sulfonamide.

[Physicochemical Properties of Compound (42)]

$^1$H-NMR (DMSO-d6, δ ppm): 0.95–1.04(2H, m), 1.09–1.26(3H, m), 1.60–1.79(6H, m), 2.37(3H, s), 2.47(3H, s), 3.75(2H, d, J=6.4 Hz), 5.49(2H, s), 6.41(1H, d, J=8.6 Hz), 6.79(1H, dd, J=8.6 and 2.5 Hz), 7.11(1H, d, J=2.6 Hz), 7.41(2H, d, J=8.2 Hz), 7.62(1H, d, J=8.5 Hz), 7.70 (1H, d, J=8.0 Hz), 7.86(2H, d, J=8.2 Hz), 8.04(1H, s), 12.30(1H, brs). IR(Nujol): 1698 cm$^{-1}$. mp: 228–230° C.

EXAMPLE 31

Synthesis of 6-((5-Chlorothiophen-2-yl) sulfonylcarbamoyl)-1-(2,4-dichlorobenzyl)-2-methylbenzimidazole (43)

In the same manner as in Example 1, the desired benzimidazole (43) was obtained using the carboxylic acid as obtained in Production Example 14 and (5-chlorothiophen-2-yl)sulfonamide.

[Physicochemical Properties of Compound (43)]

$^1$H-NMR (DMSO-d6, δ ppm): 2.57(3H, s), 5.65 (2H, s), 6.59(1H, d, J=8.4 Hz), 7.19(1H, d, J=4.1 Hz), 7.32(1H, dd, J=8.4 and 2.1 Hz), 7.60(1H, d, J=3.6 Hz), 7.70(1H, d, J=8.5 Hz), 7.76(1H, d, J=2.1 Hz), 7.88(1H, d, J=8.7 Hz), 8.10(1H, s). IR(Nujol): 1700, 1684 cm$^{-1}$. mp: 301–302° C.

EXAMPLE 32

Synthesis of 1-(4-Bromo-orobenzyl)-6-((5-bromothiophen-2-yl)sulfonylcarbamoyl)-2-methylbenzimidazole (44)

In the same manner as in Example 1, the desired benzimidazole (44) was obtained using the carboxylic acid as obtained in Production Example 19 and (5-bromothiophen-2-yl)sulfonamide.

[Physicochemical Properties of Compound (44)]

$^1$H-NMR (DMSO-d6, δ ppm): 2.55(3H, s), 5.62(2H, s), 6.49(1H, d, J=8.3 Hz), 7.29(1H, d, J=4.0 Hz), 7.44(1H, dd, J=8.4 and 1.9 Hz), 7.55(1H, d, J=3.9 Hz), 7.69(1H, d, J=8.5 Hz), 7.85–7.88(2H, m),8.09(1H, s). IR(Nujol): 1700, 1684 cm$^{-1}$. mp: 310.5–311.5° C.

EXAMPLE 33

Synthesis of 1-(2,4-Dichlorobenzyl)-2-methyl-6-((4-vinyl-benzene)sulfonylcarbamoyl) benzimidazole (45)

In the same manner as in Example 1, the desired benzimidazole (45) was obtained using the carboxylic acid as obtained in Production Example 14 and (4-vinylbenzene) sulfonamide.

[Physicochemical Properties of Compound (45)]

$^1$H-NMR (DMSO-d6, δ ppm): 2.47(3H, s), 5.45(1H, d, J=11.0 Hz), 5.57(2H, s), 6.01(1H, d, J=17.7 Hz), 6.41(1H, d, J=8.4 Hz), 6.81(1H, dd, J=17.7 and 11.0 Hz), 7.30(1H, dd, J=8.4 and 2.0 Hz), 7.64(1H, d, J=8.5 Hz), 7.67–7.74(4H, m), 7.93(2H, d, J=8.4 Hz), 8.05(1H, s). IR(Nujol): 1683 cm$^{-1}$. mp: 213–214° C.

EXAMPLE 34

Synthesis of 1-(2-Chloro-4-bromobenzyl)-2-methyl-6-((4-vinyl-benzene)sulfonylcarbamoyl) benzimidazole (46)

In the same manner as in Example 1, the desired benzimidazole (46) was obtained using the carboxylic acid as obtained in Production Example 19 and (4-vinylbenzene) sulfonamide.

[Physicochemical Properties of Compound (46)] $^1$H-NMR (DMSO-d6, δ ppm): 2.46(3H, s), 5.45(1H, d, J=11.0 Hz), 5.55(2H, s), 6.01(1H, d, J=17.6 Hz), 633(1H, d, J=8.4 Hz), 6.81(1H, dd, J=17.6 and 11.0 Hz), 7.43(1H, dd, J=8.4 and 2.0 Hz), 7.64(1H, d, J=8.5 Hz), 7.67–7.73(3H, m), 7.85 (1H, d, J=2.0 Hz), 7.93(1H, d, J=8.4 Hz), 8.05(1H, d, J=1.3 Hz). IR(Nujol): 1683 cm$^{-1}$. mp: 241–243° C.

EXAMPLE 35

Synthesis of 1-(2-Chloro-4-phenylbenzyl)-2-methyl-6-((4-vinyl-benzene)sulfonylcarbamoyl) benzimidazole (47)

In the same manner as in Example 1, the desired benzimidazole (47) was obtained using the carboxylic acid as obtained in Production Example 18 and (4-vinylbenzene) sulfonamide.

[Physicochemical Properties of Compound (47)]

$^1$H-NMR (DMSO-d6, δ ppm): 2.51(3H, s), 5.42(1H, d, J=11.0 Hz), 5.62(2H, s), 5.97(1H, d, J=17.7 Hz), 6.46(1H, d, J=8.1 Hz), 6.78(1H, dd, J=17.6 and 10.9 Hz), 7.37(1H, t, J=7.1 Hz), 7.44(2H, t, J=7.5 Hz), 7.51(1H, d, J=8.2 Hz), 7.59–7.69(5H, m), 7.74(1H, d, J=8.5 Hz), 7.84(1H, s), 7.91(2H, d, J=8.3 Hz), 8.07(1H, s). IR(Nujol): 1694 cm$^{-1}$. mp: 174–175° C.

EXAMPLE 36

Synthesis of 1-(2,4-Dichlorobenzyl)-2-methyl-6-((4-methyl-benzene)sulfonylcarbamoyl)benzimidazole (48)

In the same manner as in Example 1, the desired benzimidazole (48) was obtained using the carboxylic acid as obtained in Production Example 14 and (4-methylbenzene)sulfonamide.

[Physicochemical Properties of Compound (48)]

$^1$H-NMR (DMSO-d6, δ ppm): 2.37(3H, s), 2.46(3H, s), 5.56(2H, s), 6.40(1H, d, J=8.5 Hz), 7.30(1H, dd, J=8.4 and 2.1 Hz), 7.40(2H, d, J=8.3 Hz), 7.63(1H, d, J=8.5 Hz), 7.71(1H, dd, J=8.5 and 1.5 Hz), 7.74(1H, d, J=2.2 Hz), 7.85(2H, d, J=8.3 Hz), 8.04(1H, d, J=1.2 Hz), 12.35(1H, brs). IR(Nujol): 1684 cm$^{-1}$. mp: 248–250° C.

EXAMPLE 37

Synthesis of (+)-1-(1-(2,4-Dichlorophenyl)ethyl)-2-methyl-6-(1-pentanesulfonylcarbamoyl)benzimidazole (49)

(R)-3-((1-(2,4-dichlorophenyl)ethyl)amino)-4-nitrobenzoic acid was obtained from (R)-1-(2-dichlorphenyl)ethyl)amine (optical purity: 93% ee) prepared according to the method described in Japanese Patent Laid-open No. Hei 8-325213 and 3-fluoro-4-nitrobenzoic acid. After esterifying this compound in ethanol under the acidic conditions with sulfuric acid, the resulting product was reduced with reduced iron and acetylated with acetyl chloride in pyridine. The acetylated product was cyclized by HCl in ethanol and then hydrolyzed to yield the corresponding carboxylic acid.

In the same manner as in Example 1, the desired benzimidazole (49) was obtained using the thus-obtained carboxylic acid and 1-pentanesulfonamide.

[Physicochemical Properties of Compound (49)]

$^1$H-NMR (DMSO-d6, δ ppm): 0.81(3H, t), 1.26(2H, m), 1.36(2H, m), 1.67(2H, m), 1.95(3H, d, J=7.0 Hz), 2.56(3H, s), 3.48(2H, t), 6.01(1H, q, J=7.0 Hz), 7.57–7.61(2H, m), 7.63(1H, d, J=2.2 Hz), 7.70(1H, d, J=8.5 Hz), 7.75(1H, s), 7.87(1H, d, J=8.5 Hz), 11.93(1H, brs). IR(Nujol): 1683 cm$^{-1}$. mp: 248.5–251° C. [□]D$^{25}$: +12.7 (c 0.31, MeOH). Optical purity: 90% ee (analyzed by liquid chromatography using Chiralpak AS).

EXAMPLE 38

Synthesis of (−)-1-(1-(2,4-Dichlorophenyl)ethyl)-2-methyl-6-(1-pentanesulfonylcarbamoyl)benzimidazole (50)

(S)-3-((1-(2,4-dichlorophenyl)ethyl)amino)nitrobenzoic acid was obtained from (S)-1-(2,4-dichlorophenyl)ethyl)amine (optical purity: 96% ee) prepared according to the method described in Japanese Patent Laid-open No. Hei 8-325213 and 3-fluoro-4-nitrobenzoic acid. After esterifying this compound in ethanol under the acidic conditions with sulfuric acid, the resulting product was reduced with reduced iron and acetylated with acetyl chloride in pyridine. The acetylated product was cyclized by HCl in ethanol and then hydrolyzed to yield the corresponding carboxylic acid.

In the same manner as in Example 1, the desired benzimidazole (50) was obtained using the thus-obtained carboxylic acid and 1-pentanesulfonamide.

[Physicochemical Properties of Compound (50)]

$^1$H-NMR (DMSO-d6, δ ppm): 0.81(3H, t), 1.26(2H, m), 1.36(2H, m), 1.67(2H, m), 1.95(3H, d, J=7.0 Hz), 2.56(3H, s), 3.48(2H, t), 6.01(1H, q, J=7.0 Hz), 7.57–7.61(2H, m), 7.63(1H, d, J=2.2 Hz), 7.70(1H, d, J=8.5 Hz), 7.75(1H, s), 7.87(1H, d, J=8.5 Hz), 11.93(1H, brs). IR(Nujol): 1683 cm$^{-1}$. mp: 243–246° C. [□]D$^{25}$: −7.99(c 0.31, MeOH).

EXAMPLE 39

Synthesis of 1-(4-Bromo-2-chlorobenzyl)-2-methyl-6-((1-penta-4-en)sulfonylcarbamoyl)benzimidazole (51)

In the same manner as in Example 1, the desired benzimidazole (51) was obtained using the carboxylic acid as obtained in Production Example 19 and (1-penta-4-en)sulfonamide.

[Physicochemical Properties of Compound (51)]

$^1$H-NMR (DMSO-d6, δ ppm): 1.75–1.81(2H, m), 2.12–2.18(2H, m), 2.50(3H, s), 3.50(2H, t, J=7.7 Hz), 4.97(1H, d, J=10.0 Hz), 5.10(1H, dd, J=1.7 and 18.2 Hz), 5.56(2H, s), 5.70–5.79(1H, m), 6.36(1H, d, J=8.4 Hz), 7.44(1H, dd, J=8.4 and 1.9 Hz), 7.68(1H, d, J=8.4 Hz), 7.89(1H, dd, J=8.4 and 1.5 Hz), 7.86(1H, d, J=2.0 Hz), 8.10(1H, d, J=1.4 Hz), 11.95(1H, brs). IR(Nujol): 1687 cm$^{-1}$. mp: 196–198.5° C.

EXAMPLE 40

Synthesis of 1-(2-Chloro-4-phenylbenzyl)-2-methyl-6-((1-penta-4-en)sulfonylcarbamoyl)benzimidazole (52)

In the same manner as in Example 1, the desired benzimidazole (52) was obtained using the carboxylic acid as obtained in Production Example 18 and (1-penta-4-en)sulfonamide.

[Physicochemical Properties of Compound (52)]

$^1$H-NMR(DMSO-d6, δ ppm): 1.75–1.81(2H, m), 2.11–2.17(2H, m), 2.54(3H, s), 3.50(2H, t, J=7.7 Hz), 4.96(1H, d, J=10.3 Hz), 5.00(1H, dd, J=17.2 and 1.6 Hz), 5.65(2H, s), 5.70–5.78(1H, m), 6.50(1H, d, J=8.1 Hz), 7.39(1H, t, J=7.3 Hz), 7.46(2H, t, J=7.4 Hz), 7.54(1H, dd, J=8.1 and 1.8 Hz), 7.66(2H, d, J=7.7 Hz), 7.70(1H, d, J=8.5 Hz), 7.82(1H, dd, J=8.5 and 1.6 Hz), 7.86(1H, d, J=1.7 Hz), 8.16(1H, s ), 11.98(1H, brs). IR(Nujol): 1682 cm$^{-1}$. mp: 180–185° C.

PRODUCTION EXAMPLE 22

<First, Second, and Third Steps>

Production of 6-Carboxy-1-(2-chloro-4-nitrobenzyl)-2-methyl-benzimidazole

Following the methods of Production Example 1, Production Example 3, and successively Production Example 5, the desired compound (0.37 g) was obtained from ethyl 4-(acetylamino)-3-aminobenzoate (1.11 g), 2-chloro-4-nitrobenzyl chloride (1.29 g), potassium carbonate (1.38 g), and sodium iodide (0.30 g) via ethyl 4-(acetylamino)-3-((2-chloro-4-nitrobenzyl)amino)benzoate and 1-(2-chloro-4-nitro-benzyl)-6-(ethoxycarbonyl)-2-methylbenziridazole. This product was immediately subjected to the next step.

EXAMPLE 41

Synthesis of 1-(2-Chloro-4-nitrobenzyl)-2-methyl-6-(1-pentane-sulfonylcarbamoyl)benzimidazole (53)

In the same manner as in Example 1, the desired benzimidazole (53) was obtained using the carboxylic acid as obtained in Production Example 22 and 1-pentanesulfonamide.

[Physicochemical Property of Compound (53)]
$^1$H-NMR (DMSO-d6, δ ppm): 0.80(3H, t, J=7.3 Hz), 1.21–1.37(4H, m), 1.62–1.68(2H, m), 2.49(3H, s), 3.40–3.47(2H, m), 5.72(2H, s), 6.62(1H, d, J=8.7 Hz), 7.68(1H, d, J=8.5 Hz), 7.81(1H, d, J=8.7 Hz), 8.06–8.10(2H, m), 8.42(1H, d, J=2.3 Hz), 11.88(1H, brs).

PRODUCTION EXAMPLE 23

<First and Second Steps>

Production of 1-(2-Chloro-4-iodobenzyl)-6-(ethoxycarbonyl)-2-methylbenzimidazole Following the methods of Production Example 1 and Production Example 3 successively, the desired compound (2.75 g) was obtained from ethyl 4-(acetylamino)-3-aminobenzoate (2.44 g), 2-chloro-4-iodobenzyl bromide (4.53 g), and potassium carbonate (3.73 g) via ethyl 4-(acetylamino)-3-((2-chloro-4-iodobenzyl)amino) benzoate.

[Physicochemical Property of the Compound]
$^1$H-NMR (CDCl$_3$, δ ppm): 1.39(3H, t, J=7.2 Hz), 2.56 (3H, s), 4.38(2H, q, J=7.2 Hz), 5.38(2H, s), 6.11(1H, d, J=8.2 Hz), 7.42(1H, dd, J=8.2 and 1.5 Hz), 7.75(1H, d, J=8.5 Hz), 7.75(1H, d, J=8.5 Hz), 7.82(1H, d, J=1.6 Hz), 7.96(1H, dd, J=8.4 and 1.4 Hz).

<Third Step>

Production of 1-(2-Chloro-4-(phenylethynyl) benzyl)-6-(ethoxy-carbonyl)-2-methylbenzimidazole A mixture of 1-(2-chloro-4-iodobenzyl)-6-(ethoxycarbonyl)-2-methylbenzimidazole (0.91 g), phenylacetylene (1.02 g), palladium acetate (II) (0.045 g), triphenylphosphine (0.105 g), tri n-butylamin (1.12 g), copper iodide (I) (0.038 g), and N,N-dimethylformamide (5 ml) was stirred for 1 hour at 70° C. and for 30 minutes at 100° C. After cooling the reaction solution, acetone was added thereto and the solution was filtrated with celite. The filtrate was concentrated and the resulting residue was dissolved in ethyl acetate followed by washing with 1N hydrochloric acid and a 10% aqueous solution of sodium hydroxide. The organic layer was dried and concentrated to obtain crude 1-(2-chloro-4-(phenylethynyl) benzyl)-6-(ethoxycarbonyl)-2-methylbenzimidazole. This product was immediately subjected to the next step.

[Physicochemical Property of the Compound]
$^1$H-NMR (CDCl$_3$, δ ppm): 1.40(3H, t, J=7.2 Hz), 2.61 (3H, s), 4.38(2H, q, J=7.1 Hz), 5.46(2H, s), 6.39(1H, d, J=8.1 Hz), 7.25(1H, d, J=8.3 Hz), 7.32–7.36(3H, m), 7.48–7.52(2H, m), 7.64(1H, d, J=1.4 Hz), 7.81(1H, d, J=8.5 Hz), 7.95(1H, s), 8.00(1H, d, J=8.5 Hz).

<Fourth Step>

Production of 6-Carboxy-1-(2-chloro-4-(phenylethynyl)benzyl)-2-methylbenzimidazole In the same manner as in Production Example 5, the desired compound (0.100 g) was obtained from 1-(2-chloro-4-(phenylethynyl) benzyl)-6-(ethoxycabonyl)-2-methylbenzimidazole as obtained in the above step.

[Physicochemical Property of the Compound]
$^1$H-NMR (DMSO-d6, δ ppm): 2.52(3H, s), 5.66(2H, s), 6.55(1H, d, J=8.1 Hz), 7.38–7.44(4H, m), 7.52–7.57(2H, m), 7.64(1H, d, J=8.4 Hz), 7.76(1H, d, J=1.5 Hz), 7.80(1H, d, J=8.4 Hz), 7.99(1H, s), 12.72(1H, brs).

EXAMPLE 42

Synthesis of 1-(2-Chloro-4-(phenylethynyl)benzyl)-2-methyl-6-(1-pentanesulfonylcarbamoyl) benzimidazole (54)

In the same manner as in Example 1, the desired benzimidazole (54) was obtained using the carboxylic acid as obtained in Production Example 23 and 1-pentanesulfonamide.

[Physicochemical Properties of Compound (54)]
$^1$H-NMR(DMSO-d6, δ ppm): 0.80(3H, t, J=7.3 Hz), 1.21–1.38(4H, m), 1.63–1.71(2H, m), 2.49(3H, s), 3.49(2H, t, J=7.7 Hz), 5.63(2H, s), 6.47(1H, d, J=8.0 Hz), 7.40(4H, m), 7.52–7.57(2H, m), 7.69(1H, d, J=8.4 Hz), 7.77–7.82(2H, m), 8.12(1H, s), 11.90(1H, brs). mp: 224–225° C.

PRODUCTION EXAMPLE 24

<First Step>

Production of 1-(2-Chloro-4-(2-phenylethenyl) benzyl)-6-(ethoxy-carbonyl)-2-methylbenzimidazole A mixture of 1-(2-chloro-4-iodobenzyl)-6-(ethoxycarbonyl)-2-methylbenzimidazole (0.91 g) as obtained in Production Example 23, phenylacetylene (1.04 g), palladium acetate (II) (0.068 g), triphenylphosphine (0.16 g), tri n-butylamine (1.12 g), and N,N-dimethylformamide (10 ml) was stirred overnight at 60° C. After cooling, the reaction mixture was extracted with ethyl acetate and water. The organic layer was dried and concentrated. The residue thus obtained was dissolved in acetone and decolorized with activated charcoal. Solid was removed by filtration and the filtrate was concentrated to obtain crude 1-(2-chloro-4-(2-phenyl-ethenyl)benzyl)-6-(ethoxycarbonyl)-2-methylbenzimidazole (0.68 g).

[Physicochemical Property of the Compound]
$^1$H-NMR (CDCl$_3$, δ ppm): 1.39(3H, t, J=7.1 Hz), 2.59 (3H, s), 4.37(2H, q, J=7.1 Hz), 5.46(2H, s), 6.40(1H, d, J=8.0 Hz), 6.98(1H, d, J=16.2 Hz), 7.08(1H, d, J=16.2 Hz), 7.20(1H, d, J=8.0 Hz), 7.28(1H, t, J=7.4 Hz), 7.36(2H, t, J=7.5 Hz), 7.48(2H, d, J=7.8 Hz), 7.61(1H, s), 7.56(1H, d, J=8.5 Hz), 7.96(1H, s), 8.00(1H, d, J=8.4 Hz).

<Second Step>

Production of 6-Carboxy-1-(2-chloro-4-(2-phenylethenyl)benzyl)-2-methylbenzimidazole In the same manner as in Production Example 5, the desired compound (0.49 g) was obtained from 1-(2-chloro-4-(2-phenylethenyl)benzyl)-6-(ethoxycarbonyl)-2-methylbenzimidazole (0.68 g).

[Physicochemical Property of the Compound]
$^1$H-NMR (DMSO-d5, δ ppm): 2.54(3H, s), 5.62(2H, s), 6.58(1H, d, J=8.1 Hz), 7.21(1H, d, J=16.5 Hz), 7.27(1H, t, J=7.5 Hz), 7.31(1H, d, J=16.4 Hz), 7.36(2H, t, J=7.5 Hz), 7.44(1H, d, J=8.1 Hz), 7.57(2H, d, J=7.7 Hz), 7.64(1H, d, J=8.4 Hz), 7.80(2H, dd, J=8.4 and 1.5 Hz), 7.97(1H, s), 12.69(1H, brs).

EXAMPLE 43

Synthesis of 1-(2-Chloro-4-((E)-2-phenylethenyl) benzyl)-2-methyl-6-(I-pentanesulfonylcarbamoyl) benzimidazole (55)

In the same manner as in Example 1, the desired benzimidazole (55) was obtained using the carboxylic acid as obtained in Production Example 24 and 1-pentanesulfonamide.

[Physicochemical Properties of Compound (55)]
$^1$H-NMR (DMSO-d6, δ ppm): 0.79(3H, t, J=7.3 Hz), 1.21–1.37(4H, m), 1.63–1.70(2H, m), 2.51(3H, s), 3.48(2H, t, J=7.7 Hz), 5.60(2H, s), 6.48(1H, d, J=8.2 Hz), 7.21(1H, d, J=16.5 Hz), 7.27(1H, t, J=7.3 Hz), 7.31(1H, d, J=16.5 Hz), 7.36(2H, t, J=7.5 Hz), 7.44(1H, d, J=8.1 Hz), 7.57(2H, d, J=8.0 Hz), 7.68(1H, d, J=8.5 Hz), 7.80(1H, d, J=8.5 Hz), 7.83(1H, s), 8.12(1H, s), 11.90(11H, brs). mp: 242–243° C.

EXAMPLE 44

Synthesis of 1-(2-Chloro-4-((E)-2-phenylethenyl) benzyl)-2-methyl-6-((4-methylbenzene) sulfonylcarbamoyl)benzimidazole (56)

In the same manner as in Example 1, the desired benzimidazole (56) was obtained using the carboxylic acid as obtained in Production Example 24 and (4-methylbenzene) sulfonamide.
[Physicochemical Properties of Compound (56)]
$^1$H-NMR (DMSO-d6, δ ppm): 2.35(3H, s), 2.49(3H, s), 5.58(2H, s), 6.46(1H, d, J=8.1 Hz), 7.21(1H, t, J=16.5 Hz), 7.28(1H, t, J=7.4 Hz), 7.31(1H, d, J=16.6 Hz), 7.34–7.44 (6H, m), 7.58(2H, d, J=7.6 Hz), 7.64(1H, d, J=8.5 Hz), 7.71(1H, d, J=8.6 Hz), 7.82(1H, s), 7.85(1H, d, J=8.3 Hz), 8.06(1H, s), 12.30(1H, brs). mp: 250–252° C.

PRODUCTION EXAMPLE 25
<First and Second Steps>

Production of 6-Carboxy-1-(2-chloro-4-(1-hexen-1-yl)benzyl)-2-methylbenzimidazole A mixture of 1-(2-chloro-4-iodobenzyl)-6-(ethoxycarbonyl)-2-methylbenzimidazole (1.21 g), 1-hexene (1.12 g), palladium acetate (II) (0.09 g), triphenylphosphine (0.21 g), tri-n-butylamine (1.49 g), and N,N-dimethylformamide (15 ml) was stirred overnight at 60° C. The reaction mixture was concentrated under reduced pressure and the resulting residue was purified by silica gel column chromatography (eluate: hexane/ethyl acetate=1/2) to obtain 1-(2-chloro-4-(1-hexen-1-yl)benzyl)-6-(ethoxycarbonyl)-2-methyl-benzimidazole (0.99 g). In accordance with the method of Production Example 5, this product was immediately converted to the desired compound (0.64 g) containing about 10% of 6-carboxy-1-(2-chloro-4-(1-hexen-2-yl)benzyl)-2-methyl-benzimidazole. This compound was immediately subjected to the next step.

EXAMPLE 45

Synthesis of 1-(2-Chloro-4-(1-hexen-1-yl)benzyl)-2-methyl-6-(1-pentanesulfonylcarbamoyl) benzimidazole (57)

In the same manner as in Example 1, the desired benzimidazole (57) was obtained using the carboxylic acid as obtained in Production Example 25 and 1-pentanesulfonamide.
[Physicochemical Properties of Compound (57)]
$^1$H-NMR (DMSO-d6, δ ppm): 0.70–0.90(6H, m), 1.21–1.71(10H, m), 1.91–2.17(2H, m), 2.49(3H, s), 3.48 (2H, t, J=7.7 Hz), 5.10–5.85(3H, m), 6.33–6.41(2H, m), 7.03–7.40(1H, m), 7.53–7.59(1H, m), 7.67(1H, d, J=8.5 Hz), 7.79(1H, d, J=8.5 Hz), 8.10(1H, s), 11.87(1H, brs). mp: 175–177° C.

EXAMPLE 46

Synthesis of 1-(2-Chloro-4-(1-hexen-1-yl)benzyl)-2-methyl-6-((4-methylbenzene)sulfonylcarbamoyl) benzimidazole (58)

In the same manner as in Example 1, the desired benzimidazole (58) was obtained using the carboxylic acid as obtained in Production Example 25 and (4-methylbenzene) sulfonamide.
[Physicochemical Properties of Compound (58)]
$^1$H-NMR (DMSO-d6, δ ppm): 0.81–0.91(3H, m), 1.23–1.60(4H, m), 1.90–2.17(2H, m), 2.36(3H, s), 2.488 and 2.491(3H, 2s), 5.08–5.86(3H, m), 6.31–6.42(2H, m), 7.02–7.38(1H, m), 7.39(2H, d, J=8.1 Hz), 7.52–7.60(1H, m), 7.62(1H, d, J=8.4 Hz), 7.71(1H, d, J=8.6 Hz), 7.85(2H, d, J=8.1 Hz), 8.02–8.07(1H, m), 12.31(1H, brs). mp: 190–192° C.

EXAMPLE 47

Synthesis of 1-(2-Chloro-4-(2-phenylethyl)benzyl)-2-methyl-6-(1-pentanesulfonylcarbamoyl) benzimidazole (59)

Platinum oxide (0.010 mg) was added to an acetic acid solution (10 ml) of Compound (55) (0.24 g) as obtained in Example 43 and the mixture was stirred under a hydrogen atmosphere (1 atmospheric pressure) at room temperature for 1.5 hour. After insoluble materials were filtered off, the filtrate was concentrated under reduced pressure. The residue was recrystalized fom a mixture of 2-propanol and water to obtain the desired benzimidazole (59) (0.22 g).
[Physicochemical Properties of Compound (59)]
$^1$H-NMR (DMSO-d6, δ ppm): 0.80(3H, t, J=7.1 Hz), 1.21–1.40(4H, m), 1.64–1.72(2H, m), 2.48(3H, s), 2.84(4H, s), 3.48(2H, t, J=7.6 Hz), 5.55(2H, s), 6.39(1H, d, J=7.9 Hz), 7.09(1H, d J=8.0 Hz), 7.15(1H, t, J=7.5 Hz), 7.27(3H, m), 7.19(2H, d, J=7.5 Hz), 7.24(2H, t, J=7.5 Hz), 7.43(1H, s), 7.67(1H, d, J=8.3 Hz), 7.79(1H, d, J=8.5 Hz), 8.09(1H, s), 11.85(1H, brs). mp: 187–189° C.

PRODUCTION EXAMPLE 26
<First Step>

Production of 1-(4-t-Butylthio-2-chlorobenzyl)-6-(ethoxy-carbonyl)-2-methylbenzimidazole A mixture of 1-(2-chloro-4-iodobenzyl)-6-(ethoxycarbonyl)-2-methylbenzimidazole (0.702 g) as obtained in Production Example 23, tetrakis (triphenylphosphine)palladium (O) (0.357 g), tri-n-butylamine (0.573 g), t-butylmercaptan (0.397 g), and N,N-dimethylformamide (3 ml) was stirred overnight at 60° C. The reaction mixture was concentrated under reduced pressure and the resulting residue was purified by silica gel column chromatography (eluate: hexane/ethyl acetate=1/1) to obtain 1-(4-t-butylthio-2-chlorobenzyl)-6-(ethoxycarbonyl)-2-methylbenzimidazole (0.500 g).
[Physicochemical Property of the Compound]
$^1$H-NMR (CDCl$_3$, δ ppm): 1.28(9H, s), 1.39(3H, m), 2.56(3H, s), 4.37(2H, m), 5.43(2H, s), 6.36(1H, d, J=8.0 Hz), 7.25(1H, dd, J=1.5 and 8.0 Hz), 7.65(1H, d, J=1.5 Hz), 7.75(1H, d, J=8.4 Hz), 7.94(1H, s), 8.00(1H, dd, J=1.4 and 8.4 Hz).
<Second Step>

Production of 6-Carboxy-1-(4-t-butylthio-2-chlorobenzyl)-2-methyl benzimidazole

In the same manner as in Production Example 5, the desired compound (0.365 g) was obtained from 1-(4-t-butylthio-2-chlorobenzyl)-6-(ethoxycarbonyl)-2-methylbenzimidazole (0.500 g).
[Physicochemical Property of the Compound]
$^1$H-NMR (DMSO-d6, δ ppm): 1.21(9H, s), 2.51(3H, s), 5.65(2H, s), 6.56(1H, d, J=8.0 Hz), 7.36(1H, dd, J=1.6 and 8.0 Hz), 7.62(1H, d, J=1.6 Hz), 7.63(1H, d, J=8.4 Hz), 7.79(1H, d, J=8.4 Hz), 7.97(1H, s), 12.7(1H, brs).

EXAMPLE 48

Synthesis of 1-(4-t-Butylthio-2-chlorobenzyl)-2-methyl-6-(1-pentanesulfonylcarbamoyl) benzimidazole (60)

In the same manner as in Example 1, the desired benzimidazole (60) was obtained using the carboxylic acid as obtained in Production Example 26 and 1-pentanesulfonamide.

[Physicochemical Properties of Compound (60)]

$^1$H-NMR(DMSO-d6, δ ppm): 0.80(3H, t, J=7.2 Hz), 1.21–1.29(11H, m), 1.34(2H, m), 1.67(2H, m), 2.49(3H, s), 3.49(2H, m), 5.62(2H, s), 6.46(1H, d, J=8.0 Hz), 7.36(1H, d, J=8.0 Hz), 7.64(1H, s), 7.68(1H, d, J=8.5 Hz), 7.80(1H, d, J=8.5 Hz), 8.12(1H, s), 11.84(1H, brs). mp: 163–165° C.

EXAMPLE 49

Synthesis of 1-(4-t-Butylthio-2-chlorobenzyl)-2-methyl-6-((4-methylbenzene)sulfonylcarbamoyl) benzimidazole (61)

In the same manner as in Example 1, the desired benzimidazole (61) was obtained using the carboxylic acid as obtained in Production Example 26 and (4-methylbenzene) sulfonamide.

[Physicochemical Properties of Compound (61)]

$^1$H-NMR (DMSO-d6, δ ppm): 1.21(9H, s), 2.37(3H, s), 2.46(3H, s), 5.61(2H, s), 6.44(1H, d, J=7.9 Hz), 7.35(1H, d, J=7.9 Hz), 7.40(2H, d, J=8.1 Hz), 7.61–7.67(2H, m), 7.71 (1H, d), 7.85(2H, d, J=8.3 Hz), 8.05(1H, s), 12.3(1H, brs). mp: 208.5–210.5° C.

PRODUCTION EXAMPLE 27

<First Step>

Production of Ethyl 4-(acetylamino)-3-((2-chloro-4-(phenoxy-methyl)benzyl)amino)benzoate In the same manner as in Production Example 1, the desired compound (1.63 g) was obtained from ethyl 4-(acetylamino)-3-aminobenzoate (0.80 g), 2-chloro-4-(phenoxymethyl)benzyl chloride (0.96 g), sodium carbonate (0.47 g), and sodium iodide (0.30 g). The compound was immediately subjected to the next step.

<Second Step>

Production of 1-(2-Chloro-4-(phenoxymethyl) benzyl)-6-(ethoxy-carbonyl)-2-methylbenzimidazole In the same manner as in Production Example 3, the compound was obtained from ethyl 4-(acetylamino)-3-((2-chloro-4-(phenoxy-methyl)benzyl)amino)benzoate (1.63 g). This compound was immediately subjected to the next step.

<Third Step>

Production of 6-Carboxy-1-(2-chloro-4-(phenoxymethyl)benzyl)-2-methylbenzimidazole In the same manner as in Production Example 5, the desired compound (0.78 g) was obtained from 1-(2-chloro-4(phenoxymethyl)benzyl)-6-(ethoxycarbonyl)-2-methylbenzimidazole obtained in the above step.

[Physicochemical Property of the Compound]

$^1$H-NMR (DMSO-d6, δ ppm): 2.52(3H, s), 5.07(2H, s), 5.61(2H, s), 6.56(1H, d, J=7.8 Hz), 6.92(1H, t, J=7.1 Hz), 6.97(2H, d, J=7.5 Hz), 7.27(3H, m), 7.62(2H, s), 7.79(1H, d, J=8.0 Hz), 7.95(1H, s).

EXAMPLE 50

Synthesis of 1-(2-Chloro-4-(phenoxymethyl) benzyl)-2-methyl-6-(1-pentanesulfonylcarbamoyl) benzimidazole (62)

In the same manner as in Example 1, the desired benzimidazole (62) was obtained using the carboxylic acid as obtained in Production Example 27 and 1-pentanesulfonamide.

[Physicochemical Properties of Compound (62)]

$^1$H-NMR (DMSO-d6, δ ppm): 0.80(3H, t, J=7.2 Hz), 1.24(2H, m), 1.34(2H, m), 1.66(2H, m), 2.49(3H, s), 3.48 (2H, t, J=7.7 Hz), 5.07(2H, s), 5.59(2H, s), 6.46(1H, d, J=8.0 Hz), 6.92(1H, t, J=7.7 Hz), 6.97(2H, d, J=8.5 Hz), 7.27(3H, m), 7.64(1H, s), 7.67(1H, d, J=8.4 Hz), 7.79(1H, d, J=8.4 Hz), 8.10(1H, s), 11.86(1H, brs). mp: 169–173° C.

EXAMPLE 51

Synthesis of 1-(2-Chloro-4-(phenoxymethyl) benzyl)-2-methyl-6-((4-methylbenzene) sulfonylcarbamoyl)benzimidazole (63)

In the same manner as in Example 1, the desired benzimidazole (63) was obtained using the carboxylic acid as obtained in Production Example 27 and (4-methylbenzene) sulfonamide.

[Physicochemical Properties of Compound (63)]

$^1$H-NMR (DMSO-d6, δ ppm): 2.37(3H, s), 2.47(3H, s), 5.07(2H, s), 5.58(2H, s), 6.43(1H, d, J=7.8 Hz), 6.93(1H, t, J=7.3 Hz), 6.97(2H, d, J=7.9 Hz), 7.27(3H, m), 7.39(2H, d, J=7.7 Hz), 7.63(2H, m), 7.71(1H, d, J=8.5 Hz), 7.85(2H, d, J=7.5 Hz), 8.04(1H, s), 12.31(1H, brs). mp: 161–165° C.

PRODUCTION EXAMPLE 28

<First Step>

Production of Ethyl 4-(acetylamino)-3-((2-chloro-4-(cyclo-hexyloxymethyl)benzyi)amino)benzoate In the same manner as in Production Example 1, the desired compound (1.94 g) was obtained from ethyl 4-(acetylamino)-3-aminobenzoate (0.89 g), 2-chloro-4-(cyclohexyloxymethyl)benzyl chloride (1.09 g), sodium carbonate (0.51 g), and sodium iodide (0.30 g). This compound was immediately subjected to the next step.

<Second Step>

Production of 1-(2-Chloro-4-(cyclohexyloxymethyl) benzyl)-6-(ethoxycarbonyl)-2-methylbenzimidazole In the same manner as in Production Example 3, the desired compound was obtained from ethyl 4-(acetylamino)-3-((2-chloro-4-(cyclohexyloxymethyl)benzyl)amino) benzoate (1.94 g). This compound was immediately subjected to the next step.

<Third Step>

Production of 6-Carboxy-1-(2-chloro-4-(cyclohexyloxymethyl)-benzyl)-2-methylbenzimidazole In the same manner as in Production Example 5, the desired compound (1.13 g) was obtained from 1-(2-chloro-4-(cyclohexyloxy methyl)benzyl-6-(ethoxycarbonyl)-2-methylbenzimidazole as obtained in the above step.

[Physicochemical Properties of the Compound]

$^1$H-NMR (DMSO-d6, δ ppm): 1.17–1.24(5H, m), 1.44 (1H, m), 1.62(2H, m), 1.81(2H, m), 2.50(3H, s), 4.44(2H, s), 4.55(1H, m), 5.58(2H, s), 6.52(1H, d, J=7.7 Hz), 7.15(1H, d, J=8.0 Hz), 7.45(1H, s), 7.60(1H, d, J=8.3 Hz), 7.78(1H, d, J=8.4 Hz), 7.92(1H, s).

EXAMPLE 52

Synthesis of 1-(2-Chloro-4-(cyclohexyloxymethyl) benzyl)-2-methyl-6-(1-pentanesulfonylcarbamoyl) benzimidazole (64)

In the same manner as in Example 1, the desired benzimidazole (64) was obtained using the carboxylic acid as obtained in Production Example 28 and 1-pentanesulfonamide.

[Physicochemical Properties of Compound (64)]
¹H-NMR ()MSO-d6, δ ppm): 0.80(3H, t, J=7.2 Hz), 1.15–1.30(7H, m), 1.34(2H, m), 1.45(1H, m), 1.66(4H, m), 1.81(2H, m), 2.49(3H, s), 3.48(2H, t, J=7.7 Hz), 4.45(2H, s), 4.56(1H, d, J=4.6 Hz), 5.7(2H, s), 6.43(1H, d, J=8.0 Hz), 7.16(1H, d, J=7.5 Hz), 7.48(1H, s), 7.67(1H, d, J=8.4 Hz), 7.79(1H, d, J=8.8 Hz), 8.09(1H, s), 11.87(1H, brs). mp: 129–133° C.

EXAMPLE 53

Synthesis of 1-(2-Chloro-4-(cyclohexyloxymethyl) benzyl)-2-methyl-6-((4-methylbenzene) sulfonylcarbamoyl) benzimidazole (65)

In the same manner as in Example 1, the desired benzimidazole (65) was obtained using the carboxylic acid as obtained in Production Example 28 and (4-methylbenzene) sulfonamide.

[Physicochemical Properties of Compound (65)]
¹H-NMR (DMSO-d6, δ ppm): 1.17–1.24(5H, m), 1.46 (1H, m), 1.63(2H, m), 1.82(2H, m), 2.37(3H, s), 2.47(3H, s), 4.45(2H, s), 4.56(1H, d, J=7.1 Hz), 5.56(2H, s), 6.41(1H, d, J=7.7 Hz), 7.15(1H, d, J=8.0 Hz), 7.40(2H, d, J=7.8 Hz), 7.47(1H, s), 7.63(1H, d, J=8.5 Hz), 7.71(1H, d, J=8.4 Hz), 7.85(2H, d, J=7.7 Hz), 8.04(1 H, s), 12.29(1 H, brs). mp: 143–151° C.

EXAMPLE 54

Synthesis of 1-(2-Chloro-4-phenylbenzyl)-2-methyl-6-((n-pentyl-aminosulfonyl)carbamoyl) benzimidazole (66)

In the same manner as in Example 1, the desired benzimidazole (66) was obtained using the carboxylic acid as obtained in Production Example 18 and N-(n-pentyl)sulfamide.

[Physicochemical Properties of Compound (66)]
¹H-NMR (DMSO-d6, δ ppm): 0.73(3H, t, J=6.8 Hz), 1.09–1.21(4H, m), 1.36–1.42(2H, m), 2.53(3H, s), 2.86(2H, t, J=6.4 Hz), 5.63(2H, s), 6.51(1H, d, J=8.2 Hz), 7.38(1H, t, J=7.4 Hz), 7.45(2H, t, J=7.5 Hz), 7.53(1H, d, J=8.1 Hz), 7.62–7.70(4H, m), 7.79(1H, d, J=8.4 Hz), 7.85(1H, s), 8.12(1H, s), 11.58(1H, brs). mp: 193.5–195.2° C.

EXAMPLE 55

Synthesis of 1-(2,4-Dichlorobenzyl)-2-methyl-6-(((4-methyl-phenyl)aminosulfony)carbamoyl) benzimidazole (67)

In the same manner as in Example 1, the desired benzimidazole (67) was obtained using the carboxylic acid as obtained in Production Example 14 and N-(4-methylphenyl) sulfamide.

[Physicochemical Properties of Compound (67)]
¹H-NMR(DMSO-d6, δ ppm): 2.16(3H, s), 2.47(3H, s), 5.53(2H, s), 6.43(1H, d, J=8.4 Hz), 7.01(2H, d, J=8.4 Hz), 7.06(2H, d, J=8.4 Hz), 7.30(1H, dd, J=8.3 and 2.0 Hz), 7.16(1H, d, J=8.4 Hz), 7.69(1H, d, J=8.6 Hz), 7.75(1 H, d, J=2.0 Hz), 7.96(1H, s), 10.30(1H, brs), 11.82(1H, brs). mp: 190–191° C.

EXAMPLE 56

Synthesis of 1-(2-Chloro-4-phenylbenzy)-2-methyl-6-(((4-methyl-phenyl)aminosulfonyl)carbamoyl) benzimidazole (68)

In the same manner as in Example 1, the desired benzimidazole (68) was obtained using the carboxylic acid as obtained in Production Example 18 and N-(4-methylphenyl) sulfamide.

[Physicochemical Properties of Compound (68)]
¹H-NMR (DMSO-d6, δ ppm): 2.10(3H, s), 2.49(3H, s), 5.60(2H, s), 6.49(1H, d, J=8.0 Hz), 6.99(2H, d, J=8.4 Hz), 7.05(2H, d, J=8.4 Hz), 7.38(2H, t, J=7.4 Hz), 7.45(1H, t, J=7.4 Hz), 7.52(1H, dd, J=8.1 and 2.2 Hz), 7.65(3H, m), 7.70(1H, dd, J=8.5 and 1.4 Hz), 7.86(1H, d, J=1.8 Hz), 8.01(1H, s), 10.31(1H, brs), 11.85(1H, brs). mp: 182.5–183.5° C.

PRODUCTION EXAMPLE 29

Production of 6-Carboxy-1-(2-chloro-4-iodobenzyl)-2-methyl-benzimidazole

In the same manner as in Production Example 5, the desired compound (0.86 g) was obtained from 1-(2-chloro-4-iodobenzyl)-6-(ethoxycarbonyl)-2-methylbenzimidazole as obtained in Production Example 23.

[Physicochemical Property of the Compound]
¹H-NMR (DMSO-d6, δ ppm): 2.50(3H, s), 5.57(2H, s), 6.28(1H, d, J=8.3 Hz), 7.59(1H, dd, J=8.2 and 1.6 Hz), 7.63(1H, d, J=8.4 Hz), 7.80(1H, dd, J=8.4 and 1.5 Hz), 7.93(1H, d, J=1.6 Hz), 7.96(1H, d, J=1.3 Hz), 12.70(1H, brs).

EXAMPLE 57

Synthesis of 1-(2-Chloro iodobenzyl)-2-methyl-6-(1-pentane-sulfonylcarbamoyl)benzimidazole (69)

In the same manner as in Example 1, the desired benzimidazole (69) was obtained using the carboxylic acid as obtained in Production Example 29 and 1-pentanesulfonamide.

[Physicochemical Properties of Compound (69)]
¹H-NMR(DMSO-d6, δ ppm): 0.80(3H, t, J=7.4 Hz), 1.21–1.30(2H, m), 1.31–1.39(2H, m), 1.63–1.71(2H, m), 2.48(3H, s), 3.49(2H, t, J=7.7 Hz), 5.54(2H, s), 6.18(1H, d, J=8.2 Hz), 7.59(1H, d, J=8.3 Hz), 7.67(1H, d, J=8.4 Hz), 7.79(1H, d, J=8.4 Hz), 7.95(1H, s), 8.08(1H, s), 11.88(1H, brs). mp: 226–228.5° C.

EXAMPLE 58

Synthesis of 1-(2-Chloro-4-iodobenzyl)-2-methyl-6-((4-methyl-benzene)sulfonylcarbamoyl) benzimidazole (70)

In the same manner as in Example 1, the desired benzimidazole (70) was obtained using the carboxylic acid as obtained in Production Example 29 and (4-methylbenzene) sulfonamide.

[Physicochemical Properties of Compound (70)]
¹H-NMR(DMSO-d6, δ ppm): 2.38(3H, s), 2.46(3H, s), 5.52(2H, s), 6.15(1H, d, J=8.2 Hz), 7.40(2H, d, J=8.2 Hz), 7.57(1H, dd, J=8.2 and 1.5 Hz), 7.62(1H, d, J=8.5 Hz), 7.70(1H, dd, J=8.5 and 1.5 Hz), 7.85(2H, d, J=8.3 Hz), 7.94(1H, d, J=1.7 Hz), 8.03(1H, s), 12.34(1H, brs). mp: 226–228.5° C.

PRODUCTION EXAMPLE 30

<First Step>

Production of Ethyl 4-(acetylamino)-3-((2-chloro-4-ethoxy-benzyl)amino)benzoate

In the same manner as in Production Example 1, the desired compound (1.34 g) was obtained from ethyl 4-(acetylamino)-3-aminobenzoate (1.12 g), 2-chloro-4-ethoxybenzyl chloride (0.96 g), sodium carbonate (0.80 g), and sodium iodide (0.38 g). The compound was immediately subjected to the next step.
<Second Step>

Production of 1-(2-Chloro-4-ethoxybenzyl)-6-(ethoxycarbonyl)-2-methylbenzimidazole In the same manner as in Production Example 3, the desired compound was obtained from ethyl 4-(acetylamino)-3-((2-chloro-4-ethoxybenzyl)amino)benzoate (1.34 g). The compound was immediately subjected to the next step.
<Third Step>

Production of Carboxy-1-(2-chloro-4-ethoxybenzyl)-2-methyl benzimidazole

In the same manner as in Production Example 5, the desired compound (0.91 g) was obtained from 1-(2-chloro-4-(cyclohexyloxy methyl)benzyl)-6-(ethoxycarbonyl)-2-methylbenzimidazole as obtained in the above step.
[Physicochemical Property of the Compound]
$^1$H-NMR (DMSO-d6, δ ppm): 1.27(3H, t, J=6.9 Hz), 2.49(3H, s), 3.99(2H, q, J=6.9 Hz), 5.52(2H, s), 6.56(1H, d, J=6.4 Hz), 6.81(1H, d, J=6.8 Hz), 7.09(1H, d, J=2.0 Hz), 7.66(1H, brs), 7.78(1H, brs), 7.99(1H, brs), 12.69(1H, brs).

EXAMPLE 59

Synthesis of 1-(2-Chloro-4-ethoxybenzyl)-2-methyl-6-(1-pentane-sulfonylcarbamoyl)benzimidazole (71)

In the same manner as in Example 1, the desired benzimidazole (71) was obtained using the carboxylic acid as obtained in Production Example 30 and 1-pentanesulfonamide.
[Physicochemical Properties of Compound (71)]
$^1$H-NMR (DMSO-d6, δ ppm): 0.81(3H, t, J=7.3 Hz), 1.27(5H, m), 1.35(2H, m), 1.67(2H, m), 2.49(3H, s), 3.49 (2H, t, J=7.6 Hz), 3.99(2H, q, J=6.9 Hz), 5.51(2H, s), 6.46(1H, d, J=8.6 Hz), 6.80(1H, d, J=8.6 Hz), 7.11(1H, d, J=1.3 Hz), 7.68(1H, brs), 7.79(1H, d, J=6.4 Hz), 8.12(1H, s), 11.89(1H, brs). mp: 190–191° C.

EXAMPLE 60

Synthesis of 1-(2-Chloro-4-ethoxybenzyl)-2-methyl-6-((4-methyl-benzene)sulfonylcarbamoyl)benzimidazole (72)

In the same manner as in Example 1, the desired benzimidazole (72) was obtained using the carboxylic acid as obtained in Production Example 30 and (4-methylbenzene)sulfonamide.
[Physicochemical Properties of Compound (72)]
$^1$H-NMR (DMSO-d6, δ ppm): 1.27(3H, t, J=6.8 Hz), 2.37(3H, s), 2.46(3H, s), 3.99(2H, q, J=6.8 Hz), 5.50(2H, s), 6.42(1H, d, J=8.4 Hz), 6.79(1H, d, J=7.9 Hz), 7.10(1H, s), 7.40(2H, d, J=7.9 Hz), 7.71(2H, brs), 7.85(2H, d, J=7.9 Hz), 8.15(1H, brs). mp: 254–256° C.

PRODUCTION EXAMPLE 31
<First Step>

Production of Ethyl 4-(acetylamino)-3-((2-chloro-4-(methoxy-carbonyl)benzyl)amino)benzoate In the same manner as in Production Example 1, the desired compound (5.00 g) was obtained from ethyl 4-(acetylamino)-3-aminobenzoate (4.44 g), 2-chloro-4-(methoxycarbonyl)benzyl chloride (6.85 g), and potassium carbonate (5.5 g).

[Physicochemical Property of the Compound]
$^1$H-NMR (CDCl$_3$, δ ppm): 1.34(3H, t, J=7.0 Hz), 2.24 (3H, s), 3.91(3H, s), 4.31(2H, q, J=7.0 Hz), 4.45–4.53(3H, m), 7.36(2H, brs), 7.45(2H, t, J=7.1 Hz), 7.51(1H, d, J=8.3 Hz), 7.87(1H, d, J=8.0 Hz), 8.07(1H, s).
<Second Step>

Production of 1-(2-Chloro-4-(methoxycarbonyl) benzyl)-6-(ethoxy-carbonyl)-2-methylbenzimidazole In the same manner as in Production Example 3, the desired compound (2.40 g) was obtained from ethyl 4-(acetylamino)-3-((2-chloro-4-(methoxycarbonyl)benzyl) amino)benzoate (5.00 g).
[Physicochemical Properties of the Compound]
$^1$H-NMR (CDCl$_3$, δ ppm): 1.38(3H, t, J=7.1 Hz), 2.57 (3H, s), 3.91(3H, s), 4.37(2H, q, J=7.1 Hz), 5.48(2H, s), 6.46(1 H, d, J=8.1 Hz), 7.75(1H, dd, J=8.1 and 1.4Hz), 7.77(1H, dd, J=8.6 Hz), 7.91(1H, s), 8.01(1H, dd, J=8.4 and 1.2 Hz), 8.14(1 H, d, J=1.6 Hz).
<Third Step>

Production of 6-Carboxy-1-(2-chloro-4-carboxybenzyl)-2-methyl benzimidazole

In the same manner as in Production Example 5, the desired compound (0.36 g) was obtained from 1-(2-chloro-4-carboxybenzyl)-6-(ethoxycarbonyl)-2-methylbenzimidazole (0.60 g).
[Physicochemical Properties of the compound]
$^1$H-NMR (DMSO-d6, δ ppm): 2.51(3H, s), 5.69(2H, s), 6.59(1H, d, J=8.1 Hz), 7.65(1H, d, J=8.4 Hz), 7.76(1H, d, J=8.1 Hz), 7.80(1H, d, J=8.4 Hz), 7.98(1H, s), 7.99(1H, s), 13.02(2H, brs).

EXAMPLE 61

Synthesis of 1-(2-Chloro-4-(1-pentanesulfonylcarbamoyl)benzyl)-2-methyl-6-(1-pentanesulfonylcarbamoyl)benzimidazole (73)

In the same manner as in Example 1, the desired benzimidazole (73) was obtained using the carboxylic acid as obtained in Production Example 31 and 1-pentanesulfonamide.
[Physicochemical Properties of Compound (73)]
$^1$H-NMR (DMSO-6, δ ppm): 0.77–0.86(6H, m), 1.20–1.39(8H, m), 1.63–1.70(4H, m), 2.49(3H, s), 3.43–3.52(4H, m), 5.67(2H, s), 6.54(1H, d, J=7.9 Hz), 7.70(1H, d, J=8.4 Hz), 7.75(H, d, J=8.1 Hz), 7.81(1H, d, J=8.5 Hz), 8.10(1H, s), 8.12(1H, s), 11.95(1H, brs). mp: 254–255° C.

EXAMPLE 62

Synthesis of 1-(4-Bromo-2-chlorobenzyl)-2-methyl-6-(1-pentane-sulfonylcarbamoyl)benzimidazole (74)

In the same manner as in Example 1, the desired benzimidazole (74) was obtained using the carboxylic acid as obtained in Production Example 19 and 1-pentanesulfonamide.
[Physicochemical Properties of Compound (74)]
$^1$H-NMR (DMSO-d6, δ ppm): 0.82(3H, t, J=7.2 Hz), 1.22–1.29(2H, m), 1.31–1.39(2H, m), 1.62–1.70(2H, m), 2.50(3H, s), 3.50(2H, t, J=7.7 Hz), 5.57(2H, s), 6.37(1H, d, J=8.4 Hz), 7.45(1H, dd, J=8.4 and 2.0 Hz), 7.68(1H, d, J=8.5 Hz), 7.80(1H, dd, J=8.4 and 1.5 Hz), 7.87(1H, d, J=2.0 Hz), 8.10(1H, d, J=1.3 Hz), 11.86(1H, brs). mp : 222–223° C.

EXAMPLE 63

Synthesis of 1-(2-Chloro-4-(trifluoromethyl) benzyl)-2-methyl-6-((4-methylbenzene) sulfonylcarbamoyl)benzimidazole (75)

In the same manner as in Example 1, 1-(2-chloro-4-(trifluoromethyl)benzyl)-2-methyl-6-((4-methylbenzene)

sulfonyl-carbamoyl)benzimidazole (75) (186 mg) was obtained as white crystals from 6-carboxy-1-(2-chloro-4-(trifluoromethyl)benzyl)-2-methyl-benzimidazole (175 mg) as obtained in Production Example 13 and (4-methylbenzene)sulfonamide (121 mg).
[Physicochemical Properties of Compound (75)]
$^1$H-NMR (CDCl$_3$): 2.42(3H, s), 2.56(3H, s), 5.44(2H, s), 6.40(1H, d, J=8 Hz), 7.28–7.33(3H, m), 7.70–7.80(4H, m), 7.98(2H, d, J=18 Hz) Mass(ESI): m/z 420(M-H).

EXAMPLE 64

Synthesis of 1-(2-Chloro-4-(trifluoromethyl) benzyl)-2-methyl-6-((4-vinylbenzene) sulfonylcarbamoyl)benzimidazole (76)

In the same manner as in Example 1, 1-(2-chloro-4-(trifluoromethyl)benzyl)-2-methyl-6-(4-vinylbenzene) sulfonyl-carbamoyl)benzimidazole (76) (190 mg) was obtained as white crystals from 6-carboxy-1-(2-chloro-4-(trifluoromethyl)benzyl)-2-methyl-benzimidazole (175 mg) as obtained in Production Example 13 and (4-vinylbenzene) sulfonamide (121 mg).
[Physicochemical Properties of Compound (76)]
$^1$H-NMR(CDCl$_3$): 2.56(3H, s), 5.42(2H, s), 5.45(1H, d, J=10 Hz), 5.89(1H, d, J=16 Hz), 6.38(1H, d, J=8 Hz), 6.74(1H, dd, J=16,10 Hz), 7.29(1H, d, J=8 Hz), 7.53(2H, d, J=8 Hz), 7.66–7.79(5H, m), 8.05(2H, s, J=8 Hz). Mass(ESI): m/z 532(M-H).

PRODUCTION EXAMPLE 32

<First Step>

Production of (R)-3-Hydroxy-1-(p-toluenesulfonyloxy)butane

After adding pyridine (100 ml) to (R)-1,3-butanediol (86.0 g), the solution was cooled to −25° C. under nitrogen atmosphere. A solution of p-toluenesulfonyl chloride (200 g) in pyridine (200 ml) was slowly added dropwise thereto at a temperature ranging from −20 to −10° C. The mixture was stirred for 1 hour at a temperature ranging from −20 to −10° C. A small amount of water was added to the reaction mixture to stop the reaction and the solution was extracted with toluene and water. The organic layer was washed with water, dried over sodium sulfate, and concentrated under reduced pressure to obtain (R)-3-hydroxy-1-(p-toluenesulfonyloxy)butane (209 g) as light brown oil. The oil thus obtained was used in the next step as such without purification.

<Second Step>

Production of (R)-2-Methyloxethane

A mixture of potassium hydroxide (180 g) and water (18.0 g) was heated at 150° C. to melt potassium hydroxide. (R)-3-hydroxy-1-(p-toluenesulfonyloxy)butane (209 g) was added dropwise thereto. Liquid discharged during reaction was collected by distillation under normal pressure in a receiver. Light brown liquid thus obtained was allowed to stand overnight. The supernatant was collected, dried with potassium hydroxide, and distilled under normal pressure to obtain (R)-2-methyl-oxethane (16.6 g). The oil obtained was immediately subjected to the next step.

<Third Step>

Production of (R)-N-t-butyl 4hydroxy-1-pentanesulfonamide.

A solution of 2.0 M lithium diisopropylamide in heptane/ tetrahydrofuran/ethylbenzene (100 ml) was slowly added dropwise to a solution of N-t-butylmethanesulfonamide (15.1 g) in tetrahydrofuran (100 ml) under nitrogen atmosphere taking about 1 hour at −50 to −20° C. After stirring for 1 hour at 0° C. and cooling to −50° C., (R)-1-methyloxethane (8.51 g) was added dropwise thereto. After stirring for 5 days at room temperature, the solution was extracted with water and ethyl acetate. The organic layer was washed with water, dried over sodium sulfate, and concentrated under reduced pressure. The residue was purified by silica gel column chromatography (eluate: hexane/ethyl acetate=½) to obtain crude (R)-N-t-butyl-4-hydroxy-1-pentanesulfonamide (6.6 g) as solid. This solid was dissolved by adding chloroform and concentrated under reduced pressure. The residue thus obtained was crystallized by adding diethyl ether. The crystals were separated by filtration and dried under reduced pressure to obtain (R)-N-t-butyl-4-hydroxy-1-pentanesulfonamide (3.39 g) as white crystals.
[Physicochemical Properties of the Compound]
$^1$H-NMR (CDCl$_3$, δ ppm): 1.22(3H, d, J=6.1 Hz), 1.38 (9H, s), 1.53–1.63(3H, m), 1.85–2.02(2H, m), 3.09(2H, t, J=7.8 Hz), 3.80–3.87(1H, m), 4.10(1H, brs).

<Fourth Step>

Production of (R)-t-butyl-4-benzoyloxy-1-pentanesulfonamide

In the same manner as in the sixth step of Production Example 16, the desired compound (2.35 g) was obtained as yellow oil from (R)-N-t-butyl-4-hydroxy-1-pentanesulfonamide (1.50 g), benzoic acid (1.72 g), N,N'-carbonyldiimidazole (2.29 g), and diazabicyclo-undecene (0.92g).
[Physicochemical Properties of the Compound]
$^1$H-NMR (CDCl$_3$, δ ppm): 1.33(9H, s), 1.37(3H, d, J=6.3 Hz), 1,77–2.02(4H, m), 3.03–3.13(2H, m), 4.02(1H, brs), 5.17–5.22(1H, m), 7.44(2H, t, J=7.8 Hz), 7.56(1H, t, J=7.4 Hz), 8.03(2H, dd, J=1.4 and 8.3 Hz). Optical purity: 97.2% ee (conditions of high-performance liquid chromatography: CHIRALPAK AD, hexane/ethanol=9/1, 1.0 ml/min, 254 nm, 40° C.).

<Fifth Step>

Production of (R)4-Benzoyloxy-1-pentanesulfonamide

In the same manner as in the seventh step of Production Example 16, the desired compound (1.62 g) was obtained as light yellow oil from (R)-N-t-butyl-4-benzoyloxy-1-pentanesulfonamide (2.15 g).
[Physicochemical Properties of the Compound]
$^1$H-NMR (CDCl$_3$, δ ppm): 1.38(3H, d, J=6.3 Hz), 1,77–2.03(4H, m), 3.12–3.22(2H, m), 4.68(2H, brs), 5.18–5.24(1H, m), 7.44(2H, t, J=7.9 Hz), 7.56(1H, t, J=7.5 Hz), 8.03(2H, dd, J=1.4 and 8.0 Hz).

<Sixth Step>

Production of Sodium Salt of (R)-6-((4-Benzoyl-1-pentane)-sulfonylcarbamoyl)-1-(2,4-dichlorobenzyl)-2-methylbenzimidazole N,N-dimethylformamide was added to 6-carboxy-1-(2,4-dichlorobenzyl)-2-methylbenzimidazole (1.28 g) as obtained in Production Example 14 and N,N'-carbonyldiimidazole (0.84 g) and the solution was stirred for about 30 minutes at room temperature. Then, diazabicycloundecene (0.78 g) and (R)-4-benzoyloxy-1-pentane-sulfonamide (1.40 g) were added thereto and the solution was stirred for 15 hours at 80° C. The mixture was concentrated and ethanol (15 ml) and water (7.5 ml) were added thereto. After adjusting the pH to 5 with dilute hydrochloric acid, the solution was extracted with ethyl acetate. An aqueous solution of sodium hydrogencarbonate was added to the organic layer. After stirring the mixture for about 1 hour at room temperature, deposited crystals were collected by filtration, washed with water and ethyl acetate, and dried under reduced pressure to obtain sodium salt of (R)-6-((4-benzoyl-1-pentane)sulfonylcarbamoyl)-1-(2,4-dichlorobenzyl)-2-methyl-benzimidazole (1.82 g) as light yellowish white crystals.

[Physicochemical property of the compound]
$^1$H-NMR (DMSO-d6, δ ppm): 1.24(3H, d, J=6.8 Hz), 1.48–1.75(4H, m), 2.47(3H, s), 3.07(2H, t, J=7.8 Hz), 5.00–5.08(1H, m), 5.51(2H, s), 7.42–7.47(3H, m), 7.61(1H, t, J=7.4 Hz), 7.71(1H, d, J=2.2 Hz), 7.81–7.85(2H, m), 7.89(2H, dd, J=1.2 and 8.1 Hz).

EXAMPLE 65

Production of (R)-1-(2,4-Dichlorobenzyl)-6-((4-hydroxy-1-pentane)sulfonylcarbamoyl)-2-methylbenzimidazole (77)

Sodium hydroxide (0.335 g), water (15 ml), and ethanol (10 ml) were added to sodium salt of (R)-6-((4-benzoyl-1-pentane)-sulfonylcarbamoyl)-1-(2,4-dichlorobenzyl)-2-methylbenzimidazole (1.70 g) as obtained in Production Example 32 and the mixture was stirred for 3 hours at 70° C. The reaction solution was cooled to room temperature and the pH was adjusted to 5 with hydrochloric acid. Deposited crystals were collected by filtration, washed with a mixed solution of ethanol and water (1:1, 8 ml), and dried at about 80° C. under reduced pressure to obtain white crude crystals (1.06 g). After dissolving the crude crystals (1.00 g) in acetone (20 ml), diethyl ether (20 ml) was added thereto and the solution was stirred for a while. Deposited crystals were collected by filtration, washed with diethyl ether, and dried under reduced pressure to give (R)-1-(2,4-dichlorobenzyl)-6-((4-hydroxy-1-pentane)sulfonylcarbamoyl)-2-methylbenzimidazole (0.76 g, 56%). The crystals (168 mg) were dissolved in a mixed solution of acetone and water (9:1, 4 ml) at 60° C. in an oil bath. Water (10 ml) was slowly added dropwise thereto to precipitate crystals. The mixture was stirred for 1.5 hours while the solution was cooled slowly to room temperature. The crystals deposited were collected by filtration and dried to obtain white crystals of (R)-1-(2,4-dichlorobenzyl)-6-((4-hydroxy-1-pentane)-sulfonylcarbamoyl)-2-methylbenzimidazole (77) (144 mg).

[Physicochemical Properties of Compound (77)]
$^1$H-NMR (DMSO-d6, δ ppm): 1.00(3H, d, J=6.1 Hz), 1.35–1.48(2H, m), 1.65–1.85(2H, m), 2.49(3H, s), 3.51(2H, t, J=7.9 Hz), 3.56(1H, m), 4.44(1H, brs), 5.59(2H, s), 6.44(1H, d, J=8.4 Hz), 7.33(1H, dd, J=8.4 and 2.1 Hz), 7.69(1H, d, J=8.5 Hz), 7.76(1H, d, J=2.1 Hz), 7.81(1H, dd, J=8.4 and 1.5 Hz), 8.11(1H, d, J=1.5 Hz), 11.86(1H, brs). IR(Nujol): 1682 cm$^{-1}$. mp: 194.6–194.9° C. Optical purity: 97.9% ee (retention time: 23.3 min, high-performance liquid chromatography, column: CHIRALCEL OD 250 mm×4.6 mm φ, particle diameter of filler: 20 □m, eluate: hexane/ethanol/methanol/trifluoroacetic acid=85/10/5/0.1, flow rate: 1.0 ml/min, column temperature: room temperature).

PRODUCTION EXAMPLE 33

<First Step>

Production of (S)-3-Hydroxy-1-(p-toluenesulfonyloxy)butane

In the same manner as in the first step of Production Example 32, the desired compound (77.5 g) was obtained as light brown oil from (S)-1,3-butanediol (30.0 g) and p-toluenesulfonyl chloride (69.8 g). The thus-obtained oil was immediately subjected to the next step.

<Second Step>

Production of (S)-2-Methyloxethane

In the same manner as in the second step of Production Example 32, the desired compound (5.28 g) was obtained as colorless oil from potassium hydroxide (74.7 g), water (7.0 g) and (S)-3-hydroxy-1-(p-toluenesulfonyloxy)butane (75.3 g).

[Physicochemical Property of the Compound]
$^1$H-NMR (CDCl$_3$, δ ppm): 1.42(3H, d, J=6.1 Hz), 2.28–2.37(1H, m), 2.67–2.73(1H, m), 4.47–4.54(1H, m), 4.60–4.67(1H, m), 4.96–5.04(1H, m).

<Third Step>

Production of (S)-N-t-butyl-4-hydroxy-1-pentanesulfonamide

In the same manner as in the third step of Production Example 32, the desired compound (1.98 g) was obtained as white crystals from N-t-butylmethanesulfonamide (9.86 g), a solution of 2.0 M lithium diisopropylamide in heptane/tetrahydrofuran/ethylbenzene (65 ml) and (S)-1-methyloxethane (4.54 g).

[Physicochemical Property of the Compound]
$^1$H-NMR (CDCl$_3$, δ ppm) :1.22(3H, d, J=6.3 Hz), 1.37 (9H, s), 1.54–1.62(2H, m), 1.64–1.73(1H, brs), 1.85–2.02 (2H, m), 3.08(2H, t, J=7.7 Hz), 3.80–3.87(1H, m), 4.32(1H, brs).

<Fourth Step>

Production of (S)-N-t-butyl-4-benzoyloxy-1-pentanesulfonamide

In the same manner as in the fourth step of Production Example 32, a yellow oil crude product (2.29 g) was obtained from (S)-N-t-butyl-4-hydroxy-1-pentanesulfonamide (1.50 g), benzoic acid (1.72 g), N,N'-carbonyldiimidazole (2.29 g), and diazabicycloundecene (2.15 g). This product was dissolved in heated t-butyl methyl ether (4 ml) and hexane (10 ml) was added thereto for crystallization. The crystals were collected by filtration, washed with hexane, and dried to obtain the desired compound (1.63 g).

[Physicochemical Property of the Compound]
$^1$H-NMR (CDCl$_3$, δ ppm): 1.33(9H, s), 1.37(3H, d, J=6.2 Hz), 1,77–2.01(4H, m), 3.03–3.12(2H, m), 4.06(1H, brs), 5.16–5.23(1H, m), 7.44(2H, t, J=7.6 Hz), 7.55(1H, t, J=7.5 Hz), 8.03(2H, dd, J=8.1 and 0.8 Hz). Optical purity: 99.6% ee (conditions of high-performance liquid chromatography: CHIRALPAK AD, hexane/ethanol=9/1, 1.0 ml/min, 254 nm, 40° C.).

<Fifth Step>

Production of (S)-4-Benzoyloxy-1-pentanesulfonamide

In the same manner as in the fifth step of Production Example 32, the desired compound (1.28 g) was obtained as light yellow oil from (S)-N-t-butyl-4-benzoyloxy-1-pentanesulfonamide (1.63 g).

[Physicochemical Property of the Compound]
$^1$H-NMR(CDCl$_3$, δ ppm) :1.38(3H, d, J=6.2 Hz), 1.78–2.06(4H, m), 3.13–3.24(2H, m), 4.68(2H, brs), 5.18–5.24(1H, m), 7.44(2H, t, J=7.9 Hz), 7.56(1H, t, J=7.4 Hz), 8.03(2H, dd, J=7.8 and 1.4 Hz).

<Sixth Step>

Production of (S)-6-((4-Benzoyloxy-1-pentane)sulfonylcarbamoyl)-1-(2,4-dichlorobenzyl)-2-methylbenzimidazole N,N-dimethylformamide was added to 6-carboxy-1-(2,4-dichlorobenzyl)-2-methylbenzimidazole (1.26 g) as obtained in Production Example 14 and N,N'-carbonyldiimidazole (0.80 g) and the mixture was stirred for about 30 minutes at room temperature. Then, diazabicycloundecene (0.75 g) and (S)-4-benzoyloxy-1-pentane-sulfonamide (1.28 g) were added thereto and the solution was stirred for 14 hours at 90° C. The mixture was concentrated and ethanol (15 ml) and water (7.5 ml) were added thereto. After adjusting the pH to 5 with dilute hydrochloric acid, the mixture was stirred for about 1 hour at room temperature. The deposited crystals were collected by filtration, washed with a mixed solution of ethanol and water (1/1), and dried under reduced pressure to obtain (S)-6-((4-benzoyloxy-1-pentane)sulfonylcarbamoyl)-1-(2,4-dichlorobenzyl)-2-methyl-benzimidazole (1.91 g) as white crystals. This compound was immediately subjected to the next step.

EXAMPLE 66

Production of (S)-1-(2,4-Dichlorobenzyl)-6-((4-hydroxy-1-pentane)sulfonylcarbamoyl)-2-methylbenzimidazole (78)

In the same manner as in Example 65, crude crystals (1.01 g) were obtained from (S)-6-((4-benzoyloxy-1-pentane)sulfonyl-carbanoyl)-1-(2,4dichlorobenzyl)-2-methylbenzimidazole (1.88 g) as obtained in Production Example 33, sodium hydroxide (0.391 g), water (10 ml), and ethanol (10 ml). The crystals (0.72 g) were dissolved in methanol (15 ml) at 70° C. and the mixture was cooled to room temperature with stirring. The precipitated crystals were collected by filtration and dried under reduced pressure to give white crystals (307 mg). The crystals were dissolved in a mixed solution of acetone and water (9/1, 8 ml) at 60° C. Water (20 ml) was slowly added dropwise thereto to deposit crystals. The mixture was stirred for 2 hours while the solution was allowed to cool slowly to room temperature. The crystals deposited were collected by filtration and dried to yield white crystals of (S)-1-(2,4-dichlorobenzyl)-6-(4-hydroxy-1-pentanesulfonylcarbamoyl)-2-methylbenzimidazole (78) (218 mg).
[Physicochemical Properties of Compound (78)]
$^1$H-NMR (DMSO-d6, δ ppm): 1.00(3H, d, J=6.1 Hz), 1.35–1.47(2H, m), 1.65–1.85(2H, m), 2.49(3H, s), 3.50(2H, t, J=7.9 Hz), 3.56(1H, m), 4.43(1H, brs), 5.59(2H, s), 6.44(1H, d, J=8.4 Hz), 7.32(1H, dd, J=8.4 and 2.0 Hz), 7.68(1H, d, J=8.5 Hz), 7.75(1H, d, J=2.0 Hz), 7.81(1H, dd, J=8.4 and 1.0 Hz), 8.11(1H, s), 11.85(1H, brs). IR(Nujol): 1682cm$^{-1}$. mp: 195.0–195.8° C. Optical purity: 99.7% ee (retention time: 20.5 min, high-performance liquid chromatography, column: CHIRALCEL OD 250 mm×4.6 mm φ, particle diameter of filler: 20 □m, eluate: hexane/ethanol/methanol/trifluoroacetic acid=85/10/5/0.1, flow rate: 1.0 ml/min, column temperature: room temperature).

PRODUCTION EXAMPLE 34

Production of Optically Active 6-((2-Benzoyloxy-1-pentane)sulfonylcarbamoyl)-1-(2,4-dichlorobenzyl)-2-methylbenzimidazole 6-((2-Benzoyloxy-1-pentane)sulfonylcarbamoyl)-1-(2,4-dichlorobenzyl)-2-methylbenzimidazole (580 mg) as obtained in Production Example 15 was dissolved in ethanol (29 ml) and subjected to high-performance liquid chromatography (column: CHIRALPAK AD 250 mm×10 mm φ, particle diameter of filler: 20 □m, eluate: hexane/ethanol/trifluoroacetic acid=50/50/0.1, flow rate: 3.0 ml/min, column temperature: 40° C., sample injection volume: 20 mg/l ml×29 times) to obtain both of the optical isomers independently. The fraction containing the isomer with shorter retention time (420 ml) was concentrated to about 1/2 volume. Chloroform (200 ml) and water (400 ml) were added thereto and a saturated aqueous solution of sodium hydrogencar (10 ml) was further added thereto under stirring to adjust the pH of the aqueous layer to 7. 1 N Hydrochloric acid (3 ml) was further added thereto. The organic layer was separated, washed with water (200 ml), dried over sodium sulfate, and concentrated under reduced pressure. Thus, optically active 6-((2-benzoyloxy-1-pentane)sulfonylcarbamoyl)-1-(2,4dichloro-benzyl)-2-methylbenzimidazole isomer with shorter retention time (285 mg, retention time: 10.9 min) was obtained with optical purity of 100% ee.

The fraction containing isomer with longer retention time (800 ml) was treated in the same manner as described above and optically active 6-((2-benzyloxy-1-pentane)sulfonylcarbamoyl)-1-(2,4-dichlorobenzyl)-2-methylbenzimidazole isomer with longer retention time (273 mg, retention time: 19.1 min) was obtained with optical purity of 100% ee. These compounds were immediately subjected to the next step.

EXAMPLE 67

Production of Optically Active 1-(2-,4-Dichlorobenzyl)-6-((2-hydroxy-1-pentane)sulfonylcarbamoyl)-2-methylbenzimidazole with longer retention time (79)

Methanol (2 ml) and a 10% aqueous solution of sodium hydroxide (0.2 ml) were added to optically active 6-(2-benzoyloxy-1-pentane)sulfonylcarbamoyl-1-(2,4-dichlorobenzyl)-2-methyl-benzimidazole isomer with shorter retention time as obtained in Production Example 34 (277 mg) and the mixture was stirred for 90 minutes at room temperature. A 10% aqueous solution of sodium hydroxide (0.36 ml) was further added thereto and stirring was continued for 50 minutes under heating at 50° C. The solution was allowed to cool for 70 minutes to room temperature and 1N hydrochloric acid (1.4 ml) was added thereto and the resulting solution was cooled with ice. Deposited crystals were collected by filtration, washed three times with water (2 ml) and twice with chloroform (1ml), and dried by heating under reduced pressure to obtain optically active 1-(2,4-dichlorobenzyl)-6(2-hydroxy-1-pentane)sulfonylcarbamoyl)-2-methylbenzimidazole with longer retention time on CHIRALPAK AD (79) (143 mg).
[Physicochemical Properties of Compound (79)]
$^1$H-NMR (DMSO-d6, δ ppm): 0.81(3H, t, J=7.2 Hz), 1.26–1.46(4H, m), 2.49(3H, s), 3.49(1H, dd, J=14.4 and 4.1 Hz), 3.59(1H, dd, J=14.4 and 7.2 Hz), 3.95(1H, brs), 4.90 (1H, brs), 5.57(2H, s), 6.42(1H, d, J=8.4 Hz), 7.32(1H, d, J=8.4 Hz), 7.67(1H, d, J=8.4 Hz), 7.75(1H, s), 8.79(1H, d, J=8.4 Hz), 8.09(1H, s), 11.77(1H, brs). mp: 183–185° C. Optical purity: 100% ee (retention time: 22.3 min, high-performance liquid chromatography, column: CHIRALPAK AD 250 mm×4.6 mm φ, particle diameter of filler: 20 □m, eluate: hexane/ethanoltisopropanolttrifluoroacetic acid=85/10/5/0.1, flow rate: 1.0 ml/min, column temperature: room temperature).

EXAMPLE 68

Production of Optically Active 1-(2,4-Dichlorobenzyl)-6-((2-hydroxy-1-pentane)sulfonylcarbamoyl)-2-methylbenzimidazole with shorter retention time (80)

In the same manner as in Example 67, optically active 1-(2,4-dichlorobenzyl)-6-((2-hydroxy-1-pentane)sulfonylcarbamoyl)-2-methylbenzimidazole with shorter retention time on CHIRALPAK AD (80) (136 mg) was obtained from optically active 6-((2-benzoyloxy-1-pentane)sulfonylcarbamoyl)-1-(2,4-dichlorobenzyl)-2-methylbenzimidazole isomer with longer retention time as obtained in Production Example 34 (260 mg).

[Physicochemical Properties of Compound (80)]

$^1$H-NMR (DMSO-d6, δ ppm): 0.81(3H, t, J=7.2 Hz), 1.26–1.46(4H, m), 2.49(3H, s), 3.49(1H, dd, J=14.4 and 4.1 Hz), 3.59(1H, dd, J=14.4 and 7.2 Hz), 3.95(1H, brs), 4.90 (1H, brs), 5.57(2H, s), 6.42(1H, d, J=8.4 Hz), 7.32(1H, d, J=8.4 Hz), 7.67(1H, d, J=8.4 Hz), 7.75(1H, s), 8.79(1H, d, J=8.4 Hz), 8.09(1H, s), 11.77(1H, brs). mp: 187–188° C. Optical purity: 100% ee (retention time: 17.2 min, high-performance liquid chromatography, column: CHIRALPAK AD 250 mm×4.6 mm φ, particle diameter of filler: 20 □m, eluate: hexane/ethanol/isopropanol/trifluoroacetic acid=85/10/5/0.1, flow rate: 1.0 ml/min, column temperature: room temperature).

PRODUCTION EXAMPLE 35

Production of Optically Active 3-Benzoyloxy-1-pentanesulfonamide

3-Benzoyloxy-1-pentanesulfonamide (1.50 g) as obtained in the third step of Production Example 17 was dissolved in a mixed solution of hexane and isopropanol (7/3, 50 ml). The solution was subjected to high-performance liquid chromatography (column: CHIRALPAK AS 250 mm×10 mm φ, particle diameter of filler: 20 □m, eluate: hexane/isopropanol=7/3, flow rate: 5.0 ml/min, column temperature: 40° C., sample injection volume: 1.0–1.2 ml×22 times) to collect both of the optical isomers independently. After concentrating each fraction, toluene (5 ml×2 times) was added thereto. The fractions were concentrated under reduced pressure again. Thus, optically active 3-benzoyloxy-1-pentanesulfonamide isomer with shorter retention time (350 mg, retention time: 10.7 min, optical purity: 99.08 % ee) was obtained as well as that with longer retention time (350 mg, retention time: 16.2 min. optical purity: 99.57% ee). These compounds were immediately subjected to the next step.

PRODUCTION EXAMPLE 36

Production of Sodium Salt of Optically Active 6-((3-Benzoyloxy-1-pentane)sulfonylcarbamoyl)-1-(2,4-dichlorobenzyl)-2-methyl-benzimidazole N,N'-carbonyldiimidazole (0.209 g) was added to an N,N'-dimethylformamide solution (2 ml) of 6-carboxy-1-(2,4-dichlorobenzyl)-2-methylbenzimidazole (0.288 g) as obtained in Production Example 14 and the mixture was stirred for 40 minutes at room temperature. Isomer of optically active 3-benzoyloxy-1-pentane sulfonamide with shorter retention time (0.350 g)as obtained in Production Example 35 and diazabicycloundecene (0.196 g) were added thereto and the solution was stirred overnight at 80° C. The solvent was removed under reduced pressure and methanol (3 ml) and water (3 ml) were added to the residue to make the solution homogeneous. Then, the pH was adjusted to about 6 with hydrochloric acid. After addition of water, the solution was extracted twice with ethyl acetate and the organic layer was concentrated under reduced pressure. To the resulting residue were added ethyl acetate (5 ml) and a saturated aqueous solution of sodium hydrogencarbonate (4 ml). After stirring for 1 hour, the precipitated solid was collected by filtration, washed with water and ethyl acetate, and dried to obtain sodium salt of optically active 6-((3-benzoyloxy-1-pentane)sulfonylcarbamoyl)-1-(2,4-dichlorobenzyl)-2-methylbenzimidazole (0.497 g).

[Physicochemical Property of the Compound]

$^1$H-NMR (DMSO-d6, δ ppm): agree with the spectrum of its racemate.

PRODUCTION EXAMPLE 37

Production of Sodium Salt of Optically Active 6-((3-Benzoyloxy-1-pentane)sulfonylcarbamoyl)-1-(2,4-dichlorobenzyl)-2-methyl-benzimidazole In the same manner as in Production Example 36, sodium salt of optically active 6-((3-benzoyloxy-1-pentane)sulfonyl carbamoyl)-1-(2,4-dichlorobenzyl)-2-methylbenzimidazole (0.436 g) was obtained from 6-carboxy-1-(2,4-dichlorobenzyl)-2-methyl benzimidazole (0.288 g) obtained in Production Example 14, N,N'-carbonyldiimidazole (0.209 g), optically active 3-benzoyloxy-1-pentane sulfonamide isomer with longer retention time (0.305 g) obtained in Production Example 35, and diazabicycloundecene (0.196 g).

[Physicochemical Property of the Compound]

$^1$H-NMR (DMSO-d6, δ ppm): agree with the spectrum of its racemate.

EXAMPLE 69

Production of Optically Active 1-(2,4-Dichlorobenzyl)-6-((3-hydroxy-1-pentane)sulfonylcarbamoyl-2-methylbenzimidazole with longer retention time (81)

A mixture of sodium salt of optically active 6-((3-benzoyloxy-1-pentane)sulfonylcarbamoyl)-1-(2,4-dichlorobenzyl)-2-methylbenzimidazole (0.400 g) as obtained in Production Example 36, sodium hydroxide (0.053 g), water (1.7 ml), and methanol (2.7 ml) was stirred for 6.5 hours at 60° C. The reaction solution was cooled to room temperature and the pH was adjusted to 4–5 by adding 1 N hydrochloric acid, thereby resulting in precipitation of an oily substance. After removing the supernatant, the oily substance was washed with water (1ml). Water (1.7 ml) and methanol (6.5 ml) were added to the oily substance and refluxed under heating to make a solution homogeneous. Cooling the solution to room temperature, the deposited crystals were collected by filtration, washed (methanol/water=3/1, 18 ml), and dried. Water (1.7 ml) and methanol (6.5 ml) were added to the thus-obtained crystals and refluxed under heating to make the solution homogeneous. The solution was cooled to room temperature and deposited crystals were collected by filtration, washed (methanol/water=3/1, 10 ml), and dried. Thus, optically active 1-(2,4-dichlorobenzyl)-6-((3-hydroxy-1-pentane)sulfonylcarbamoyl-2-methylbenzimidazole with longer retention time on CHIRALCEL OD-RH (81) (125 mg) was obtained as white crystals.

[Physicochemical Properties of Compound (81)]

$^1$H-NMR (DMSO-d6, δ ppm): agree with the spectrum of its racemate. mp: 191.5–192.8° C. Optical purity: 98.7% ee (retention time: 45.2 min, high-performance liquid chromatography, column: CHIRALCEL OD-RH 150 mm×4.6 mm φ, particle diameter of filler: 20 □m, eluate: a 0.6 M aqueous solution of potassium hexafluorophosphate (the pH was adjusted to 2.0 with 85% phosphoric acid)/acetonitrile=7/3, flow rate: 0.7 ml/min, column temperature: 10° C.).

EXAMPLE 70

Production of Optically Active 1-(2,4-Dichlorobenzyl)-6-(3-hydroxy-1-pentane) sulfonylcarbamoyl-2-methylbenzimidazole with shorter retention time (82)

In the same manner as in Example 69, the desired compound with shorter retention time on CHIRALCEL OD-RH (82) (118 mg) was obtained as white crystals from sodium salt of optically active 6-((3-benzoyloxy-1-pentane) sulfonylcarbamoyl)-1-(2,4-dichlorobenzyl)-2-methylbenzimidazole (0.400 g) as obtained in Production Example 37.
[Physicochemical Properties of Compound (82)]
$^1$H-NMR (DMSO-d6, δ ppm): agree with the spectrum of its racemate. mp: 192.8–193.6° C. Optical purity: >99% ee (retention time: 36.6 min, high-performance liquid chromatography, column: CHIRALCEL OD-RH 150 mm×4.6 mm φ, particle diameter of filler: 20 □m, eluate: a 0.1 M aqueous solution of potassium hexafluorophosphate (the pH was adjusted to 2.0 with 85% phosphoric acid)/acetonitrile=7/3, flow rate: 0.7 ml/min, column temperature: 10° C.).

EXAMPLE 71

Production of 1-(2-Chloro-4-(1-hexyl)benzyl)-2-methyl-((4-methylbenzene)sulfonylcarbamoyl) benzimidazole (83)

A mixture of 1-(2-chloro-4-(1-hexen-1-yl)benzyl)-2-methyl-6-((4-methylbenzene)sulfonylcarbamoyl) benzimidazole (0.082g) as obtained in Example 46, acetic acid (1 ml), ethyl acetate (4 ml), and platinum oxide (0.015 g) was stirred for 3 hours under hydrogen atmosphere. Solid was separated by filtration. The filtrate was concentrated and purified by silica gel thin-layer chromatography to obtain 1-(2-chloro-4-(1-hexyl)benzyl)-2-methyl-((4-methylbenzene)sulfonylcarbamoyl)benzimidazole (83) (0.080 g).
[Physicochemical Properties of Compound (83)]
$^1$H-NMR (DMSO-d6, δ ppm): 0.82(3H, t), 1.23(6H, m), 1.50(2H, m), 2.37(3H, s), 2.46(3H, s), 2.52(2H, m), 5.53 (2H, s), 6.33(1H, m), 7.04(1H, t, J=8.2 Hz), 7.41(3H, m), 7.63(1H, d, J=8.2 Hz), 7.70(1H, d, J=8.5 Hz), 7.85(2H, d, J=8.3 Hz), 8.04(1H, s), 12.29(1H, brs). IR(Nujol): 1619 cm$^{-1}$. mp: 195–196.5° C.

EXAMPLE 72

Production of 1-(2-Chloro-4-(1-hexyl)benzyl)-2-methyl-6-(pentanesulfonylcarbamoyl)benzimidazole (84)

In the same manner as in Example 71, the desired compound (0.064 mg) was obtained from 1-(2-chloro-4-(1-hexen-1-yl)benzyl)-2-methyl-6-(pentanesulfonylcarbamoyl)benzimidazole (0.093 g) as obtained in Example 45.
[Physicochemical Properties of Compound (84)]
$^1$H-NMR (DMSO-d6, δ ppm): 0.80(6H, m), 1.19–1.39 (10H, m), 1.50(2H, m), 1.67(2H, m), 2.48(3H, s), 2.53(2H, m), 3.48(2H, m), 5.55(2H, s), 6.36(1H, d, J=8.0 Hz), 7.05 (1H, d, J=8.0 Hz), 7.39(1H, s), 7.67(1H, d, J=8.5 Hz), 7.79(1H, d, J=8.5 Hz), 8.10(1H, s), 11.86(1H, brs). IR(Nujol): 1669 cm$^{-1}$. mp: 167–169° C.

PRODUCTION EXAMPLE 38
<First Step>

Production of 1-(2-Chloro-4-(thiophen-2-yl)benzyl)-6-(ethoxy-carbonyl)-2-methylbenzimidazole 1-(2-Chloro-4-iodobenzyl)-6-(ethoxycarbonyl)-2-methyl-benzimidazole (1.00 g) as obtained in Production Example 23, thiophene-2-borate (0.34 g), tetrakis (triphenylphosphine)palladium (IV) (0.06 g), a 2 M sodium carbonate aqueous solution (2.2 ml), toluene (3 ml), and ethanol (1 ml) were mixed and refluxed for 2.5 hours under heating. The solution was allowed to cool to room temperature. After addition of toluene (50 ml) and water (50 ml), the solution was filtered with celite. The organic layer was separated, dried over anhydrous sodium sulfate, and concentrated under reduced pressure. The resulting oil was purified by recrystallization from ethanol/water (15 ml/15 ml) to obtain the desired 1-(2-chloro-4(thiophene-2-yl) benzyl)-6-(ethoxy-carbonyl)-2-methylbenzimidazole (0.60 g).
[Physicochemical Property of the Compound]
$^1$H-NMR (DMSO-d6, δ ppm): 1.28(3H, t, J=7.0 Hz), 2.54(3H, s), 4.26(2H, q, J=7.0 Hz), 5.63(2H, s), 6.61(1H, d, J=8.0 Hz), 7.13(1H, d, J=4.0 Hz), 7.49(1H, d, J=8.0 Hz), 7.57(1H, d, J=4.2 Hz), 7.66(1H, d, J=8.4 Hz), 7.81(1H, d, J=8.4 Hz), 7.84(1H, s), 8.01(1H, s).
<Second Step>

Production of 6-Carboxy-1-(2-chloro-4-(thiophen-2-yl)benzyl)-2-methylbenzimidazole 1-(2-chloro-4-(thiophen-2-yl)benzyl)-6-(ethoxycarbonyl)-2-methylbenzimidazole (0.60 g), a 10% aqueous solution of sodium hydroxide (2 ml), and ethanol (5 ml) were mixed and refluxed for 15 minutes under heating. After allowing the solution to cool to room temperature. insoluble matter was removed by filtration with celite. The filtrate was adjusted to pH 6 with 1N hydrochloric acid (about 4 ml). The deposited crystals were collected by filtration, washed with 50% aqueous ethanol, and dried under reduced pressure to obtain the desired compound, 6-carboxy-1-(2-chloro-4-(thiophen-2-yl) benzyl)-2-methylbenzimidazole (0.208 g).
[Physicochemical Property of the Compound]
$^1$H-NMR (DMSO-d6, δ ppm): 2.53(3H, s), 5.61(2H, s), 6.56(1H, d, J=8.1 Hz), 7.13(1H, m), 7.50(1H, dd, J=1.8 and 8.1 Hz), 7.58(2H, m), 7.61(1H, d, J=8.4 Hz), 7.80(1H, dd, J=1.4 and 8.4 Hz), 7.84(1H, d, J=1.8 Hz), 7.97(1H, s).

EXAMPLE 73

Production of 1-(2-Chloro-4-(thiophen-2-yl)benzyl)-2-methyl-6-((4-methylbenzene)sulfonylcarbamoyl) benzimidazole (85)

In the same manner as in Example 1, the desired benzimidazole (85) was obtained from carboxylic acid obtained in Production Example 38 and (4-methylbenzene) sulfonamide.
[Physicochemical Properties of Compound (85)]
$^1$H-NMR (DMSO-d6, δ ppm): 2.36(3H, s), 2.49(3H, s), 5.59(2H, s), 6.45(1H, d, J=8.1 Hz), 7.13(1H, m), 7.38(2H, d, J=8.2 Hz), 7.48(1H, d, J=8.2 Hz), 7.58(2H, m), 7.64(1H, d, J=8.5 Hz), 7.71(1H, d, J=8.5 Hz), 7.85(3H, m), 8.07(1H, s), 12.32(1H, brs). IR(Nujol): 1698 cm$^{-1}$. mp: 207.5–208.5° C.

EXAMPLE 74

Production of 1-(2-Chloro-4-(thiophen-2-yl)benzyl)-2-methyl-6-(1-pentanesulfonylcarbamoyl)benzimidazole (86)

In the same manner as in Example 1, the desired benzimidazole (86) was obtained from carboxylic acid obtained in Production Example 38 and 1-pentanesulfonamide.

[Physicochemical Properties of Compound (86)]
$^1$H-NMR (DMSO-d6, δ ppm): 0.79(3H, t, J=7.3 Hz), 1.24(2H, m), 1.33(2H, m), 1.66(2H, m), 2.52(3H, s), 3.48 (2H, t, J=7.7 Hz), 5.61(2H, s), 6.48(1H, d, J=8.2 Hz), 7.13(1H, m), 7.49(1H, d, J=8.1 Hz), 7.58(2H, m), 7.68(1H, d, J=8.5 Hz), 7.80(1H, d, J=8.4 Hz), 7.86(1H, s), 8.12(1H, s), 11.88(1H, brs). IR(Nujol): 1684 cm$^{-1}$. mp: 213–216° C.

PRODUCTION EXAMPLE 39

<First Step>

Production of 1-(2-Chloro-4-(furan-2-yl)benzyl)-6-(ethoxy-carbonyl)-2-methylbenzimidazole 1-(2-Chloro-4-iodobenzyl)-6-(ethoxycarbonyl)-2-methyl-benzimidazole (1.00 g) as obtained in Production Example 23, furan-2-boric acid (0.30 g), tetrakis(triphenylphosphine)palladium (IV) (0.06 g), a 2 M sodium carbonate aqueous solution (2.2 ml), toluene (3 ml), and ethanol (1 ml) were mixed and refluxed for 2.5 hours under heating. The solution was allowed to cool to room temperature and extracted with toluene (50 ml) and water (50 ml). The organic layer was dried over anhydrous sodium sulfate and concentrated under reduced pressure. The oil thus obtained was recrystallized from ethanol/water (20 ml/20 ml) to obtain the desired compound, 1-(2-chloro-4-(furan-2-yl)benzyl)-6-(ethoxycarbonyl)-2-methylbenzimidazole (0.73 g).

[Physicochemical Property of the compound]
$^1$H-NMR (DMSO-d6, δ ppm): 1.27(3H, t, J=7.1 Hz), 2.53(3H, s), 4.26(2H, q, J=7.1 Hz), 5.63(2H, s), 6.59(1H, dd, J=3.3 and 1.8 Hz), 6.65(1H, d, J=8.1 Hz), 7.05(1H, d, J=3.2 Hz), 7.50(1H, d, J=8.1 Hz), 7.65(1H, d, J=8.4 Hz), 7.75(1H, s), 7.80(1H, d, J=8.4 Hz), 7.86(1H, s), 8.00(1H, s).

<Second Step>

Production of 6-Carboxy-1-(2-chloro-4-(furan-2-yl)benzyl)-2-methylbenzimidazole 1-(2-Chloro-4-(thiophen-2-yl)benzyl-6-(ethoxycarbonyl)-2-methylbenzimidazole (0.73 g, 1.85 mmol), a 10% sodium hydroxide aqueous solution (2 ml), and ethanol (15 ml) were mixed and refluxed for 1.5 hours under heating. The solution was allowed to cool to room temperature. The pH of the solution was adjusted to 6 with 1N hydrochloric acid (about 6 ml). After adding water (10 ml), deposited crystals were collected by filtration, rinsed with 50% aqueous ethanol, and dried under reduced pressure to obtain desired 6-carboxy-1-(2-chloro-4-(furan-2-yl)benzyl)-2-methylbenzimidazole (0.305 g).

[Physicochemical Property of the Compound]
$^1$H-NMR (DMSO-d6, δ ppm): 2.53(3H, s), 5.62(2H, s), 6.59(1H, m), 6.62(1H, d, 8.1 Hz), 7.05(1H, d, J=3.3 Hz), 7.54(1H, d, J=8.0 Hz), 7.64(1H, d, J=8.4 Hz), 7.75(1H, s), 7.80(1H, d, J=8.4 Hz), 7.86(1H, s), 7.99(1H, s), 12.70(1H, brs).

EXAMPLE 75

Production of 1-(2-Chloro-4-(furan-2-yl)benzyl)-2-methyl-6-(1-pentanesulfonylcarbamoyl)benzimidazole (87)

In the same manner as in Example 1, the desired benzimidazole (87) was obtained from carboxylic acid obtained in Production Example 39 and 1-pentanesulfonamide.

[Physicochemical Properties of Compound (87)]
$^1$H-NMR (DMSO-d6, δ ppm): 0.79(3H, t, J=7.3 Hz), 1.24(2H, m), 1.35(2H, m), 1.66(2H, m), 2.51(3H, s), 3.48 (2H, t, J=7.7 Hz), 5.60(2H, s), 6.53(1H, d, J=8.2 Hz), 6.59(1H, m), 7.05(1H, d, J=3.3 Hz), 7.54(1H, d, J=8.1 Hz), 7.68(1H, d, J=8.6 Hz), 7.76(1H, s), 7.80(1H, d, J=8.4 Hz), 7.88(1H, s), 8.12(1H, s), 11.90(1H, brs). IR(Nujol): 1690 cm$^{-1}$. mp: 221.8–222.7° C.

EXAMPLE 76

Production of 1-(2-Chloro-4-(furan-2-yl)benzyl)-2-methyl-6-((4-methylbenzene)sulfonylcarbamoyl)benzimidazole (88)

In the same manner as in Example 1, the desired benzimidazole (88) was obtained from carboxylic acid obtained in Production Example 39 and (4-methylbenzene)sulfonamide.

[Physicochemical Properties of Compound (88)]
$^1$H-NMR (DMSO-d6, δ ppm): 2.36(3H, s), 2.50(3H, s), 5.59(2H, s), 6.50(1H, d, J=8.2 Hz), 6.60(1H, m), 7.05(1H, d, J=3.2 Hz), 7.39(2H, d, J=8.0 Hz), 7.53(1H, d, J=8.1 Hz), 7.64(1H, d, J=8.5 Hz), 7.72(1H, d, J=8.4 Hz), 7.76(1H, s), 7.85(2H, d, J=8.2 Hz), 7.87(1H, s), 8.07(1H, s), 12.31(1H, brs). IR(Nujol): 1614cm$^{-1}$. mp: 154.2–155.9° C.

EXAMPLE 77

Production of 1-(2-Chloro-4-(phenylethynyl)benzyl)-2-methyl-6-((4-methylbenzene)sulfonylcarbamoyl)benzimidazole (89)

In the same manner as in Example 1, the desired benzimidazole (89) was obtained from carboxylic acid obtained in Production Example 23 and (4-methylbenzene)sulfonamide.

[Physicochemical Properties of Compound (89)]
$^1$H-NMR (DMSO-d6, δ ppm): 2.34(3H, s), 2.47(3H, s), 5.61(2H, s), 6.44(1H, d, J=8.1 Hz), 7.37–7.44(6H, m), 7.52–7.57(2H, m), 7.64(1H, d, J=8.2 Hz), 7.72(1H, d, J=7.1 Hz), 7.77(1H, d, J=1.7 Hz), 7.85(2H, d=8.3 Hz), 8.06(1H, s). IR(Nujol):1682 cm$^{-1}$. mp: 222.4–228.5° C.

EXAMPLE 78

Production of 1-(2-Chloro-4-(phenylethynyl)benzyl)-2-methyl-6-((E)-1-pentene-1-sulfonylcarbamoyl)benzimidazole (90)

In the same manner as in Example 1, the desired benzimidazole (90) was obtained from carboxylic acid obtained in Production Example 23 and 1-pentane-1-sulfonamide.

[Physicochemical Properties of Compound (90)]
$^1$H-NMR (DMSO-d6, δ ppm): 0.85(3H, t, J=7.0 Hz), 1.43(2H, q, J=7.3 Hz), 2.22(2H, m), 5.62(2H, s), 6.48(1H, d, J=8.3 Hz), 6.76(1H, d, J=14.9 Hz), 6.81–6.89(1H, m), 7.39–7.45(4H, m), 7.52–7.58(2H, m), 7.67(1H, d, J=3.9 Hz), 7.78(2H, m), 8.10(1H, s), 11.97(1H, brs). IR(Nujol): 1673 cm$^{-1}$. mp: 242.7–244.0° C.

EXAMPLE 79

Production of 1-(2-Chloro-4-(phenylethynyl)benzyl)-2-methyl-6-((4-vinylbenzene)sulfonylcarbamoyl)benzimidazole (91)

In the same manner as in Example 1, the desired benzimidazole (91) was obtained from carboxylic acid obtained in Production Example 23 and (4-vinylbenzene)sulfonamide.

[Physicochemical Properties of Compound (91)]
¹H-NMR(DMSO-d6, δ ppm): 5.44(1H, d, J=11.0 Hz), 5.62(2H, s), 5.99(1H, d, J=17.7 Hz), 6.44(1H, d, J=8.1 Hz), 6.80(1H, dd, J=11.0, 17.7 Hz), 7.38–7.45(4H, m), 7.52–7.56 (2H, m), 7.62–7.74(4H, m), 7.77(1H, d, J=1.6 Hz), 7.93(2H, d, J=8.4 Hz), 8.07(1H, s), 12.39(1H, brs). IR(Nujol): 1694 cm⁻¹. mp: 237.5–238.5° C.

EXAMPLE 80

Production of 1-(2-Chloro-4-(phenylethynyl)benzyl)-2-methyl-6-((E)-2-phenylethenylsulfonylcarbamoyl)benzimidazole (92)

In the same manner as in Example 1, the desired benzimidazole (92) was obtained from carboxylic acid obtained in Production Example 23 and ((E)-2-phenylethenyl)sulfonamide.
[Physicochemical Properties of Compound (92)]
¹H-NMR (DMSO-d6, δ ppm): 5.62(2H, s), 6.45(1H, d, J=8.2 Hz), 7.38–7.47(7H, m), 7.49(1H, d, J=15.6 Hz), 7.53–7.58(2H, m), 7.63(1H, d, J=15.5 Hz), 7.67(1H, d, J=8.5 Hz), 7.73–7.77(2H, m), 7.78(1H, s), 7.80(1H, d, J=8.5 Hz), 8.13(1H, s), 12.17(1H, brs). IR(Nujol): 1672 cm⁻¹. mp: 239.1–241.8° C.

EXAMPLE 81

Production of 1-(2-Chloro-4-((E)-2-phenylethenyl)benzyl)-6-((4-vinylbenzene)sulfonylcarbamoyl)-2-methylbenzimidazole (93)

In the same manner as in Example 1, the desired benzimidazole (93) was obtained from carboxylic acid obtained in Production Example 24 and (4-vinylbenzene)sulfonamide.
[Physicochemical Properties of Compound (93)]
¹H-NMR (DMSO-d6, δ ppm): 5.39(1H, d, J=11.0 Hz), 5.57(2H, s), 5.95(1H, d, J=17.6 Hz), 6.45(1H, d, J=8.1 Hz), 6.77(1H, dd, J=17.6 and 10.9 Hz), 7.19(1H, d, J=6.5 Hz), 7.22–7.32(2H, m), 7.36(2H, t, J=7.6 Hz), 7.42(1H, d, J=8.0 Hz), 7.54–7.64(5H, m), 7.74(1H, d, J=8.4 Hz), 7.81(1H, s), 7.89(2H, d, J=8.3 Hz), 8.02(1H, s). IR(Nujol): 1682 cm⁻¹. mp: 142.5–144.5° C.

EXAMPLE 82

Production of 1-(2-Chloro-4(E)-2-phenylethenyl)benzyl)-6-((E)-1-pentene-1-sulfonylcarbamoyl)-2-methylbenzimidazole (94)

In the same manner as in Example 1, the desired benzimidazole (94) was obtained from carboxylic acid obtained in Production Example 24 and 1-pentene-1-sulfonamide.
[Physicochemical Properties of Compound (94)]
¹H-NMR (DMSO-d6, δ ppm): 0.84(3H, t, J=7.3 Hz), 1.37–1.44(2H, m), 2.21(2H, q, J=6.8 Hz), 2.51(3H, s), 5.59(2H, s), 6.46(1H, d, J=8.1 Hz), 6.75(1H, d, J=15.2 Hz), 6.80–6.87(1H, m), 7.21(1H, d, J=16.4 Hz), 7.24–7.37(4H, m), 7.43(1H, dd, J=8.2 and 1.5 Hz), 7.57(1H, d, J=7.4 Hz), 7.66(1H, d, J=8.5 Hz), 7.78(1H, dd, J=8.4 and 1.5 Hz), 7.83(1H, d, J=1.6 Hz), 8.09(2H, d, J=1.4 Hz), 12.04(1H, brs). IR(Nujol):1674 cm⁻¹. mp: 224.5–227.5° C.

EXAMPLE 83

Production of 1-(2-Chloro-4-((E)-2-phenylethenyl)benzyl)-2-methyl-6-((E)-2-phenylethenylsulfonylcarbamoyl)benzimidazole (95)

In the same manner as in Example 1, the desired benzimidazole (95) was obtained from carboxylic acid obtained in Production Example 24 and ((E)-2-phenylethenyl)sulfonamide.

[Physicochemical Properties of Compound (95)]
¹H-NMR (DMSO-d6, δ ppm): 2.50(3H, s), 5.59(2H, s), 6.46(1H, d, J=8.1 Hz), 7.20(1H, d, J=16.4 Hz), 7.25–7.32 (2H, m), 7.36(2H, t, J=7.7 Hz), 7.41–7.45(4H, m), 7.49(1H, d, J=15.4 Hz), 7.57(2H, d, J=7.9 Hz), 7.62(1H, d, J=15.5 Hz), 7.66(1H, d, J=8.5 Hz), 7.74(2H, d, J=7.8 Hz), 7.80(1H, d, J=8.5 Hz), 7.82(1H, s), 8.13(1H, s), 12.1(1H, brs). IR(Nujol): 1672 cm⁻¹. mp: 249.9–251.4° C.

PRODUCTION EXAMPLE 40

<First Step>

Production of 1-(2-Chloro-4-hydroxybenzyl)-6-(ethoxycarbonyl)-2-methylbenzimidazole Ethyl 4-(acetylamino)-3-aminobenzoate (6.34 g), 4-acetoxy-2-chlorobenzyl bromide (14.0 g), potassium carbonate (5.12 g), and sodium iodide (1.28 g) were added to ethyl acetate (35 ml) and uo (13 ml) and the whole was stirred for 15 hours at 70° C. The organic layer was separated, washed with water, and concentrated under reduced pressure. Ethanol (30 ml) and 35% hydrochloric acid (3.2 g) were added to the oily residue and the mixture was stirred for 3 hours at 70° C. After extraction of the reaction solution with ethyl acetate and water, the organic layer was separated and concentrated. The residue was crystallized by addition of ethanol. Crystals obtained by filtration was dried to obtain 1-(2-chloro-4-hydroxybenzyl)-6-(ethoxycarbonyl)-2-methylbenzimidazole (1.53 g).

Separately, the filtrate was concentrated and ethanol was added thereto to effect crystallization. Crystals obtained by filtration was dried to obtain 1-(2-chloro-4-hydroxybenzyl)-6-(ethoxycarbonyl)-2-methylbenzimidazole (4.72 g).
[Physicochemical Property of the Compound]
¹H-NMR(CDCl₃, δ ppm): 1.39(3H, t, J=7.1 Hz), 2.50(3H, s), 4.37(2H, q, J=7.1 Hz), 5.37(2H, s), 6.14(1H, d, J=8.4 Hz), 6.47(1H, dd, J=8.5 and 2.2 Hz), 7.01(1H, d, J=2.2Hz), 7.67(1H, d, J=8.4 Hz), 7.96(1H, d, J=8.8 Hz), 7.99(1H, s).
<Second Step>

Production of 1-(4-butyloxy-2-chlorobenzyl)-6-(ethoxycarbonyl)-2-methylbenzimidazole N,N-dimethylformamide (5 ml) was added to 60% sodium hydride (0.20 g, oily). Crystals of 1-(2-chloro-4-hydroxybenzyl)-6-(ethoxycarbonyl)-2-methylbenzimidazole (0.80 g) were added gradually thereto at room temperature. After stirring for 1 hour at room temperature, n-butyl bromide (0.28 g, 4.14 mmol) was added to the mixture. After further stirring for 15 hours at room temperature, water and subsequently ethyl acetate were added to the solution to effect extraction. The organic layer was separated, washed twice with water, and concentrated to obtain 0.62 g of oil.
[Physicochemical Property of the Compound]
¹H-NMR (CDCl₃, δ ppm): 0.95(3H, t, J=7.5 Hz), 1.39 (3H, t, J=7.3 Hz), 1.42–1.50(2H, m), 1.70–1.78(2H, m), 2.57(3H, s), 3.90(2H, t, J=6.4 Hz), 4.37(2H, q, J=6.9 Hz), 5.38(2H, s), 6.37(1H, d, J=8.6 Hz), 6.62(1H, dd, J=8.6 and 2.5 Hz), 7.00(1H, d, J=2.5 Hz), 7.73(1H, d, J=8.5 Hz), 7.96(1H, s), 7.98(1H, d, J=8.6 Hz).
<Third Step>

Production of 1-(4-Butyloxy-2-chlorobenzyl)-6-carboxy-2-methyl-benzimidazole>

Sodium hydroxide (0.17 g), ethanol (8 ml), and water (4 ml) were added to 1-(4-butyloxy2-chlorobenzyl)(ethoxycarbonyl)-2-methylbenzimidazole (0.62 g) and the whole was s d for 4 hours at 80° C. The pH was adjusted to about 5 with 35% hydrochloric acid. Deposited crystals were filtered and dried to obtain crystals (0.42 g) of 1-(4-butyloxy-2-chlorobenzyl)-6-carboxy-2-methyl-benzimidazole. [Physicochemical properties of the compound]

$^1$H-NMR (DMSO-d6, δ ppm): 0.89(3H, t, J=7.5 Hz), 1.35–1.42(2H, m), 1.60–1.68(2H, m), 2.52(3H, s), 3.94(2H, t, J=6.4 Hz), 5.51(2H, s), 6.56(1H, d, J=8.7 Hz), 6.81(1H, dd, J=8.7 and 2.5 Hz), 7.10(1H, d, J=2.5 Hz), 7.61(1H, d, J=8.4 Hz), 7.88(1H, dd, J=8.4 and 1.3 Hz), 7.94(1H, s), 12.68(1H, brs).

EXAMPLE 84

Production of 1-(4-Butyloxy-2-chlorobenzyl)-6-(1-pentane-sulfonylcarbamoyl)-2-methylbenzimidazole (96)

In the same manner as in Example 1, the desired benzimidazole (96) was obtained from carboxylic acid obtained in Production Example 40 and 1-pentanesulfonamide.

[Physicochemical Properties of Compound (96)]

$^1$H-NMR (DMSO-d6, δ ppm): 0.81(3H, t, J=7.2 Hz), 0.89(3H, t, J=7.4 Hz), 1.21–1.29(2H, m), 1.31–1.42(4H, m), 1.61–1.71(4H, m), 2.49(3H, s), 3.49(2H, t, J=7.7 Hz), 3.94 (2H, t, J=6.5 Hz), 5.50(2H, s), 6.45(1 H, d, J=8.7 Hz), 6.81(1H, dd, J=8.7 and 2.5 Hz), 7.12(1H, d, J=2.5 Hz), 7.65(1H, d, J=8.5 Hz), 7.78(1H, dd, J=8.4 and 1.5 Hz), 8.09(1H, s), 12.24(1H, brs). IR(Nujol): 1674 cm$^{-1}$. mp: 166.0–172.5° C.

PRODUCTION EXAMPLE 41

<First Step>

Production of 1-(2-Chloro-4-(3-methylbutoxy) benzyl)-6-(ethoxy-carbonyl)-2-methylbenzimidazole In the same manner as in the second step of Example Production 40, the desired compound (0.600 g) was obtained from 1-(2-chloro-4-hydroxybenzyl)-6-ethoxycarbonyl-2-methylbenzimidazole (0.600 g) and 1-bromo-3-methylbutane.

[Physicochemical Property of the Compound]

$^1$H-NMR(CDCl$_3$, δ ppm): 0.94(6H, d, J=6.7 Hz), 1.39 (3H, t, J=7.0 Hz), 1.64(1H, q, J=6.6 Hz), 1.76–1.83(1H, m), 2.57(3H, s), 3.93(2H, t, J=6.6 Hz), 4.37(2H, q, J=7.1 Hz), 5.38(2H, s), 6.36(1H, d, J=8.6 Hz), 6.62(1H, dd, J=8.7 and 2.5 Hz), 7.00(1H, d, J=2.5 Hz), 7.73(1H, d, J=8.5 Hz), 7.95–8.04(2H, m).

<Second Step>

Production of 1-(2-Chloro-4-(3-methylbutoxy) benzyl)-6-carboxy-2-methylbenzimidazole In the same manner as in the third step of Production Example 40, the desired compound (0.509 g) was obtained from 1-(2-chloro-4-(3-methylbutoxy)benzyl)-6-ethoxycarbonyl-2-methyl-benzimidazole (0.600 g).

[Physicochemical Properties of the Compound]

$^1$H-NMR(DMSO-d6, δ ppm): 0.89(6H, d, J=6.8 Hz), 1.56(2H, q, J=6.6 Hz), 1.68–1.77(1H, m), 2.52(3H, s), 3.96(2H, t, J=6.7 Hz), 5.52(2H, s), 6.56(1H, d, J=8.7 Hz), 6.82(1H, dd, J=8.6 and 2.5 Hz), 7.12(1H, d, J=2.6 Hz), 7.61(1H, d, J=8.5 Hz), 7.88(1H, dd, J=8.5 and 1.6 Hz), 7.94(1H, d, J=1.3 Hz), 11.70(1H, brs).

EXAMPLE 85

Production of 1-(2-Chloro-4-(3-methylbutoxy) benzyl)-2-methyl-6-(1-pentanesulfonylcarbamoyl) benzimidazole (97)

In the same manner as in Example 1, the desired benzimidazole (97) was obtained from carboxylic acid obtained in Production Example 41 and 1-pentanesulfonamide.

[Physicochemical Properties of Compound (97)]

$^1$H-NMR (DMSO-d6, δ ppm): 0.80(3H, t, J=7.2 Hz), 0.88(6H, d, J=6.6 Hz), 1.26(2H, m), 1.34(2H, m), 1.56(2H, m), 1.67(3H, m), 2.49(3H, s), 3.47(2H, t, J=7.7 Hz), 3.96 (2H, t, J=6.6 Hz), 5.50(2H,s), 6.45(1H, d, J=8.7 Hz), 6.81 (1H, d, J=8.6 Hz), 7.13(1H, d, J=2.4 Hz), 7.65(1H, d, J=8.5 Hz), 7.78(1H, d, J=8.4 Hz), 8.09(1H, s), 11.87(1H, brs). IR(Nujol): 1672 cm$^{-1}$. mp: 178.1–179.0° C.

EXAMPLE 86

Production of 1-(2-Chloro-4-(3-methylbutoxy) benzyl)-2-methyl-6-((4-methylbenzene) sulfonylcarbamoyl)benzimidazole (98)

In the same manner as in Example 1, the desired benzimidazole (98) was obtained from carboxylic acid obtained in Production Example 41 and (4-methylbenzene) sulfonamide.

[Physicochemical Properties of Compound (98)]

$^1$H-NMR (DMSO-d6, δ ppm): 0.89(6H,d, J=6.7 Hz), 1.56(2H, m), 1.72(1H, m), 2.38(3H, s), 2.47(3H, s), 3.96 (2H, t, J=6.5 Hz), 5.49(2H, s), 6.43(1H, d, J=8.5 Hz), 6.80(1H, d, J=8.5 Hz), 7.13(1H, s), 7.41(2H, d, J=8.0 Hz), 7.62(1H, d, J=8.4 Hz), 7.70(1H, d, J=8.2 Hz), 7.86(2H, d, J=8.2 Hz), 8.04(1H, s). IR(Nujol): 1606 cm$^{-1}$. mp: 218–226° C.

Test Example: Test for Activity of Decreasing Plasma Glucose using db/db Mice

Test Compounds 1-(Isoquinolin-3-ylmethyl)-2-methyl-6-(1-pentanesulfonyl-carbamoyl)benzimidazole (13)

Animal Used

Five-week-old female mice [C57BL/KsJ-dbm db+/db+, C57BL/KsJ-dbm +m/+m (Jackson Laboratory) were purchased, and were kept for 2 to 3 weeks. Then, these mice were used in the test.

Preparation of an Agent

A test compound was mixed with a powdered chow (CE-2, made by Nippon Clea) using a mortar. The mixing ratio was 0.01%. The mixed chow was changed twice a week. The feed amount and the remaining amount were recorded, and the intake was calculated from the difference therebetween.

Test Schedule

The female db/db mice were grouped according to the body weight, the plasma glucose and the plasma triglyceride concentrations. Then, the mixture containing the test compound was administered to the mice for 14 days (from 8 to 10 weeks old). In the morning on day 7 and day 14, the blood was collected from the orbital venous plexus using heparinized glass capillary tubes (Chase Heparinized Capillary Tubes), and a plasma fraction was obtained through centrifugal separation. Plasma glucose, triglyceride, and insulin concentrations were measured on day 0 and day 14 as well as plasma glucose and triglyceride concentrations on day 7. The body weight was measured on day 0, day 7 and day 14. After the final collection of the blood, the mice was killed using CO$_2$ gas.

Measurement Method

The plasma glucose was measured by a glucose oxidase method (Glucose CII-Test Wako made by Wako Pure Chemical Industries, Ltd.) using from 10 to 15 μl of plasma. The plasma triglyceride concentration was measured by a GPO-p-chlorophenol method (Triglyceride G-Test Wako made by Wako Pure Chemical Industries, Ltd.) or a GPO-DAOS method (Triglyceride E-Test Wako) using from 10 to 15 μl of plasma. The above-mentioned measurements were conducted immediately after the blood collection. The plasma insulin concentration was measured by radio immuno assay method (Phadesef Insulin RIA Kit made by Cabi Pharmacia) using 20 μl of plasma (which can be stored at −20° C.).

Results

The difference in the plasma glucose and the plasma triglyceride concentrations between the groups of the db/db mouse and the +/+ mouse was defined as 100%, and the rate (%) of decrease in the plasma glucose and the plasma triglyceride concentrations of the group to which the test compound was administered was calculated. As a result, when the test compound was administered at a dose of 10 mg/kg, plasma glucose decreasing activity was 44%, while TG concentration-decreasing activity was 77%.

INDUSTRIAL APPLICABILITY

Novel benzimidazole derivatives and their pharmaceutically acceptable salts are provided. These compounds and their salts have blood sugar level-depressing activity or PDE5-inhibiting activity, and are useful for preventing and treating impaired glucose tolerance, diabetes (type II diabetes), diabetic complications (e.g., diabetic gangrene, diabetic arthropathy, diabetic osteopenia, diabetic glomerulosclerosis, diabetic nephropathy, diabetic dermatopathy, diabetic neuropathy, diabetic cataract, diabetic retinopathy,. etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), polycystic ovary syndrome, hyperlipidemia, atherosclerosis, cardiovascular disorders (e.g., stenocardia, cardiac failure, etc.), hyperglycemia(e.g., abnormal saccharometabolism such as feeding disorders, etc.), or hypertension; or stenocardia, hypertension, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), autoimmune diseases, allergic rhinitis, urticaria, glaucoma, diseases characterized by enteromotility disorders (e.g., hypersensitive enteropathy dme, etc.), impotence (e.g., organic impotence, psychic impotence, etc.), and diabetic complications (e.g., diabetic gangrene, diabetic arthropathy, diabetic osteopenia, diabetic glomemlosclerosis, diabetic nephropathy, diabetic dermatopathy, diabetic neuropathy, diabetic cataract, diabetic retinopathy, etc.), nephritis, cachexia(e.g., progressive weight loss due to the lipolysis, myolysis, anemia, edema, anorexia, etc. associated with chronic diseases such as cancer, tuberculosis, endocrine disorder, AIDS, etc.), pancreatitis, or restenosis after PTCA.

What is claimed is:

1. A benzimidazole derivative represented by the following formula (I) or a salt thereof:

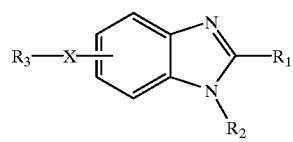

(I)

wherein $R_1$ represents a hydrogen atom, a lower alkyl group, a lower alkoxy group, or a lower alkylthio group;

$R_2$ represents an aromatic lower alkyl group, which may be substituted with one or more groups selected from a halogen atom, an alkyl group, a halo-lower alkyl group, a nitro group, a lower alkoxycarbonyl group, an aromatic group, an aromatic lower alkyloxy group, a lower cycloalkyloxy-lower alkyl group, an aromatic lower alkyl group, an aromatic lower alkenyl group, an aromatic lower alkynyl group, an aromatic oxy lower alkyl group, a lower cycloalkyl-lower alkyloxy group, an alkenyl group, a lower alkoxy group, a lower alkylthio group, a lower alkanesulfinyl group, a lower alkanesulfonyl group, and a lower alkanesulfonylcarbamoyl group; $R_3$ represents an alkyl group, a hydroxy lower alkyl group, an alkenyl group, an aromatic group, a halogenated aromatic group, a lower alkyl aromatic group, a lower alkenyl aromatic group, an aromatic lower alkyl group, or an aromatic lower alkenyl group; and —X— is a cross-linking group represented by any one of the following formulas (II) to (V):

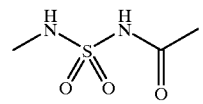

(II)

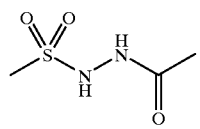

(III)

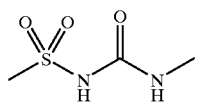

(IV)

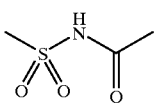

(V)

2. The benzimidazole derivative or a salt thereof according to claim 1, wherein $R_1$ is a lower alkyl group.

3. The benzimidazole derivative or a salt thereof according to claim 1, wherein —X— is a cross-linking group represented by the formula (V).

4. A pharmaceutical composition for preventing and treating impaired glucose tolerance, diabetes, diabetic complications, syndrome of insulin resistance, polycystic ovary syndrome, hyperlipidemia, atherosclerosis, cardiovascular disorders, hyperglycemia, hypertension, stenocardia, pulmonary hypertension, congestive heart failure, glomerulopathy, tubulointerstitial disorders, renal failure, atherosclerosis, angiostenosis, distal angiopathy, cerebral apoplexy, chronic reversible obstructions, autoimmune diseases, allergic rhinitis, urticaria, glaucoma, diseases characterized by enteromotility disorders, impotence, nephritis, cachexia, pancreatitis, or restenosis after PTCA, which comprises, as an active ingredient, a compound represented by the following formula (I) or a pharmaceutically acceptable salt thereof:

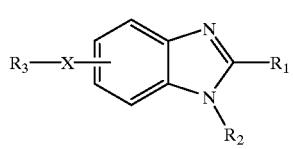

(I)

wherein $R_1$ represents a hydrogen atom, a lower alkyl group, a lower alkoxy group, or a lower alkylthio group;

$R_2$ represents an aromatic lower alkyl group, which may be substituted with one or more groups selected from a halogen atom, an alkyl group, a halo-lower alkyl group, a nitro group, a lower alkoxycarbonyl group, an aromatic group, an aromatic lower alkyloxy group, a lower cycloalkyloxy-lower alkyl group, an aromatic lower alkyl group, an aromatic lower alkenyl group, an aromatic lower alkynyl group, an aromatic oxy lower alkyl group, a lower cycloalkyl-lower alkyloxy group, an alkenyl group, a lower alkoxy group, a lower alkylthio group, a lower alkanesulfinyl group, a lower alkanesulfonyl group, and a lower alkanesulfonylcarbamoyl group;

$R_3$ represents an alkyl group, a hydroxy lower alkyl group, an alkenyl group, an aromatic group, a halogenated aromatic group, a lower alkyl aromatic group, a lower alkenyl aromatic group, an aromatic lower alkyl group, or an aromatic lower alkenyl group; and —X— is a cross-linking group represented by any one of the following formulas (II) to (V):

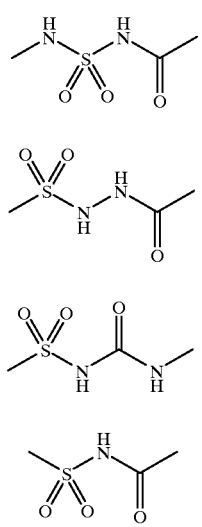

5. The benzimidazole derivative or a salt thereof according to claim 1, wherein $R_2$ represents an aromatic lower alkyl group, which may be substituted with one or more groups selected from a halogen atom, an alkyl group, an aromatic group, an alkenyl group, a lower alkoxy group, a lower alkylthio group, a lower alkanesulfinyl group, and a lower alkanesulfonyl group, $R_3$ represents an alkyl group, a hydroxy lower alkyl group, an alkenyl group, an aromatic group, an aromatic lower alkyl group, a lower alkyl aromatic group, or an aromatic lower alkenyl group, and —X— is a cross-linking group represented by the formula (V).

6. The benzimidazole derivative or a salt thereof according to claim 5, wherein $R_1$ represents a hydrogen atom or a lower alkyl group, $R_2$ represents an aromatic lower alkyl group, which may be substituted with one or more halogen atoms, and $R_3$ represents a hydroxy lower alkyl group or an alkenyl group.

7. The benzimidazole derivative or a salt thereof according to claim 6, wherein $R_1$ represents a lower alkyl group, $R_2$ represents a benzyl group, a naphthylmethyl group, or an isoquinolylmethyl group, which may be substituted with one or more halogen atoms, and $R_3$ represents a hydroxy lower alkyl group or an alkenyl group.

8. A pharmaceutical composition for preventing and treating impaired glucose tolerance, diabetes, diabetic complications, syndrome of insulin resistance, polycystic ovary syndrome, hyperlipidemia, atherosclerosis, cardiovascular disorders, hyperglycemia, hypertension, stenocardia, pulmonary hypertension, congestive heart failure, glomerulopathy, tubulointerstitial disorders, renal failure, atherosclerosis, angiostenosis, distal angiopathy, cerebral apoplexy, chronic reversible obstructions, autoimmune diseases, allergic rhinitis, urticaria, glaucoma, diseases characterized by enteromotility disorders, impotence, nephritis, cachexia, pancreatitis, or restenosis after PTCA, which comprises, as an active ingredient, the benzimidazole derivative or a pharmaceutically acceptable salt thereof according to claim 1, wherein $R_2$ represents an aromatic lower alkyl group, which may be substituted with one or more groups selected from a halogen atom, an alkyl group, an aromatic group, an alkenyl group, a lower alkoxy group, a lower alkylthio group, a lower alkanesulfinyl group, and a lower alkanesulfonyl group, $R_3$ represents an alkyl group, a hydroxy lower alkyl group, an alkenyl group, an aromatic group, an aromatic lower alkyl group, a lower alkyl aromatic group, or an aromatic lower alkenyl group, and —X— is a cross-linking group represented by the formula (V).

9. The pharmaceutical composition according to claim 8, wherein $R_1$ represents a hydrogen atom or a lower alkyl group, $R_2$ represents an aromatic lower alkyl group, which may be substituted with one or more halogen atoms, and $R_3$ represents a hydroxy lower alkyl group or an alkenyl group.

10. The pharmaceutical composition according to claim 9, wherein $R_1$ represents a lower alkyl group, $R_2$ represents a benzyl group, a naphthylmethyl group, or an isoquinolylmethyl group, which may be substituted with one or more halogen atoms, and $R_3$ represents a hydroxy lower alkyl group or an alkenyl group.

11. The benzimidazole derivative or a salt thereof according to claim 1, wherein $R_1$ represents a lower alkyl group, $R_2$ represents a benzyl group, which may be substituted with one or more groups selected from a halogen atom, an alkyl group, a halo-lower alkyl group, an aromatic group, a lower cycloalkyloxy-lower alkyl group, an aromatic lower alkenyl group, an aromatic lower alkynyl group, an alkenyl group, a lower alkylthio group, and a lower alkanesulfonylcarbamoyl group, and $R_3$ represents an alkyl group, an alkenyl group, an aromatic group, a halo-aromatic group, a lower alkenyl aromatic group, an aromatic lower alkyl group, a lower alkyl aromatic group, or an aromatic lower alkenyl group.

12. The benzimidazole derivative or a salt thereof according to claim 11, wherein $R_1$ represents a methyl group, $R_2$ represents a benzyl group, which may be substituted with one or more groups selected from a halogen atom, an alkyl group, a halo-lower alkyl group, a phenyl group, a lower cycloalkyloxy-lower alkyl group, a phenyl lower alkenyl group, a phenyl lower alkynyl group, an alkenyl group, a lower alkylthio group, and a lower alkanesulfonylcarbamoyl group, and $R_3$ represents an alkyl group, an alkenyl group, a phenyl group, a thiophenyl group, a halo-phenyl group, a lower alkenyl phenyl group, a phenyl lower alkyl group, a lower alkyl phenyl group, or a phenyl lower alkenyl group.

13. The pharmaceutical composition according to claim 4, wherein $R_1$ represents a lower alkyl group, $R_2$ represents a benzyl group, which may be substituted with one or more groups selected from a halogen atom, an alkyl group, a halo-lower alkyl group, an aromatic group, a lower cycloalkyloxy-lower alkyl group, an aromatic lower alkenyl group, an aromatic lower alkynyl group, an alkenyl group, a lower alkylthio group, and a lower alkanesulfonylcarbamoyl group, and $R_3$ represents an alkyl group, an alkenyl group, an aromatic group, a halo-aromatic group, a lower alkenyl aromatic group, an aromatic lower alkyl group, lower alkyl aromatic group, or an aromatic lower alkenyl group.

14. The pharmaceutical composition according to claim 13, wherein $R_1$ represents a methyl group, $R_2$ represents a benzyl group, which may be substituted with one or more groups selected from a halogen atom, an alkyl group, a halo-lower alkyl group, a phenyl group, a lower cycloalkyloxy-lower alkyl group, a phenyl lower alkenyl group, a phenyl lower alkynyl group, an alkenyl group, a lower alkylthio group, and a lower alkanesulfonylcarbamoyl group, and $R_3$ represents an alkyl group, an alkenyl group, a phenyl group, a thiophenyl group, a halo-phenyl group, a lower alkenyl phenyl group, a phenyl lower alkyl group, a lower alkyl phenyl group, or a phenyl lower alkenyl group.

15. The benzimidazole derivative or a salt thereof according to claim 1, which is selected from 1-(isoquinolin-3-ylmethyl)-2-methyl-6-(1-pentane-sulfonylcarbamoyl) benzimidazole, 1-((4-chloroisoquinolin-3-yl)methyl)-2-methyl-6-(1-pentanesulfonylcarbamoyl)benzimidazole, 1-(2,4-dichlorobenzyl)-2-methyl-6-(((E)-1-pent-1-en)sulfonylcarbamoyl)benzimidazole, 6-(N'-butanesulfonylhydrazinocarbamoyl)-1-(2,4-dichlorobenzyl)-2-methylbenzimidazole, 6-((n-butylaminosulfonyl)carbamoyl)-1-(2,4-dichlorobenzyl)-2-methylbenzimidazole, 1-(2,4-dichlorobenzyl)-2-methyl-6-[N'-(4-methylphenylsulfonyl)ureido]benzimidazole, 1-(2-chloro-4-(trifluoromethyl)benzyl)-2-methyl-6-(((E)-1-pent-1-en)sulfonylcarbamoyl)benzimidazole, 1-(2,4-dichlorobenzyl)-2-methyl-6-((E)-2-phenylethenylsulfonylcarbamoyl)benzimidazole, 1-(2-chloro-4-phenylbenzyl)-2-methyl-6-(((E)-1-pent-1-en)sulfonylcarbamoyl)benzimidazole, 1-(2-chloro-4-phenylbenzyl)-2-methyl-6-((E)-2-phenylethenylsulfonylcarbamoyl)benzimidazole, 1-(2-chloro-4-phenylbenzyl)-6-((5-chlorothiophen-2-yl)sulfonylcarbamoyl)-2-methylbenzimidazole, 1-(4-bromo-2-chlorobenzyl)-2-methyl-6-(((E)-1-pent-1-en)sulfonylcarbamoyl)benzimidazole, 1-(4-bromo-2-chlorobenzyl)-2-methyl-6-((E)-2-phenylethenylsulfonylcarbamoyl) benzimidazole, 1-(4-bromo-2-chlorobenzyl)- 6-((5-chlorothiophen-2-yl)sulfonylcarbamoyl)-2-methylbenzimidazole, 6-((5-bromothiophen-2-yl)sulfonylcarbamoyl)-1-(2,4-dichlorobenzyl)-2-methylbenzimidazole, 6-((5-bromothiophen-2-yl)sulfonylcarbamoyl)-1-(2-chloro-4-phenylbenzyl)-2-methylbenzimidazole, 1-(2-chloro-4-(cyclohexylmethyloxy)benzyl)-2-methyl-6-(1-pentanesulfonylcarbamoyl)benzimidazole, 1-(2-chloro-4-(cyclohexylmethyloxy)benzyl)-2-methyl-6-((4-methylbenzene)sulfonylcarbamoyl)benzimidazole, 6-((5-chlorothiophen-2-yl)-sulfonylcarbamoyl)-1-(2,4-dichlorobenzyl)-2-methylbenzimidazole, 1-(4-bromo-2-chlorobenzyl)-6-((5-bromothiophen-1-yl)sulfonylcarbamoyl)-2-methylbenzimidazole, 1-(2,4-dichlorobenzyl)-2-methyl-6-((4-vinylbenzene)sulfonylcarbamoyl)benzimidazole, 1-(2-chloro-4-bromobenzyl)-2-methyl-6-((4-vinylbenzene)sulfonylcarbamoyl)benzimidazole, 1-(2-chloro-4-phenylbenzyl)-2-methyl-6-((4-vinylbenzene)sulfonylcarbamoyl)benzimidazole, 1-(4-bromo-2-chlorobenzyl)-2-methyl-6-((1-pent-4-en)sulfonylcarbamoyl)-benzimidazole, 1-(2-chloro-4-phenylbenzyl)-2-methyl-6-(((E)-1-pent-4-en)sulfonylcarbamoyl)benzimidazole, 1-(2-chloro-4-(phenylethynyl)benzyl)-2-methyl-6-(1-pentanesulfonylcarbamoyl)benzimidazole, 1-(2-chloro-4-((E)-2-phenylethenyl)benzyl)-2-methyl-6-(1-pentanesulfonylcarbamoyl)benzimidazole, 1-(2-chloro-4-((E)-2-phenylethenyl)benzyl)-2-methyl-6-((4-methylbenzene)sulfonylcarbamoyl)benzimidazole, 1-(2-chloro-4-(1-hexen-1-yl)benzyl)-2-methyl-6-(1-pentanesulfonylcarbamoyl)benzimidazole, 1-(2-chloro-4-(1-hexen-1-yl)benzyl)-2-methyl-6-((4-methylbenzene)sulfonylcarbamoyl)benzimidazole, 1-(4-t-butylthio-2-chlorobenzyl)-2-methyl-6-(1-pentanesulfonylcarbamoyl)benzimidazole, 1-(4-t-butylthio-2-chlorobenzyl)-2-methyl-6-((4-methylbenzene)sulfonylcarbamoyl)benzimidazole, 1-(2-chloro-4-(cyclohexyloxymethyl)benzyl)-2-methyl-6-(1-pentanesulfonylcarbamoyl)benzimidazole, 1-(2-chloro-4-(cyclohexyloxymethyl)benzyl)-2-methyl-6-((4-methylbenzene)sulfonylcarbamoyl)benzimidazole, 1-(2-chloro-4-phenylbenzyl)-2-methyl-6-((n-pentylaminosulfonyl)carbamoyl)benzimidazole, 1-(2,4-dichlorobenzyl)-2-methyl-6-(((4-methylphenyl)aminosulfonyl)carbamoyl)benzimidazole, 1-(2-chloro-4-phenylbenzyl)-2-methyl-6-(((4-methylphenyl)trinsulfonyl)carbamoyl)benzimidazole, 1-(2-chloro-4-(1-pentanesulfonylcarbamoyl)benzyl)-2-methyl-6-(1-pentanesulfonylcarbamoyl)benzimidazole, 1-(2-chloro-4-(trifluoromethyl)benzyl)-2-methyl-6-((4-vinylbenzene)sulfonylcarbamoyl)benzimidazole, 1-(2-chloro-4-(phenylethynyl)benzyl)-2-methyl-6-((4-methylbenzene)sulfonylcarbamoyl)benzimidazole, 1-(2-chloro-4-(phenylethynyl)benzyl)-2-methyl-6-((E)-1-pentene-1-sulfonylcarbamoyl)benzimidazole, 1-(2-chloro-4-(phenylethynyl)benzyl)-2-methyl-6-((4-vinylbenzene)sulfonylcarbamoyl)benzimidazole, 1-(2-chloro-4-(phenylethynyl)benzyl)-2-methyl-6-((E)-2-phenylethenylsulfonylcarbamoyl)benzimidazole, 1-(2-chloro-4-((E)-2-phenylethenyl)benzyl)-6-((4-vinylbenzene)sulfonylcarbamoyl)-2-methylbenzimidazole, 1-(2-chloro-4-((E)-2-phenylethenyl)benzyl)-6-((E)-1-pentene-1-sulfonylcarbamoyl)-2-methylbenzimidazole, and 1-(2-chloro-4-((E)-2-phenylethenyl)benzyl)-2-methyl-6-(((E)-2-phenylethenyl)sulfonylcarbamoyl)benzimidazole.

16. The benzimidazole derivative or a salt thereof according to claim 1, which is selected from 1-((1-bromonaphthalen-2-yl)methyl)-2-methyl-6-(1-pentanesulfonylcarbamoyl)benzimidazole, 1-(2,4-dichlorobenzyl)-6-((2-hydroxy-1-pentane)sulfonylcarbamoyl)-2-methylbenzimidazole, 1-(2,4- dichlorobenzyl)-6-((4-hydroxy-1-pentane)sulfonylcarbamoyl)-2-methylbenzimidazole, 1-(2,4-dichlorobenzyl)-6-((3-hydroxy-1-pentane)sulfonylcarbamoyl)-2-methylbenzimidazole, 6-(benzenesulfonylcarbamoyl)-1-(2,4-dichlorobenzyl)-2-methylbenzimidazole, 1-(2-chloro-4-(trifluoromethyl)benzyl)-2-methyl-6-(1-pentanesulfonylcarbamoyl)benzimidazole, 1-(2-chloro-4-phenylbenzyl)-2-methyl-6-(1-pentanesulfonylcarbamoyl)benzimidazole, 1-(2-chloro-4-phenylbenzyl)-2-methyl-6-((4-methylbenzene)sulfonylcarbamoyl)benzimidazole, 1-(4-bromo-2-chlorobenzyl)-2-methyl-6-((4-methylbenzene)sulfonylcarbamoyl)benzimidazole, 1-(4-benzyloxy-2-chlorobenzyl)-2-methyl-6-(1-pentanesulfonylcarbamoyl)benzimidazole, 1-(4-benzyloxy-2-chlorobenzyl)-2-methyl-6-((4-methylbenzene)sulfonylcarbamoyl)-benzimidazole, 1-(2,4-dichlorobenzyl)-2-methyl-6-((4-methylbenzene)sulfonylcarbamoyl)benzimidazole, (+)-1-(1-(2,4-dichlorophenyl)ethyl)-2-methyl-6-(1-pentanesulfonylcarbamoyl)benzimidazole, (−)-1-(1-(2,4-dichlorophenyl)ethyl)-2-methyl-6-(1-pentanesulfonylcarbamoyl)benzimidazole, 1-(2-chloro-4-nitrobenzyl)-2-methyl-6-(1-pentanesulfonylcarbamoyl)benzimidazole, 1-(2-chloro-4-(2-phenylethyl)benzyl)-2-methyl-6-(1-pentanesulfonylcarbamoyl)benzimidazole, 1-(2-chloro-4-(phenoxymethyl)benzyl)-2-methyl-6-(1-pentanesulfonylcarbamoyl)benzimidazole, 1-(2-chloro-4-(phenoxymethyl)benzyl)-2-methyl-6-((4-methylbenzene)sulfonylcarbamoyl)benzimidazole, 1-(2-chloro-4-iodobenzyl)-2-methyl-6-(1-pentanesulfonylcarbamoyl)benzimidazole, 1-(2-chloro-4-iodobenzyl)-2-methyl-6-((4-methylbenzene)sulfonylcarbamoyl)benzimidazole, 1-(2-chloro-4-ethoxybenzyl)-2-methyl-6-(1-pentanesulfonylcarbamoyl)benzimidazole, 1-(2-chloro-4-ethoxybenzyl)-2-methyl-6-((4-methylbenzene)sulfonylcarbamoyl)benzimidazole, 1-(4-bromo-2-chlorobenzyl)-2-methyl-6-(1-pentanesulfonylcarbamoyl)benzimidazole, 1-(2-chloro-4-(trifluoromethyl)benzyl)-2-methyl-6-((4-methylbenzene)sulfonylcarbamoyl)benzimidazole, (R)-1-(2,4-dichlorobenzyl)-6-((4-hydroxy-1-pentane)sulfonylcarbamoyl)-2-methylbenzimidazole, (S)-1-(2,4-dichlorobenzyl)-6-((4-hydroxy-1-pentane)sulfonylcarbamoyl)-2-methylbenzimidazole, optically active 1-(2,4-dichlorobenzyl)-6-((2-hydroxy-1-pentane)sulfonylcarbamoyl)-2-methylbenzimidazole (showing longer retention time by liquid chromatography), optically active 1-(2,4-dichlorobenzyl)-6-((2-hydroxy-1-pentane)sulfonylcarbamoyl)-2-methylbenzimidazole (showing shorter retention time by liquid chromatography), optically active 1-(2,4-dichlorobenzyl)-6-((3-hydroxy-1-pentane)sulfonylcarbamoyl)-2-methylbenzimidazole (showing longer retention time by liquid chromatography), optically active 1-(2,4-dichlorobenzyl)-6-((3-hydroxy-1-pentane)sulfonylcarbamoyl-2-methylbenzimidazole (showing shorter retention time by liquid chromatography), 1-(2-chloro-4-(1-hexyl)benzyl)-2-methyl((4-methylbenzene)sulfonylcarbamoyl)benzimidazole, 1-(2-chloro-4-(1-hexyl)benzyl)-2-methyl-6-(pentanesulfonylcarbamoyl)benzimidazole, 1-(2-chloro-4-(thiophen-2-yl)benzyl)-2-methyl-6-((4-methylbenzene)sulfonylcarbamoyl)benzimidazole, 1-(2-chloro-4-(thiophen-2-yl)benzyl)-2-methyl-6-(1-pentanesulfonylcarbamoyl)benzimidazole, 1-(2-chloro-4-(furan-2-yl)benzyl)-2-methyl-6-(1-pentanesulfonylcarbamoyl)benzimidazole, 1-(2-chloro-4-(furan-2-yl)benzyl)-2-methyl-6-((4-methylbenzene)sulfonylcarbamoyl)benzimidazole, 1-(4-butyloxy-2-chlorobenzyl)-6-(1-pentanesulfonylcarbamoyl)-2-methylbenzimidazole, 1-(2-chloro-4-(3-methylbutoxy)benzyl)-2-methyl-6-(1-pentanesulfonylcarbamoyl)benzimidazole, and 1-(2-chloro-4-(3-methylbutoxy)benzyl)-2-methyl-6-((4-methylbenzene)sulfonylcarbamoyl)benzimidazole.

17. A method for preventing and treating impaired glucose tolerance, diabetes, diabetic complications, syndrome of insulin resistance, polycystic ovary syndrome, hyperlipidemia, atherosclerosis, cardiovascular disorders, hyperglycemia, hypertension, stenocardia, pulmonary hypertension, congestive heart failure, glomerulopathy, tubulointerstitial disorders, renal failure, atherosclerosis, angiostenosis, distal angiopathy, cerebral apoplexy, chronic reversible obstructions, autoimmune diseases, allergic rhinitis, urticaria, glaucoma, diseases characterized by enteromotility disorders, impotence, nephritis, cachexia, pancreatitis, or restenosis after PTCA, comprising administering to a patient an effective amount of a benzimidazole derivative represented by the following formula (I) or a salt thereof:

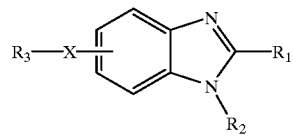

(I)

wherein $R_1$ represents a hydrogen atom, a lower alkyl group, a lower alkoxy group, or a lower alkylthio group;

$R_2$ represents an aromatic lower alkyl group, which may be substituted with one or more groups selected from a halogen atom, an alkyl group, a halo-lower alkyl group, a nitro group, a lower alkoxycarbonyl group, an aromatic group, an aromatic lower alkyloxy group, a lower cycloalkyloxy-lower alkyl group, an aromatic lower alkyl group, an aromatic lower alkenyl group, an aromatic lower alkynyl group, an aromatic oxy lower alkyl group, a lower cycloalkyl-lower alkyloxy group, an alkenyl group, a lower alkoxy group, a lower alkylthio group, a lower alkanesulfinyl group, a lower alkanesulfonyl group, and a lower alkanesulfonylcarbamoyl group;

$R_3$ represents an alkyl group, a hydroxy lower alkyl group, an alkenyl group, an aromatic group, a halogenated aromatic group, a lower alkyl aromatic group, a lower alkenyl aromatic group, an aromatic lower alkyl group, or an aromatic lower alkenyl group; and —X— is a cross-linking group represented by any one of the following formulas (II) to (V):

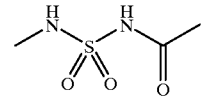

(II)

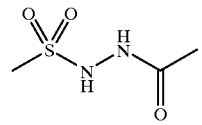

(III)

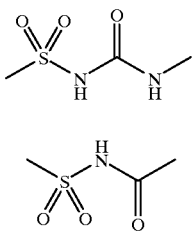

18. The method according to claim 17, wherein $R_2$ represents an aromatic lower alkyl group, which may be substituted with one or more groups selected from a halogen atom, an alkyl group, an aromatic group, an alkenyl group, a lower alkoxy group, a lower alkylthio group, a lower alkanesulfinyl group, and a lower alkanesulfonyl group, $R_3$ represents an alkyl group, a hydroxy lower alkyl group, an alkenyl group, an aromatic group, an aromatic lower alkyl group, a lower alkyl aromatic group, or an aromatic lower alkenyl group, and —X— is a cross-linking group represented by the formula (V).

19. The method according to claim 17, wherein the benzimidazole derivative is selected from the group consisting of 1-(isoquinolin-3-ylmethyl)-2-methyl-6-(1-pentanesulfonylcarbamoyl)-benzimidazole, 1-((4-chloroisoquinolin-3-yl)methyl)-2-methyl-6-(1-pentanesulfonyl-carbamoyl)benzimidazole, 1-(2,4-dichlorobenzyl)-2-methyl-6-(((E)-1-pent-1-en)-sulfonylcarbamoyl)benzimidazole, 6-(N'-butanesulfonylhydrazinocarbamoyl)-1-(2,4-dichlorobenzyl)-2-methylbenzimidazole, 6-((n-butylaminosulfonyl)carbamoyl)-1-(2,4-dichlorobenzyl)-2-methylbenzimidazole, 1-(2,4-dichlorobenzyl)-2-methyl-6-[N'-(4-methylphenylsulfonyl)ureido]benzimidazole, 1-(2-chloro-4-(trifluoromethyl)benzyl)-2-methyl-6-(((E)-1-pent-1-en)sulfonylcarbamoyl)benzimidazole, 1-(2,4-dichlorobenzyl)-2-methyl-6-((E)-2-phenylethenylsulfonylcarbamoyl)benzimidazole, 1-(2-chloro-4-phenylbenzyl)-2-methyl-6-(((E)-1-pent-1-en)sulfonylcarbarnoyl)benzimidazole, 1-(2-chloro-4-phenylbenzyl)-2-methyl-6-((E)-2-phenylethenylsulfonylcarbamoyl)benzimidazole, 1-(2-chloro-4-phenylbenzyl)-6-((5-chlorothiophen-2-yl)sulfonylcarbamoyl)-2-methylbenzimidazole, 1-(4-bromo-2-chlorobenzyl)-2-methyl-6-(((E)-1-pent-1-en)sulfonylcarbamoyl)benzimidazole, 1-(4-bromo-2-chlorobenzyl)-2-methyl-6-((E)-2-phenylethenylsulfonylcarbamoyl)benzimidazole, 1-(4-bromo-2-chlorobenzyl)-6-((5-chlorothiophen-2-yl)sulfonylcarbamoyl)-2-methylbenzimidazole, 6-((5-bromothiophen-2-yl)sulfonylcarbamoyl)-1-(2,4-dichlorobenzyl)-2-methylbenzimidazole, 6-((5-bromothiophen-2-yl)sulfonylcarbamoyl)-1-(2-chloro-4-phenylbenzyl)-2-methylbenzimidazole, 1-(2-chloro-4-(cyclohexylmethyloxy)benzyl)-2-methyl-6-(1-pentanesulfonylcarbamoyl)benzimidazole, 1-(2-chloro-4-(cyclohexylmethyloxy)-benzyl)-2-methyl-6-((4-methylbenzene)sulfonylcarbamoyl)benzimidazole, 6-((5-chlorothiophen-2-yl)sulfonylcarbamoyl)-1-(2,4-dichlorobenzyl)- 2-methylbenzimidazole, 1-(4-bromo-2-chlorobenzyl)-6-((5-bromothiophen-1-yl)sulfonylcarbamoyl)-2-methylbenzimidazole, 1-(2,4-dichlorobenzyl)-2-methyl-6-((4-vinylbenzene)-sulfonylcarbamoyl)benzimidazole, 1-(2-chloro-4-bromobenzyl)-2-methyl-6-((4-vinylbenzene) sulfonylcarbamoyl)benzimidazole, 1-(2-chloro-4-phenylbenzyl)-2-methyl-6-((4-vinylbenzene) sulfonylcarbamoyl)benzimidazole, 1-(4-bromo-2-chlorobenzyl)-2-methyl-6-((1-pent-4-en) sulfonylcarbamoyl)benzimidazole, 1-(2-chloro-4-phenybenzyl)-2-methyl-6-(((E)-1-pent-4-en) sulfonylcarbamoyl)benzimidazole, 1-(2-chloro-4-(phenylethynyl)benzyl)-2-methyl-6-(1-pentanesulfonylcarbamoyl)benzimidazole, 1-(2-chloro-4-((E)-2-phenylethenyl)benzyl)-2-methyl-6-(1-pentanesulfonylcarbamoyl)benzimidazole, 1-(2-chloro-4-((E)-2-phenylethenyl)benzyl)-2-methyl-6-((4-methylbenzene)sulfonylcarbamoyl)benzimidazole, 1-(2-chloro-4-(1-hexen-1-yl)benzyl)-2-methyl-6-(1-pentanesulfonylcarbamoyl)benzimidazole, 1-(2-chloro-4-(1-hexen-1-yl)-benzyl)-2-methyl-6-((4-methylbenzene) sulfonylcarbamoyl)benzimidazole, 1-(4-t-butylthio-2-chloro benzyl)-2-methyl-6-(1-pentanesulfonylcarbamoyl) benzimidazole, 1-(4-t-butylthio-2-chlorobenzyl)-2-methyl-6-((4-methylbenzene)sulfonylcarbamoyl)benzimidazole, 1-(2-chloro-4-(cyclohexyloxymethyl)benzyl)-2-methyl-6-(1-pentanesulfonylcarbamoyl)benzimidazole, 1-(2-chloro-4-(cyclohexyloxymethyl)benzyl)-2-methyl-6-((4-ethylbenzene)sulfonylcarbamoyl)benzimidazole, 1-(2-chloro-4-phenylbenzyl)-2-methyl-6-((n-pentylaminosulfonyl)carbamoyl)benzimidazole, 1-(2,4-dichlorobenzyl)-2-methyl-6-(((4-methylphenyl)aminosulfonyl)carbamoyl)benzimidazole, 1-(2-chloro-4-phenylbenzyl)-2 -methyl-6-(((4-methylphenyl)aminosulfonyl)carbamoyl)benzimidazole, 1-(2-chloro-4-(1-pentanesulfonylcarbamoyl)benzyl)-2-methyl-6-(1-pentanesulfonylcarbamoyl)benzimidazole, 1-(2-chloro-4-(trifluoromethyl)benzyl)-2-methyl 6-((4-vinylbenzene) sulfonylcarbamoyl)benzimidazole, 1-(2-chloro 4-(phenylethynyl)benzyl)-2-methyl-6-((4-methylbenzene) sulfonylcarbamoyl)-benzimidazole, 1-(2-chloro-4-(phenylethynyl)benzyl)-2-methyl-6-((E)-1-pentene-1-sulfonylcarbamoyl)benzimidazole, 1-(2-chloro-4-(phenylethynyl)benzyl)-2-methyl-6- ((4-vinylbenzene) sulfonylcarbamoyl)benzimidazole, 1-(2-chloro-4-(phenylethynyl)benzyl)-2-methyl-6-((E)-2-phenylethenylsulfonylcarbamoyl)benzimidazole, 1-(2-chloro-4-((E)-2-phenylethenyl)benzyl)-6-((4-vinylbenzene) sulfonylcarbamoyl)-2-methylbenzimidazole, 1-(2-chloro-4-((E)- 2-phenylethenyl)benzyl)-6-((E)-1-pentene-1-sulfonylcarbamoyl)-2-methylbenzimidazole, and 1-(2-chloro-4-((E)-2-phenylethenyl)benzyl)-2-methyl-6-(((E)-2-phenylethenyl)sulfonylcarbamoyl)-benzimidazole.

* * * * *

UNITED STATES PATENT AND TRADEMARK OFFICE
CERTIFICATE OF CORRECTION

PATENT NO.    : 6,420,409 B1
DATED         : July 16, 2002
INVENTOR(S)   : Noritsugu Yamasaki et al.

It is certified that error appears in the above-identified patent and that said Letters Patent is hereby corrected as shown below:

Title page,
Item [56], References Cited, U.S. PATENT DOCUMENTS,
delete "5,614,419" and insert -- 5,614,519 --.
OTHER PUBLICATIONS,
"Haque et al.," reference, "of Substituted and 2, 4-Disubstituted Benzimidazoles," and insert -- of 4-Substituted and 2, 4-Disubstituted Benzimidazoles --.

Column 41,
Line 43, delete "[□]$D^{25}$" and insert -- $\alpha D^{25}$ --.

Column 42,
Line 4, delete "[□]$D^{25}$" and insert -- $\alpha D^{25}$ --.

Column 52,
Line 41, delete "DMSO-6" and insert -- DMSO-d6 --.

Column 55,
Line 58, delete "20 □m" and insert -- 20$\mu$m --.

Column 57,
Line 58, delete "20 □m" and insert -- 20$\mu$m --.

Column 58,
Lines 4 and 64, delete "20 □m" and insert -- 20$\mu$m --.

Column 59,
Lines 24 and 39, delete "20 □m" and insert -- 20$\mu$m --.

Column 61,
Lines 3 and 27, delete "20 □m" and insert -- 20$\mu$m --.

Column 71,
Line 39, delete "any-one" and insert -- any one --.

Column 73,
Line 24, insert -- a -- before "lower alkyl aromatic group".

UNITED STATES PATENT AND TRADEMARK OFFICE
CERTIFICATE OF CORRECTION

PATENT NO.    : 6,420,409 B1
DATED         : July 16, 2002
INVENTOR(S)   : Noritsugu Yamasaki et al.

It is certified that error appears in the above-identified patent and that said Letters Patent is hereby corrected as shown below:

Column 77,
Line 32, delete "butanesulfonylhydrazinocarbamoyl" and insert
-- butanesulfonylhydrazinocarbonyl --.
Line 42, delete "sulfonylcarbarnoyl" and insert -- sulfonylcarbamoyl --.

Column 78,
Line 15, delete "phenybenzyl" and insert -- phenylbenzyl --.

Signed and Sealed this

Seventeenth Day of January, 2006

JON W. DUDAS
*Director of the United States Patent and Trademark Office*